US012543498B2

(12) United States Patent
Um et al.

(10) Patent No.: US 12,543,498 B2
(45) Date of Patent: Feb. 3, 2026

(54) HETEROCYCLIC COMPOUND, ORGANIC LIGHT-EMITTING DEVICE INCLUDING SAME

(71) Applicant: Samsung Display Co., Ltd., Yongin-si (KR)

(72) Inventors: Hyunah Um, Yongin-si (KR); Hyeongmin Kim, Yongin-si (KR); Heechoon Ahn, Yongin-si (KR); Yeseul Lee, Yongin-si (KR); Yirang Im, Yongin-si (KR); Seowon Cho, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 1325 days.

(21) Appl. No.: 17/203,651

(22) Filed: Mar. 16, 2021

(65) Prior Publication Data

US 2021/0399229 A1 Dec. 23, 2021

(30) Foreign Application Priority Data

Jun. 4, 2020 (KR) ........................ 10-2020-0067861

(51) Int. Cl.
*H10K 85/60* (2023.01)
*C07B 59/00* (2006.01)
(Continued)

(52) U.S. Cl.
CPC ....... *H10K 85/6572* (2023.02); *C07B 59/002* (2013.01); *C07D 209/88* (2013.01);
(Continued)

(58) Field of Classification Search
CPC .......................... H10K 85/6572; C07D 405/10
See application file for complete search history.

(56) References Cited

U.S. PATENT DOCUMENTS 5,948,941 A * 9/1999 Tamano ............... H10K 85/631
430/73
8,652,656 B2 2/2014 Zeng et al.
(Continued)

FOREIGN PATENT DOCUMENTS

CN 101133504 A 2/2008
CN 109320449 A 2/2019
(Continued)

*Primary Examiner* — Sean M DeGuire
(74) *Attorney, Agent, or Firm* — Womble Bond Dickinson (US) LLP

(57) ABSTRACT

Provided are a heterocyclic compound represented by Formula 1 and an organic light-emitting device including the heterocyclic compound. The organic light-emitting device includes: a first electrode; a second electrode facing the first electrode; an organic layer between the first electrode and the second electrode and including an emission layer; and at least one of the heterocyclic compound.
(Continued)

Formula 1

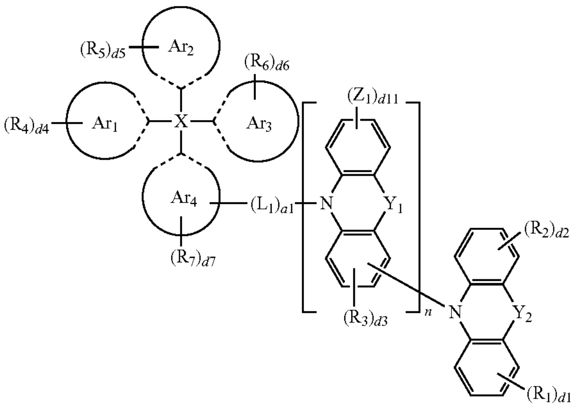

20 Claims, 4 Drawing Sheets

(51) Int. Cl.

| | |
|---|---|
| ***C07D 209/88*** | (2006.01) |
| ***C07D 405/10*** | (2006.01) |
| ***C07F 7/08*** | (2006.01) |
| ***C07F 7/22*** | (2006.01) |
| ***C07F 7/30*** | (2006.01) |
| *H10K 50/11* | (2023.01) |
| *H10K 101/10* | (2023.01) |

(52) U.S. Cl.

CPC .......... *C07D 405/10* (2013.01); *C07F 7/0812* (2013.01); *C07F 7/2208* (2013.01); *C07F 7/30* (2013.01); *H10K 50/11* (2023.02); *H10K 2101/10* (2023.02)

(56) References Cited

U.S. PATENT DOCUMENTS

| | | | | |
|---|---|---|---|---|
| 8,680,543 | B2 | 3/2014 | Takeda et al. | |
| 8,748,012 | B2 | 6/2014 | Zeng et al. | |
| 9,379,361 | B2 | 6/2016 | Tsurutani et al. | |
| 9,647,217 | B2 | 5/2017 | Lin et al. | |
| 10,135,002 | B2 | 11/2018 | Ono et al. | |
| 10,669,473 | B2 | 6/2020 | Ambrosek et al. | |
| 10,903,432 | B2 | 1/2021 | Sim et al. | |
| 11,393,991 | B2 | 7/2022 | Shin et al. | |
| 2008/0023724 | A1* | 1/2008 | Takeda | H10K 50/85 257/103 |
| 2012/0305894 | A1* | 12/2012 | Kim | C09K 11/06 257/E51.026 |
| 2015/0021590 | A1* | 1/2015 | Wu | H05B 33/10 546/4 |
| 2015/0243904 | A1* | 8/2015 | Lin | H10K 85/6572 548/440 |
| 2016/0072080 | A1* | 3/2016 | Jang | H10K 85/636 548/402 |
| 2017/0342057 | A1 | 11/2017 | Shim et al. | |
| 2018/0294421 | A1 | 10/2018 | Wolohan | |
| 2019/0044076 | A1* | 2/2019 | Shin | C07D 403/14 |
| 2019/0148640 | A1 | 5/2019 | Lim et al. | |
| 2020/0006674 | A1 | 1/2020 | Lin et al. | |
| 2021/0210700 | A1* | 7/2021 | Fleetham | H10K 85/6574 |

FOREIGN PATENT DOCUMENTS

| | | | |
|---|---|---|---|
| CN | 109384802 | A | 2/2019 |
| CN | 109786569 | A | 5/2019 |
| KR | 10-2010-0099327 | A | 9/2010 |
| KR | 10-2010-0118700 | A | 11/2010 |
| KR | 10-2015-0100493 | A | 9/2015 |
| KR | 10-2018-0114845 | A | 10/2018 |
| KR | 10-1922269 | B1 | 11/2018 |
| KR | 10-2019-0014300 | | 2/2019 |
| WO | WO 2016/116487 | A1 | 7/2016 |

* cited by examiner

30

40

HETEROCYCLIC COMPOUND, ORGANIC LIGHT-EMITTING DEVICE INCLUDING SAME

CROSS-REFERENCE TO RELATED APPLICATION

This application claims priority to and the benefit of Korean Patent Application No. 10-2020-0067861, filed on Jun. 4, 2020, in the Korean Intellectual Property Office, the entire content of which is hereby incorporated by reference.

BACKGROUND

1. Field

One or more embodiments of the present disclosure relate to a heterocyclic compound and an organic light-emitting device including the heterocyclic compound.

2. Description of Related Art

Organic light-emitting devices (OLEDs) are self-emissive devices that, as compared with other devices of the related art, have wide viewing angles, high contrast ratios, short response times, and excellent characteristics in terms of brightness, driving voltage, and response speed, and produce full-color images.

OLEDs may include a first electrode on a substrate, and a hole transport region, an emission layer, an electron transport region, and a second electrode sequentially stacked on the first electrode. Holes provided from the first electrode may move toward the emission layer through the hole transport region, and electrons provided from the second electrode may move toward the emission layer through the electron transport region. Carriers, such as holes and electrons, recombine in the emission layer to produce excitons. These excitons transit (e.g., transition or relax) from an excited state to a ground state to thereby generate light.

SUMMARY

One or more embodiments include a heterocyclic compound and an organic light-emitting device including the same.

Additional aspects of embodiments will be set forth in part in the description which follows and, in part, will be apparent from the description, or may be learned by practice of the presented embodiments of the disclosure.

According to one or more embodiments, a heterocyclic compound may be represented by Formula 1:

Formula 1

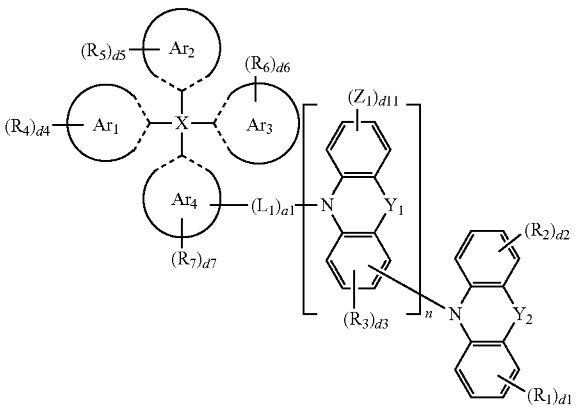

wherein, in Formula 1,

X may be a carbon group element except silicon (Si), rings $Ar_1$ to $Ar_4$, may each independently be a $C_5$-$C_{30}$ carbocyclic group or a $C_2$-$C_{30}$ heterocyclic group, $L_1$ may be selected from:

a single bond; and a benzene group, a naphthalene group, an anthracene group, a pyrene group, a fluorene group, a dibenzofuran group, and a dibenzothiophene group, each unsubstituted or substituted with at least one $Z_{10a}$, a1 may be an integer from 1 to 10, $Y_1$ and $Y_2$ may each independently be a single bond or a non-bond, n may be an integer from 1 to 5, $R_1$ to $R_7$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$Si(Q_1)(Q_2)(Q_3)$, —$N(Q_1)(Q_2)$, —$B(Q_1)(Q_2)$, —$C(=O)(Q_1)$, —$S(=O)_2(Q_1)$, and —$P(=O)(Q_1)(Q_2)$, $Z_1$ and $Z_{10a}$ may each be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, —$CD_3$, —$CD_2H$, —$CDH_2$, $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, and a naphthyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, and a cycloheptenyl group, unsubstituted or substituted with at least one selected from deuterium, —F, —Cl, —Br, —I, a hydroxyl group, a cyano group, a nitro group, an amidino group, a hydrazino group, a hydrazono group, $—CD_3$, $—CD_2H$, $—CDH_2$, $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, $—Si(Q_{41})(Q_{42})(Q_{43})$, $—N(Q_{41})(Q_{42})$, and $—B(Q_{41})(Q_{42})$; and $—Si(Q_{51})(Q_{52})(Q_{53})$, $—N(Q_{51})(Q_{52})$, and $—B(Q_{51})(Q_{52})$, wherein $Q_{41}$ to $Q_{43}$ and $Q_{51}$ to $Q_{53}$ may each independently be selected from:

$—CH_3$, $—CD_3$, $—CD_2H$, $—CDH_2$, $—CH_2CH_3$, $—CH_2CD_3$, $—CH_2CD_2H$, $—CH_2CDH_2$, $—CHDCH_3$, $—CHDCD_2H$, $—CHDCDH_2$, $—CHDCD_3$, $—CD_2CD_3$, $—CD_2CD_2H$, and $—CD_2CDH_2$; and an n-propyl group, an iso-propyl group, an n-butyl group, an isobutyl group, a sec-butyl group, a tert-butyl group, an n-pentyl group, an isopentyl group, a sec-pentyl group, and a tert-pentyl group, each unsubstituted or substituted with at least one selected from deuterium and a $C_1$-$C_{10}$ alkyl group, d1 and d2 may each be an integer from 1 to 4, d3 may be an integer from 1 to 3, d4 to d7 may each be an integer from 1 to 20, d11 may each be an integer from 1 to 4, a substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium (-D), —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, $—Si(Q_{11})(Q_{12})(Q_{13})$, $—N(Q_{11})(Q_{12})$, $—B(Q_{11})(Q_{12})$, $—C(=O)(Q_{11})$, $—S(=O)_2(Q_{11})$, and $—P(=O)(Q_{11})(Q_{12})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each unsubstituted or substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, $—Si(Q_{21})(Q_{22})(Q_{23})$, $—N(Q_{21})(Q_{22})$, $—B(Q_{21})(Q_{22})$, $—C(=O)(Q_{21})$, $—S(=O)_2(Q_{21})$, and $—P(=O)(Q_{21})(Q_{22})$; and $—Si(Q_{31})(Q_{32})(Q_{33})$, $—N(Q_{31})(Q_{32})$, $—B(Q_{31})(Q_{32})$, $—C(=O)(Q_{31})$, $—S(=O)_2(Q_{31})$, and $—P(=O)(Q_{31})(Q_{32})$, wherein $Q_1$ to $Q_3$, $Q_{11}$ to $Q_{13}$, $Q_{21}$ to $Q_{23}$, and $Q_{31}$ to $Q_{33}$ may each independently be selected from: hydrogen; deuterium; —F; —Cl; —Br; —I; a hydroxyl group; a cyano group; a nitro group; an amidino group; a hydrazino group; a hydrazono group; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{10}$ cycloalkyl group; a $C_1$-$C_{10}$ heterocycloalkyl group; a $C_3$-$C_{10}$ cycloalkenyl group; a $C_1$-$C_{10}$ heterocycloalkenyl group; a $C_6$-$C_{60}$ aryl group; a $C_1$-$C_{60}$ heteroaryl group; a monovalent non-aromatic condensed polycyclic group; a monovalent non-aromatic condensed heteropolycyclic group; a $C_1$-$C_{60}$ alkyl group substituted with at least one selected from deuterium, —F, and a cyano group; a $C_6$-$C_{60}$ aryl group substituted with at least one selected from deuterium, —F, and a cyano group; a biphenyl group; and a terphenyl group.

According to one or more embodiments, an organic light-emitting device may include: a first electrode; a second electrode facing the first electrode; an organic layer between the first electrode and the second electrode and including an emission layer; and at least one of the heterocyclic compound.

BRIEF DESCRIPTION OF THE DRAWINGS

The above and other aspects and features of certain embodiments of the disclosure will be more apparent from the following description taken in conjunction with the accompanying drawings, in which.

DETAILED DESCRIPTION

Figure 1:
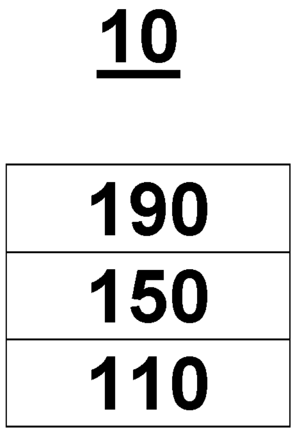
FIG. 1 is a schematic cross-sectional view of an embodiment of an organic light-emitting device.

Reference will now be made in more detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of embodiments of the present description. As used herein, the term "and/or" includes any and all combinations of one or more of the associated listed items. Throughout the disclosure, the expression "at least one of a, b or c" indicates only a, only b, only c, both a and b, both a and c, both b and c, all of a, b, and c, or variations thereof.

A heterocyclic compound represented by Formula 1:

Formula 1

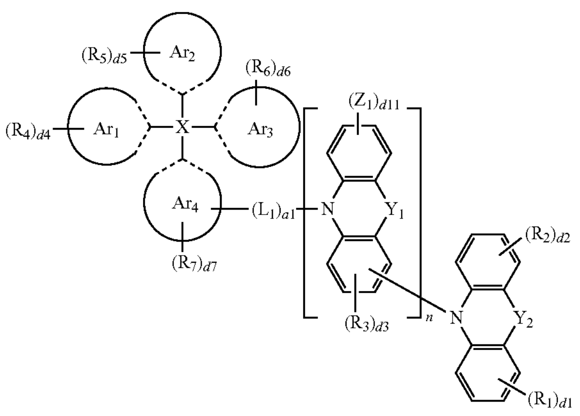

wherein, in Formula 1,

X may be a carbon group element except silicon (Si). For example, X may be a group 14 element, except that X does not include Si.

In an embodiment, X may be carbon (C), germanium (Ge), or tin (Sn).

Rings $Ar_1$ to $Ar_4$, may each independently be a $C_5$-$C_{30}$ carbocyclic group or a $C_2$-$C_{30}$ heterocyclic group.

In some embodiments, rings $Ar_1$ to $Ar_4$ may each independently be a benzene group, a naphthalene group, an anthracene group, a phenanthrene group, a triphenylene group, a pyrene group, a chrysene group, a cyclopentadiene group, a 1,2,3,4-tetrahydronaphthalene group, a thiophene group, a furan group, an indole group, a benzoborole group, a benzophosphole group, an indene group, a benzosilole group, a benzogermole group, a benzothiophene group, a benzoselenophene group, a benzofuran group, a carbazole group, a dibenzoborole group, a dibenzophosphole group, a fluorene group, a dibenzosilole group, a dibenzogermole group, a dibenzothiophene group, a dibenzoselenophene-group, a dibenzofuran group, a dibenzothiophene 5-oxide group, a 9H-fluorene-9-one group, a dibenzothiophene 5,5-dioxide group, an azaindole group, an azabenzoborole group, an azabenzophosphole group, an azaindene group, an azabenzosilole group, an azabenzogermole group, an azabenzothiophene group, an azabenzoselenophene group, an azabenzofuran group, an azacarbazole group, an azadibenzoborole group, an azadibenzophosphole group, an azafluorene group, an azadibenzosilole group, an azadibenzogermole group, an azadibenzothiophene group, an azadibenzoselenophene group, an azadibenzofuran group, an azadibenzothiophene 5-oxide group, an aza-9H-fluoren-9-one group, an azadibenzothiophene 5,5-dioxide group, a pyridine group, a pyrimidine group, a pyrazine group, a pyridazine group, a triazine group, a quinoline group, an isoquinoline group, a quinoxaline group, a quinazoline group, a phenanthroline group, a pyrrole group, a pyrazole group, an imidazole group, a triazole group, an oxazole group, an isooxazole group, a thiazole group, an isothiazole group, an oxadiazole group, a thiadiazole group, a benzopyrazole group, a benzimidazole group, a benzoxazole group, a benzothiazole group, a benzoxadiazole group, a benzothiadiazole group, a 5,6,7,8-tetrahydroisoquinoline group, or a 5,6,7,8-tetrahydroquinoline group.

In one or more embodiments, rings $Ar_1$ to $Ar_4$ may each independently be a benzene group, a naphthalene group, a fluorene group, a dibenzofuran group, or a dibenzothiophene group.

$L_1$ may be selected from:

a single bond; and a benzene group, a naphthalene group, an anthracene group, a pyrene group, a fluorene group, a dibenzofuran group, and a dibenzothiophene group, each unsubstituted or substituted with at least one $Z_{10a}$.

In some embodiments, *-$L_1$-*' may be a single bond; or a group represented by one of Formulae 4-1 to 4-9:

4-1

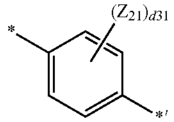

4-2

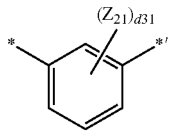

4-3

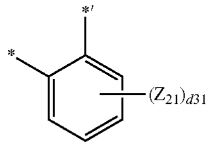

4-4

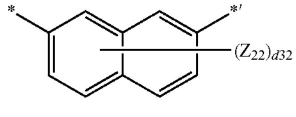

4-5

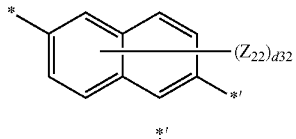

4-6

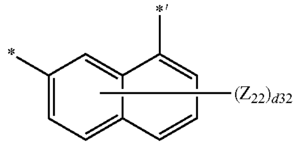

4-7

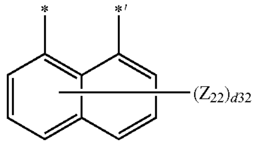

-continued 4-8

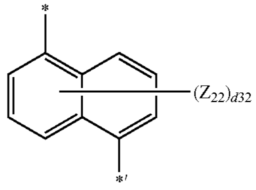

4-9

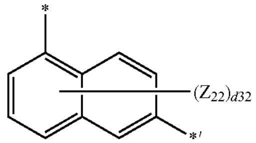

wherein, in Formulae 4-1 to 4-9, $Z_{21}$ and $Z_{22}$ may be the same as described with respect to $Z_{10a}$, d31 may be an integer from 1 to 4, d32 may be an integer from 1 to 6, and

* and *' each indicate a binding site to an adjacent atom.

a1 may be an integer from 1 to 10.

$Y_1$ and $Y_2$ may each independently be a single bond or a non-bond (e.g., $Y_1$ and $Y_2$ may each independently be a single bond or may be omitted so that the respective benzene rings are not connected to each other through $Y_1$ and $Y_2$ and the respective connection sites of the benzene rings are bonded to hydrogen or other substituents).

In some embodiments, $Y_1$ may be a single bond, and $Y_2$ may be a single bond;

$Y_1$ may be a non-bond (e.g., $Y_1$ may be omitted so that the respective benzene rings are not connected to each other through $Y_1$ and the respective connection sites of the benzene rings are bonded to hydrogen or other substituents), and $Y_2$ may be a single bond;

$Y_1$ may be a single bond, and $Y_2$ may be a non-bond; or $Y_1$ may be a non-bond (e.g., $Y_2$ may be omitted so that the respective benzene rings are not connected to each other through $Y_2$ and the respective connection sites of the benzene rings are bonded to hydrogen or other substituents), and $Y_2$ may be a non-bond (e.g., $Y_1$ may be omitted so that the respective benzene rings are not connected to each other through $Y_1$ and the respective connection sites of the benzene rings are bonded to hydrogen or other substituents).

In some embodiments, $Y_1$ may be a single bond, and $Y_2$ may be a single bond.

n may be an integer from 1 to 5.

In some embodiments, n may be 2 or greater.

$R_1$ to $R_7$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$Si(Q_1)(Q_2)(Q_3)$, —$N(Q_1)(Q_2)$, —$B(Q_1)(Q_2)$, —$C(=O)(Q_1)$, —$S(=O)_2(Q_1)$, and —$P(=O)(Q_1)(Q_2)$.

A substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium (-D), —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, and —$P(=O)(Q_{11})(Q_{12})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each unsubstituted or substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{21})(Q_{22})(Q_{23})$, —$N(Q_{21})(Q_{22})$, —$B(Q_{21})(Q_{22})$, —$C(=O)(Q_{21})$, —$S(=O)_2(Q_{21})$, and —$P(=O)(Q_{21})(Q_{22})$; and —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, and —$P(=O)(Q_{31})(Q_{32})$, wherein $Q_1$ to $Q_3$, $Q_{11}$ to $Q_{13}$, $Q_{21}$ to $Q_{23}$, and $Q_{31}$ to $Q_{33}$ may each independently be selected from: hydrogen; deuterium; —F; —Cl; —Br; —I; a hydroxyl group; a cyano group; a nitro group; an amidino group; a hydrazino group; a hydrazono group; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{10}$ cycloalkyl group; a $C_1$-$C_{10}$ heterocycloalkyl group; a $C_3$-$C_{10}$ cycloalkenyl group; a $C_1$-$C_{10}$ heterocycloalkenyl group; a $C_6$-$C_{60}$ aryl group; a $C_1$-$C_{60}$ heteroaryl group; a monovalent non-aromatic condensed polycyclic group; a monovalent non-aromatic condensed heteropolycyclic group; a $C_1$-$C_{60}$ alkyl group substituted with at least one selected from deuterium, —F, and a cyano group; a $C_6$-$C_{60}$ aryl group substituted with at least one selected from deuterium, —F, and a cyano group; a biphenyl group; and a terphenyl group.

In some embodiments, $R_1$ to $R_7$ may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, $—CD_3$, $—CD_2H$, $—CDH_2$, $—CF_3$, $—CF_2H$, $—CFH_2$, a hydroxyl group, a cyano group, a nitro group, an amidino group, a hydrazino group, a hydrazono group, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a naphthyl group, a pyridinyl group, and a pyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a $C_1$-$C_{10}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, an azacarbazolyl group, an azadibenzofuranyl group, an azadibenzothiophenyl group, an azafluorenyl group, and an azadibenzosilolyl group, each substituted with at least one selected from deuterium, —F, —Cl, —Br, —I, $—CD_3$, $—CD_2H$, $—CDH_2$, $—CF_3$, $—CF_2H$, $—CFH_2$, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a $C_1$-$C_{10}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, $—Si(Q_{31})(Q_{32})(Q_{33})$, $—N(Q_{31})(Q_{32})$, $—B(Q_{31})(Q_{32})$, $—P(Q_{31})(Q_{32})$, $—C(=O)(Q_{31})$, $—S(=O)_2(Q_{31})$, and $—P(=O)(Q_{31})(Q_{32})$;

$—Si(Q_1)(Q_2)(Q_3)$, $—N(Q_1)(Q_2)$, $—B(Q_1)(Q_2)$, $—C(=O)(Q_1)$, $—S(=O)_2(Q_1)$, and $—P(=O)(Q_1)(Q_2)$; and a group represented by Formula 2-1:

2-1

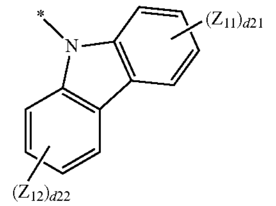

wherein, in Formula 2-1, $Z_{11}$ and $Z_{12}$ may each be understood by referring to the description of $Z_1$ provided herein, d21 and d22 may each independently be an integer from 1 to 4, wherein $Q_1$ to $Q_3$ and $Q_{31}$ to $Q_{33}$ may each independently be selected from:

$—CH_3$, $—CD_3$, $—CD_2H$, $—CDH_2$, $—CH_2CH_3$, $—CH_2CD_3$, $—CH_2CD_2H$, $—CH_2CDH_2$, $—CHDCH_3$, $—CHDCD_2H$, $—CHDCDH_2$, $—CHDCD_3$, $—CD_2CD_3$, $—CD_2CD_2H$, and $—CD_2CDH_2$; and an n-propyl group, an iso-propyl group, an n-butyl group, an isobutyl group, a sec-butyl group, a tert-butyl group, an n-pentyl group, an isopentyl group, a sec-pentyl group, a tert-pentyl group, a phenyl group, a naphthyl group, a pyridinyl group, a pyrimidinyl group, a pyridazinyl group, a pyrazinyl group, and a triazinyl group, each unsubstituted or substituted with at least one selected from deuterium, a $C_1$-$C_{10}$ alkyl group, a phenyl group, a biphenyl group, a pyridinyl group, a pyrimidinyl group, a pyridazinyl group, a pyrazinyl group, and a triazinyl group.

$R_1$ to $R_7$ may each independently be selected from:

hydrogen, deuterium, a cyano group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, $—CD_3$, $—CD_2H$, $—CDH_2$, $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, and a naphthyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a $C_1$-$C_{10}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an isoindolyl group, an indolyl group, an indazolyl group, a purinyl group, a carbazolyl group, a benzofuranyl group, a benzothiophenyl group, a dibenzofuranyl group, a dibenzothiophenyl group, a benzocarbazolyl group, and a dibenzocarbazolyl group, each unsubstituted or substituted with at least one selected from deuterium, $—CD_3$, $—CD_2H$, $—CDH_2$, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a $C_1$-$C_{10}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an isoindolyl group, an indolyl group, an indazolyl group, a purinyl group, a carbazolyl group, a benzofuranyl group, a benzothiophenyl group, a dibenzofuranyl group, a dibenzothiophenyl group, a benzocarbazolyl group, a dibenzocarbazolyl group, $—Si(Q_{31})(Q_{32})(Q_{33})$, and $—N(Q_{31})(Q_{32})$, $—B(Q_{31})(Q_{32})$;

$—Si(Q_1)(Q_2)(Q_3)$, $—N(Q_1)(Q_2)$, and $—B(Q_1)(Q_2)$; and a group represented by Formula 2-1:

2-1

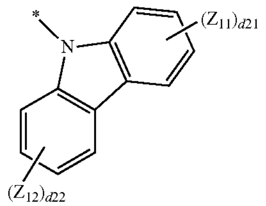

wherein, in Formula 2-1, $Z_{11}$ and $Z_{12}$ may each be understood by referring to the description of $Z_1$ provided herein, d21 and d22 may each independently be an integer from 1 to 4,

* indicates a binding site to an adjacent atom, and wherein $Q_1$ to $Q_3$ and $Q_{31}$ to $Q_{33}$ may each independently be selected from:

$—CH_3$, $—CD_3$, $—CD_2H$, $—CDH_2$, $—CH_2CH_3$, $—CH_2CD_3$, $—CH_2CD_2H$, $—CH_2CDH_2$, $—CHDCH_3$, $—CHDCD_2H$, $—CHDCDH_2$, $—CHDCD_3$, $—CD_2CD_3$, $—CD_2CD_2H$, and $—CD_2CDH_2$; and an n-propyl group, an iso-propyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group, each unsubstituted or substituted with at least one selected from deuterium, a $C_1$-$C_{10}$ alkyl group, a phenyl group, and a biphenyl group.

$Z_1$ and $Z_{10a}$ may each be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, $—CD_3$, $—CD_2H$, $—CDH_2$, $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, and a naphthyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, and a cycloheptenyl group, unsubstituted or substituted with at least one selected from deuterium, —F, —Cl, —Br, —I, a hydroxyl group, a cyano group, a nitro group, an amidino group, a hydrazino group, a hydrazono group, $—CD_3$, $—CD_2H$, $—CDH_2$, $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, $—Si(Q_{41})(Q_{42})(Q_{43})$, $—N(Q_{41})(Q_{42})$, and $—B(Q_{41})(Q_{42})$; and $—Si(Q_{51})(Q_{52})(Q_{53})$, $—N(Q_{51})(Q_{52})$, and $—B(Q_{51})(Q_{52})$, wherein $Q_{41}$ to $Q_{43}$ and $Q_{51}$ to $Q_{53}$ may each independently be selected from:

$—CH_3$, $—CD_3$, $—CD_2H$, $—CDH_2$, $—CH_2CH_3$, $—CH_2CD_3$, $—CH_2CD_2H$, $—CH_2CDH_2$, $—CHDCH_3$, $—CHDCD_2H$, $—CHDCDH_2$, $—CHDCD_3$, $—CD_2CD_3$, $—CD_2CD_2H$, and $—CD_2CDH_2$; and an n-propyl group, an iso-propyl group, an n-butyl group, an isobutyl group, a sec-butyl group, a tert-butyl group, an n-pentyl group, an isopentyl group, a sec-pentyl group, and a tert-pentyl group, each unsubstituted or substituted with at least one selected from deuterium and a $C_1$-$C_{10}$ alkyl group.

d1 and d2 may each be an integer from 1 to 4, d3 be an integer from 1 to 3, d4 to d7 may each be an integer from 1 to 20, and d11 may be an integer from 1 to 4.

In some embodiments, the heterocyclic compound represented by Formula 1 may be represented by Formula 1-1:

Formula 1-1

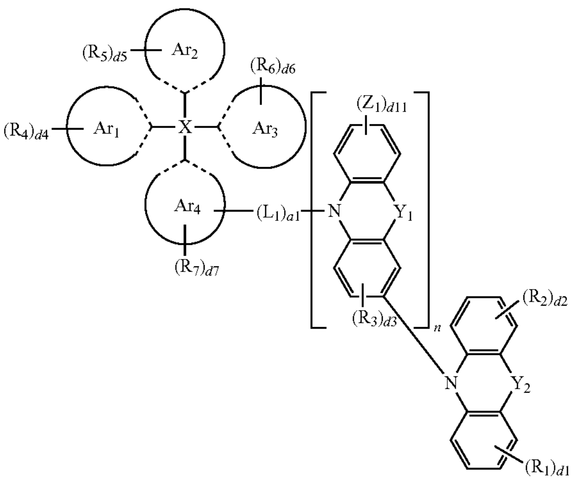

wherein, in Formula 1-1, X, ring $Ar_1$ to $Ar_4$, $L_1$, a1, $Y_1$, $Y_2$, n, $R_1$ to $R_7$, $Z_1$, d1 to d7, and d11 may respectively be understood by referring to the descriptions of X, ring $Ar_1$ to $Ar_4$, $L_1$, a1, $Y_1$, $Y_2$, n, $R_1$ to $R_7$, $Z_1$, d1 to d7, and d11 provided elsewhere herein.

In some embodiments, a portion represented by

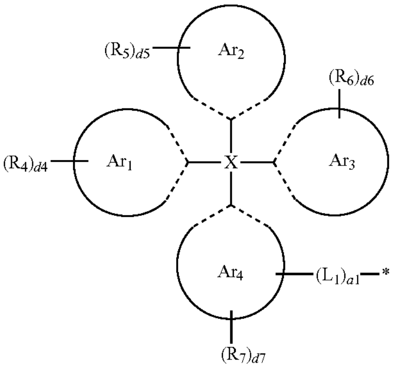

in Formula 1 may be represented by one of Formulae 3-1 to 3-3:

3-1

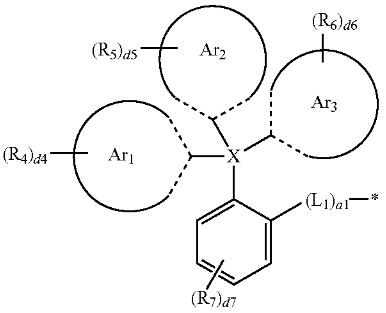

-continued 3-2

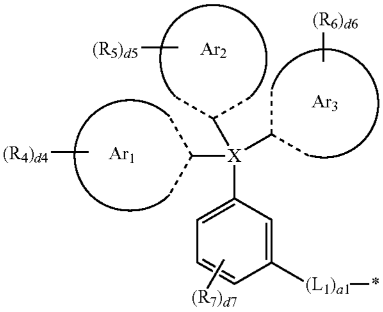

3-3

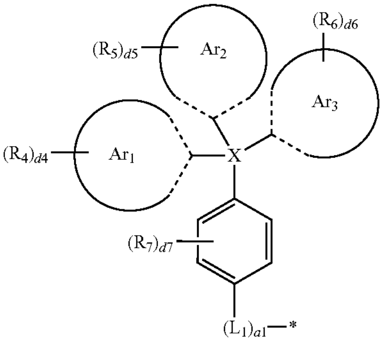

wherein, in Formulae 3-1 to 3-3, d7 may be an integer from 1 to 4, X, ring $Ar_1$ to $Ar_3$, $L_1$, a1, $R_4$ to $R_7$, and d4 to d7 may respectively be understood by referring to the descriptions of X, ring $Ar_1$ to $Ar_3$, $L_1$, a1, $R_4$ to $R_7$, and d4 to d7 provided herein, and * indicates a binding site to an adjacent atom.

In an embodiment, a portion represented by

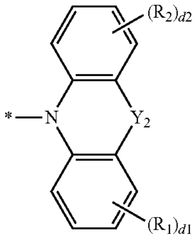

in Formula 1 may be represented by one of Formulae 5-1 to 5-36:

5-1

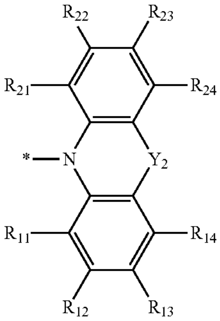

-continued
5-2
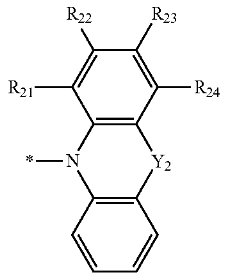
5-3
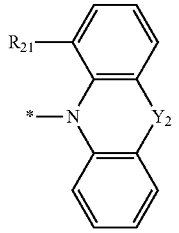
5-4
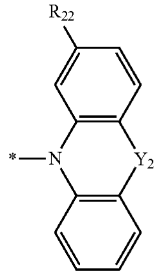
5-5
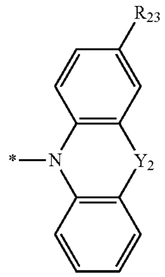
5-6
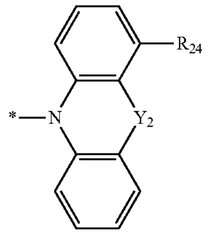
5-7
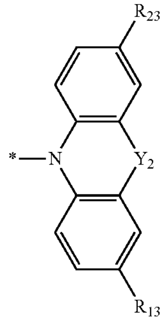
-continued
5-8
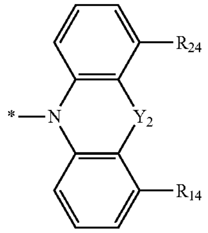
5-9
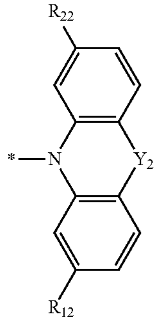
5-10
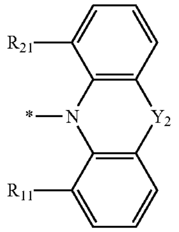
5-11
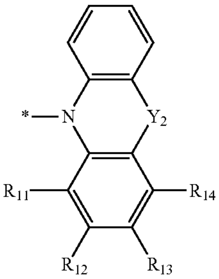
5-12
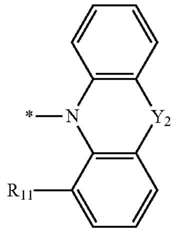
5-13
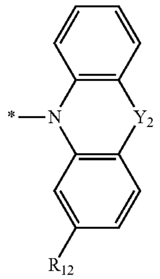

-continued
5-14
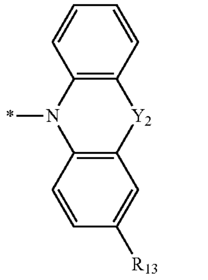
5-15
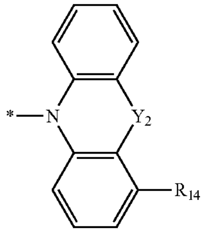
5-16
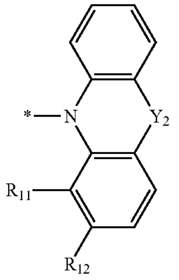
5-17
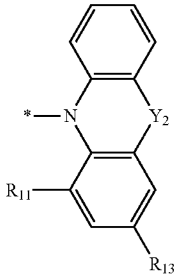
5-18
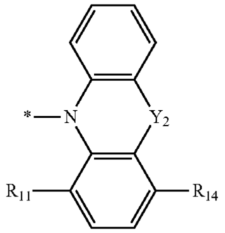
5-19
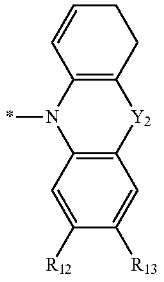
-continued
5-20
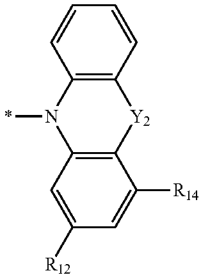
5-21
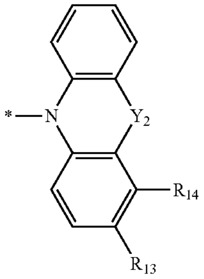
5-22
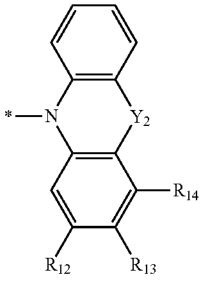
5-23
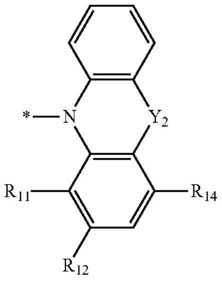
5-24
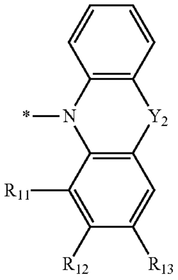

-continued
5-25
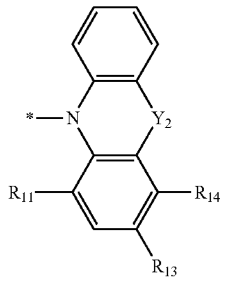
5-26
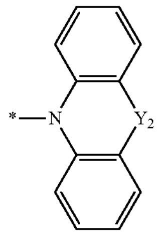
5-27
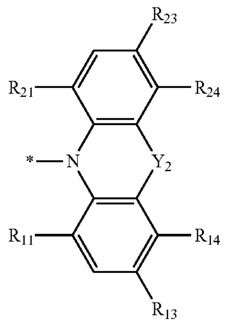
5-28
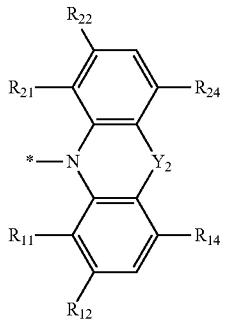
5-29
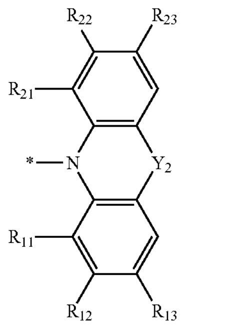
-continued
5-30
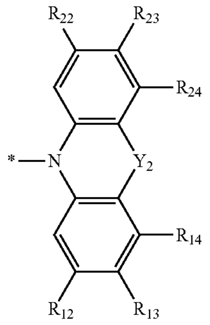
5-31
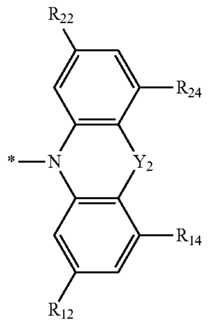
5-32
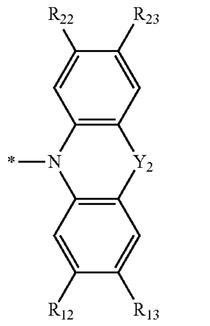
5-33
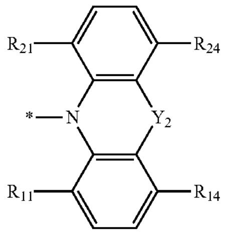
5-34
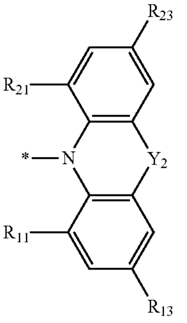

-continued 5-35

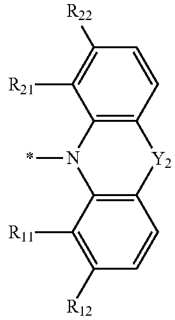

5-36

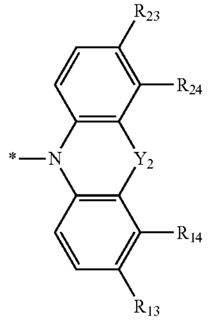

wherein, in Formulae 5-1 to 5-36, $Y_2$ may be understood by referring to the description of $Y_2$ provided herein, and $R_{11}$ to $R_{14}$ may each be understood by referring to the description of $R_1$ provided herein, and $R_{21}$ to $R_{24}$ may each be understood by referring to the description of $R_2$ provided herein, provided that $R_{11}$ to $R_{14}$ and $R_{21}$ to $R_{24}$ may not each be hydrogen.

In some embodiments, $R_4$ to $R_7$ may not each be hydrogen;

$R_7$ may be hydrogen, and at least one of $R_4$ to $R_6$ may not each be hydrogen; or $R_4$ to $R_6$ may each be hydrogen, and $R_7$ may not be hydrogen.

In some embodiments, the heterocyclic compound represented by Formula 1 may be represented by one of Formulae 6-1 to 6-4:

Formula 6-1

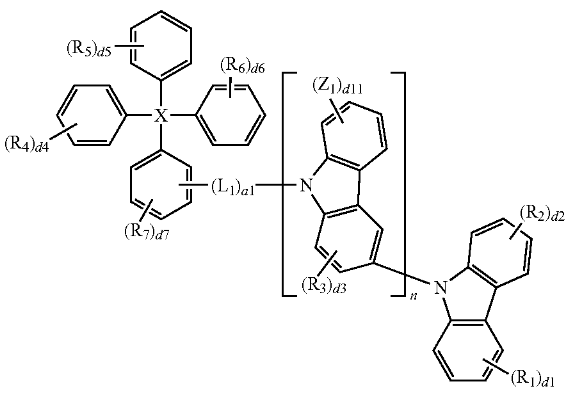

-continued

Formula 6-2

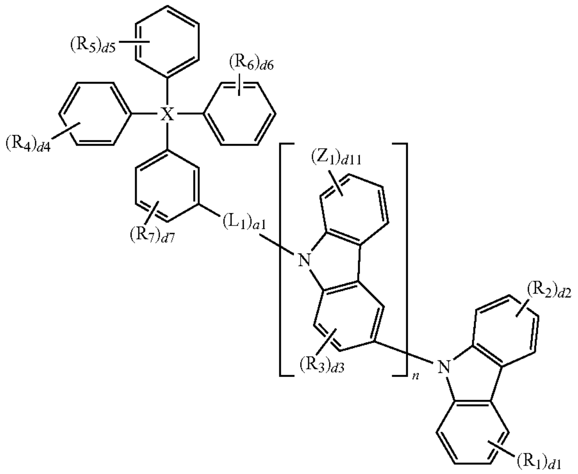

Formula 6-3

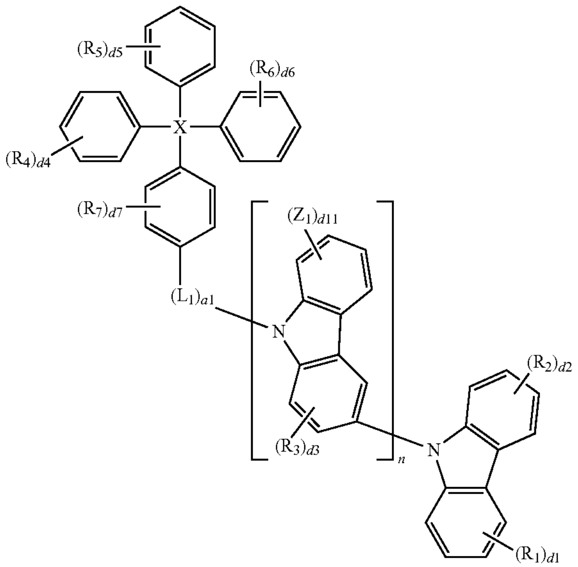

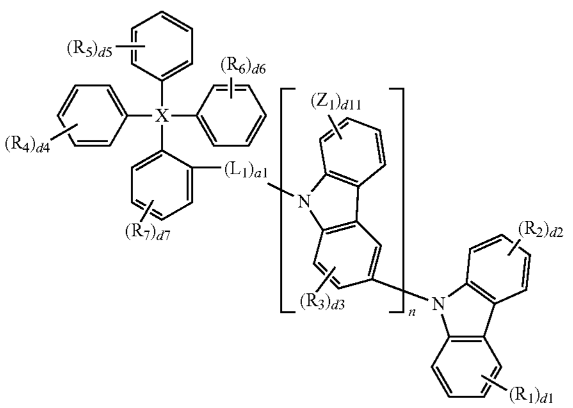

wherein, in Formulae 6-1 and 6-4, $L_1$, a1, n, $R_1$ to $R_7$, and $Z_1$ may respectively be understood by referring to the descriptions of $L_1$, a1, n, $R_1$ to $R_7$, and $Z_1$ provided herein, d1, d2, d7, and d11 may each independently be an integer from 1 to 4, d3 may be an integer from 1 to 3, and d4 to d6 may each independently be an integer from 1 to 5.

In some embodiments, the heterocyclic compound may be selected from Compounds 1 to 80, but embodiments are not limited thereto:

1

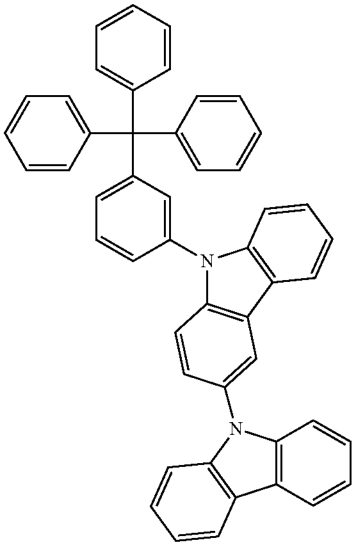

2

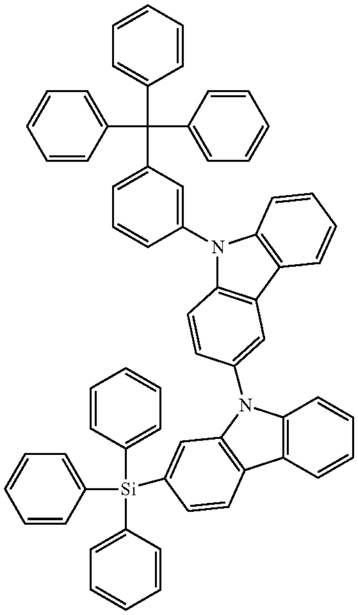

-continued

3

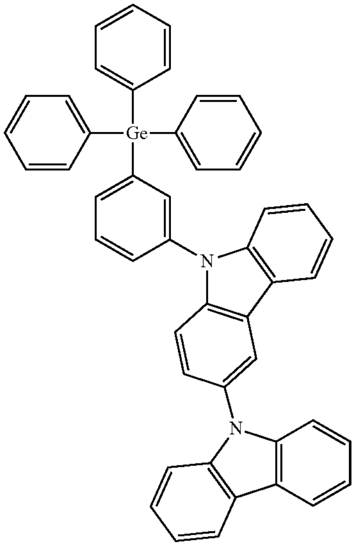

4

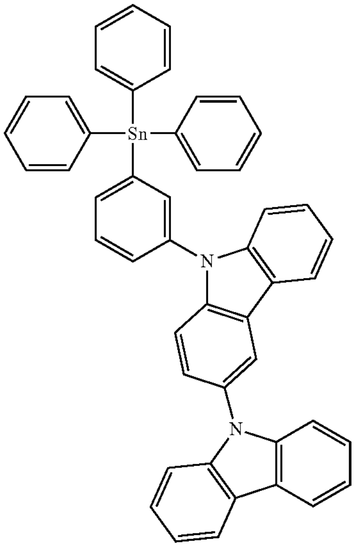

-continued
5
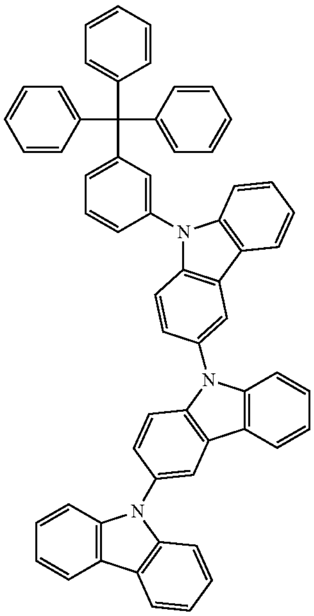
6
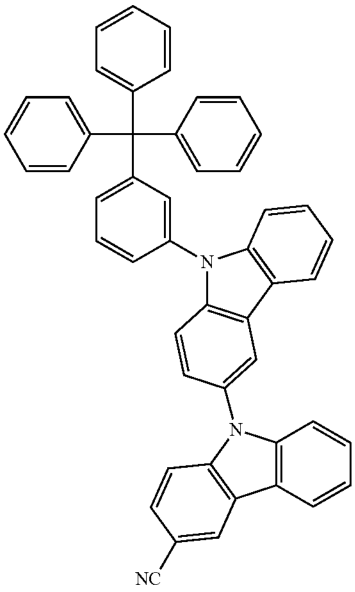
-continued
7
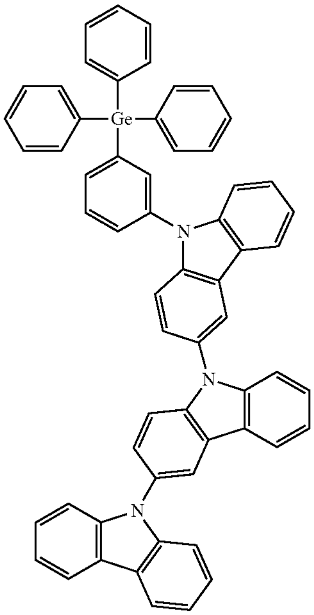
8
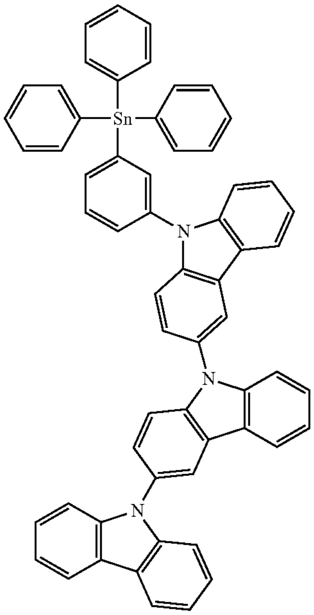

-continued
9
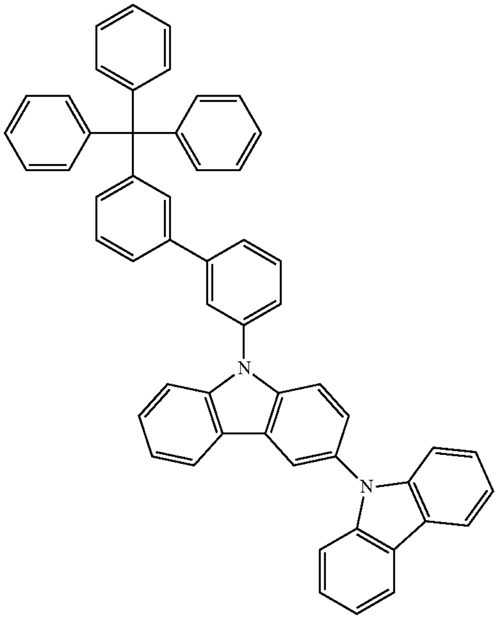
10
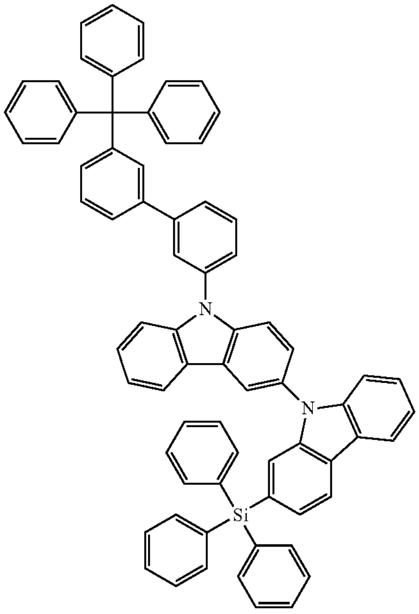
-continued
11
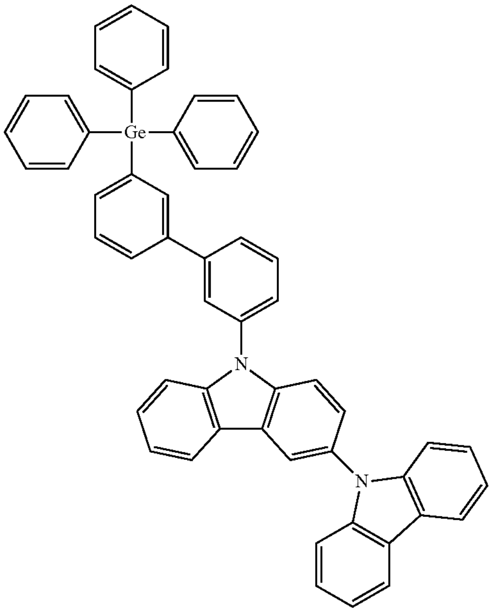
12
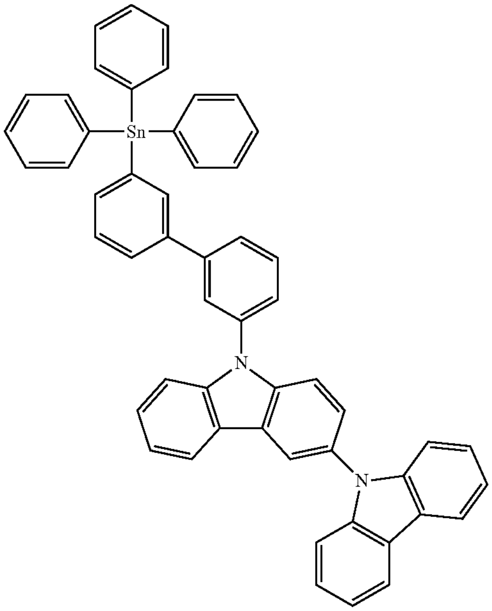

-continued
13
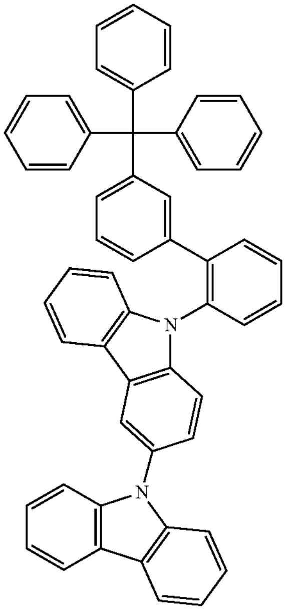
14
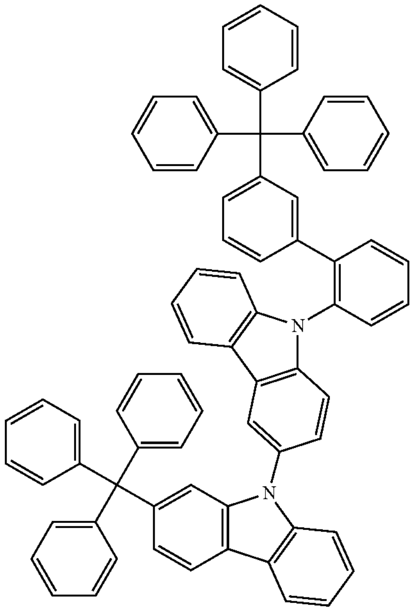
-continued
15
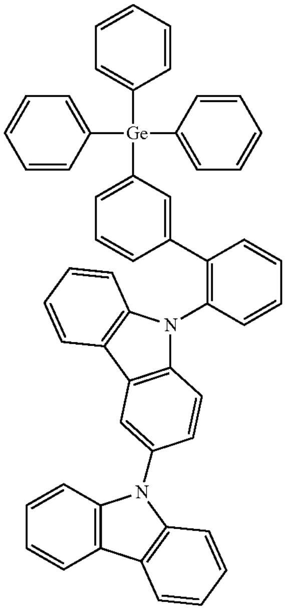
16
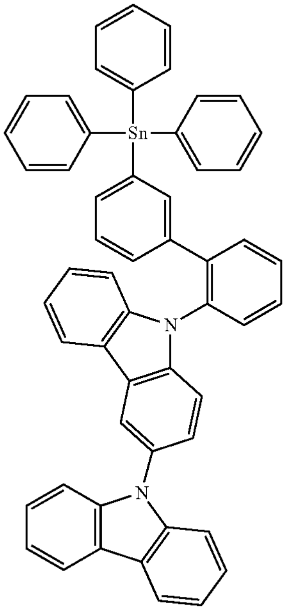

17
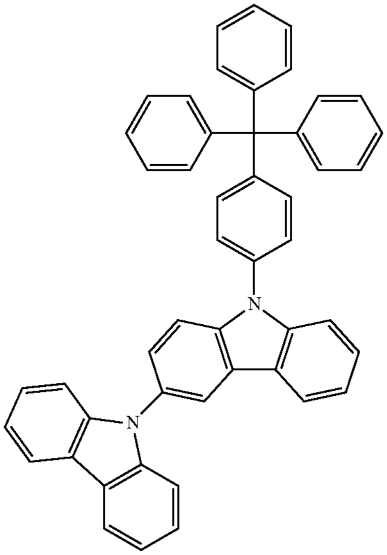
18
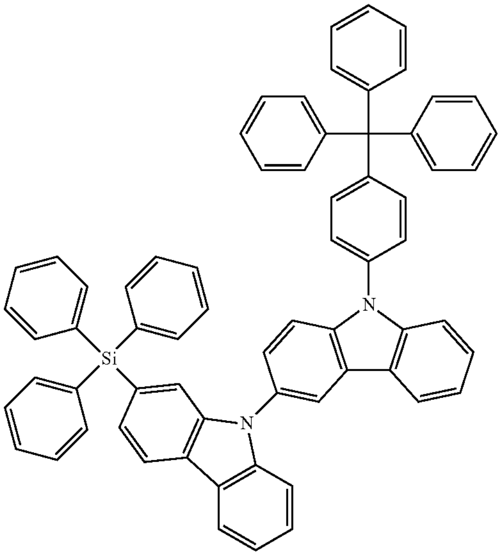
19
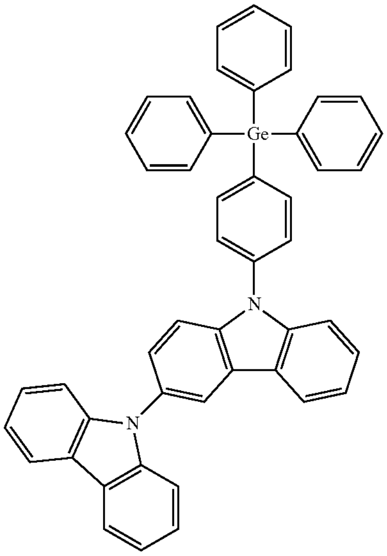
20
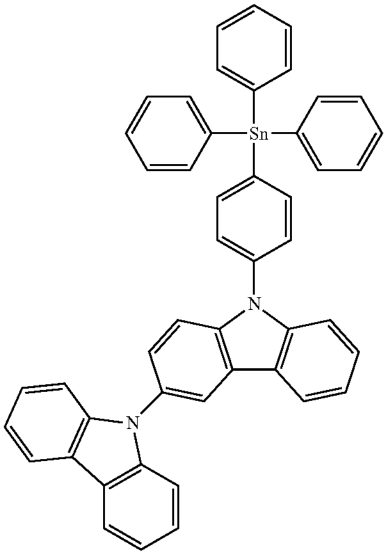

-continued
21
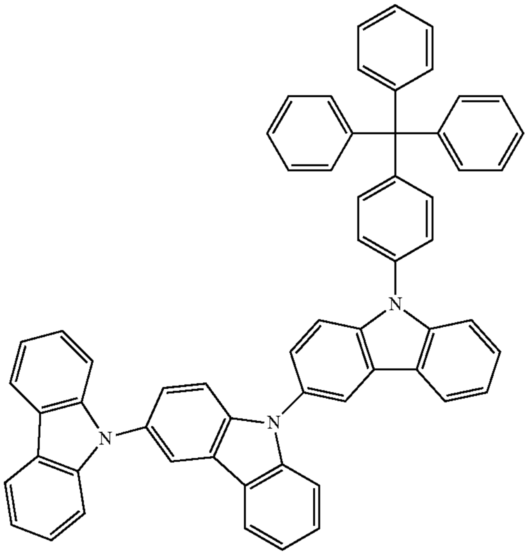
22
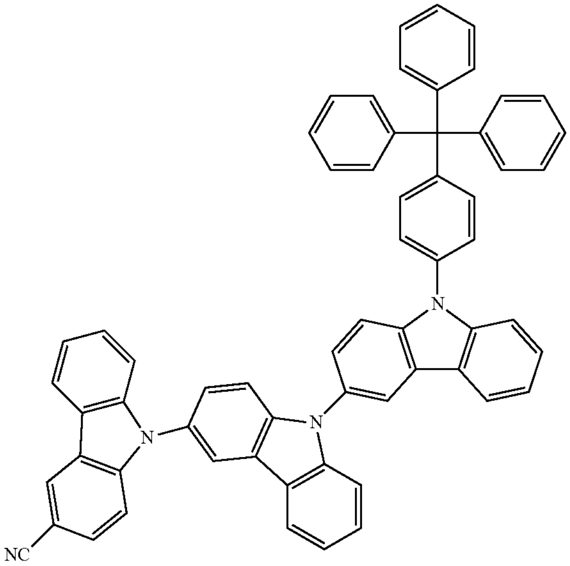
-continued
23
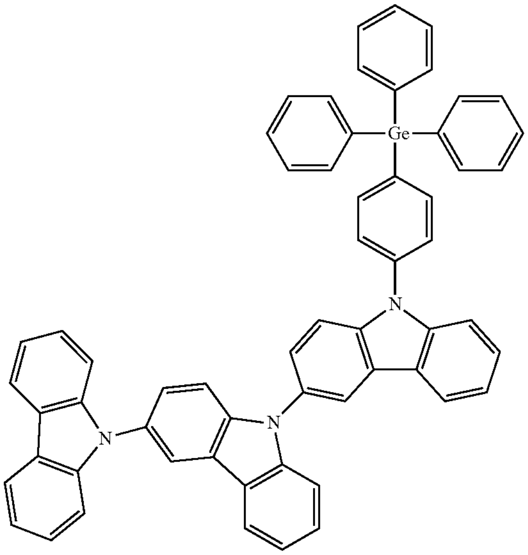
24
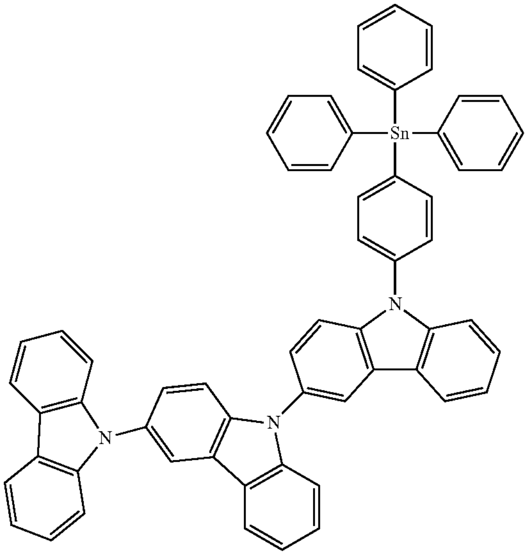

-continued
25
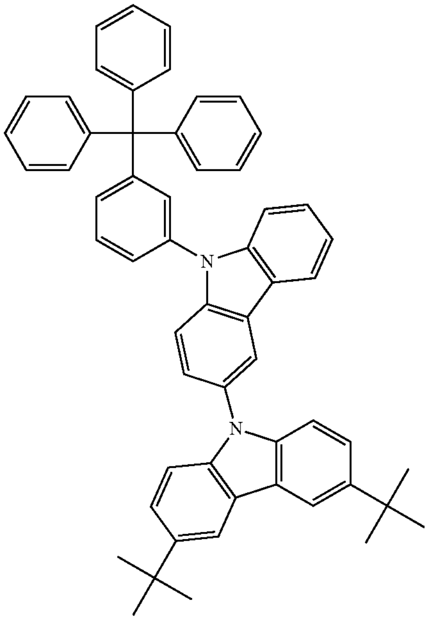
26
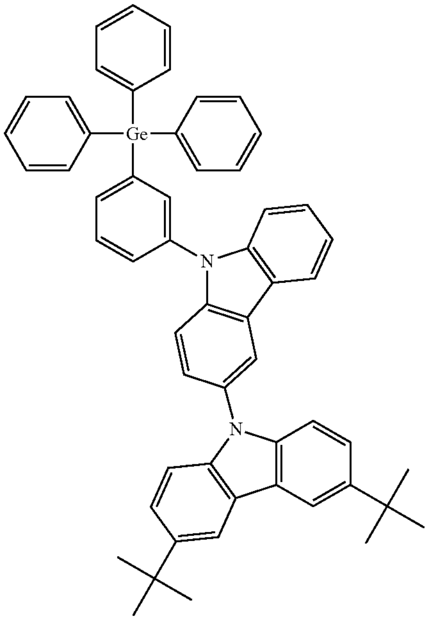
-continued
27
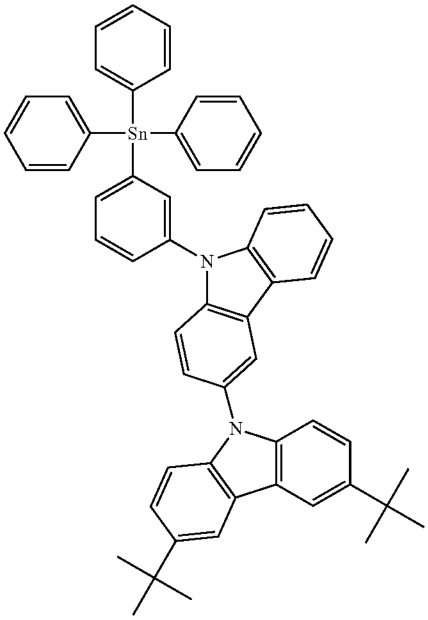
28
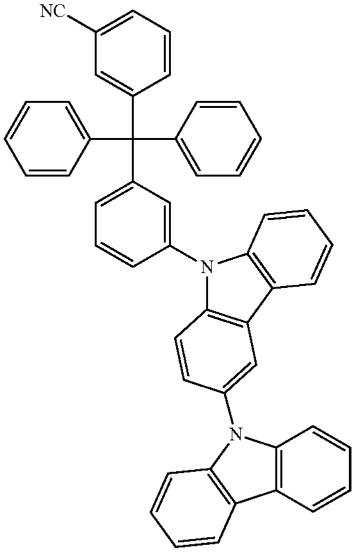

-continued
29
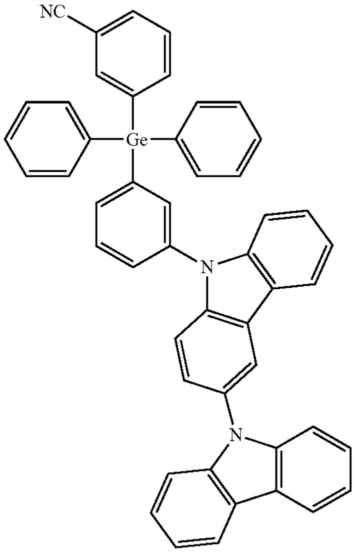
30
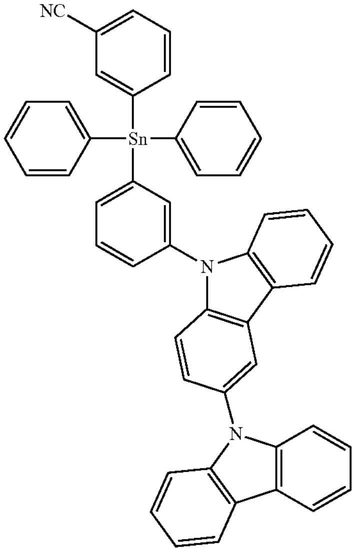
-continued
31
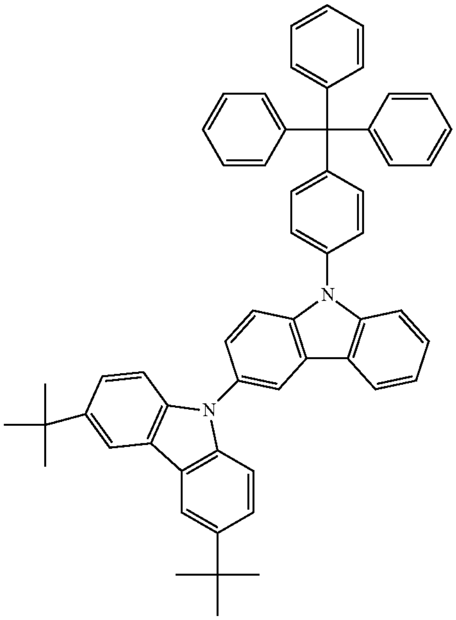
32
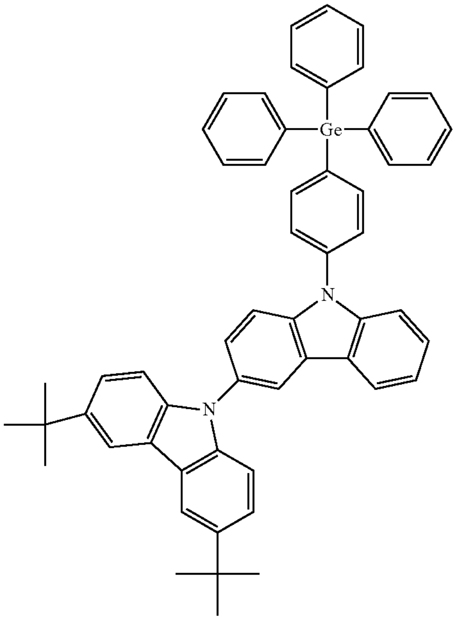

-continued
33
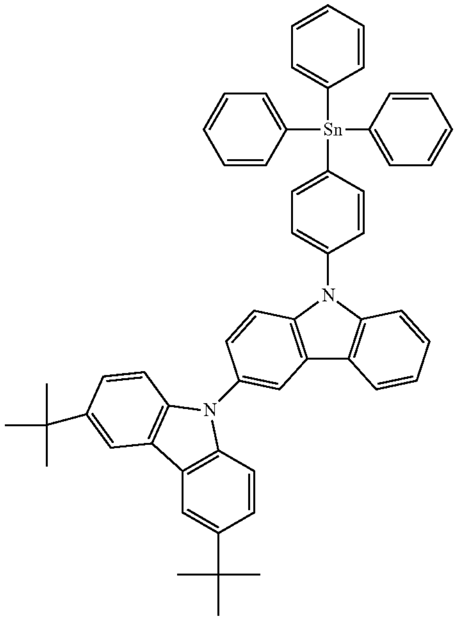
-continued
35
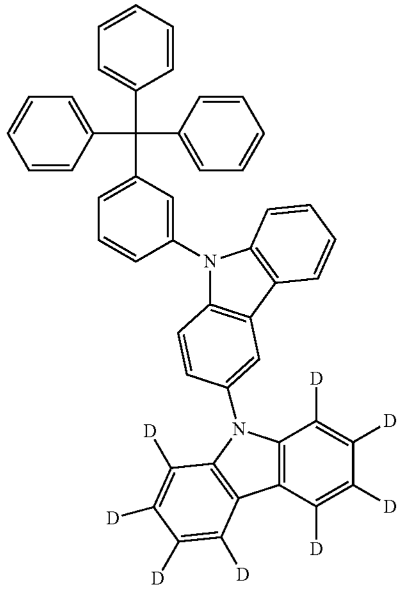
34
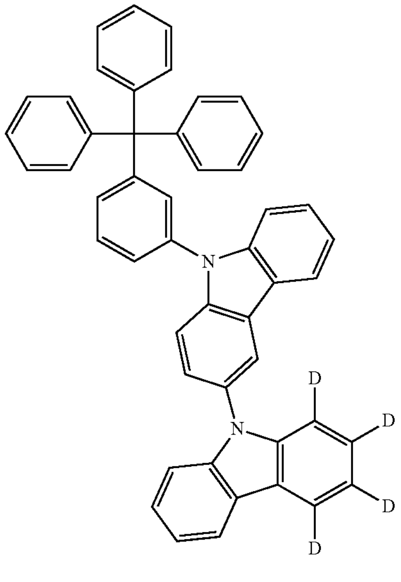
36
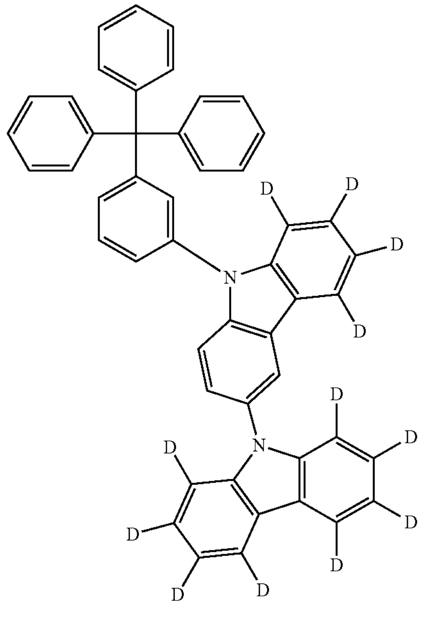

-continued
37
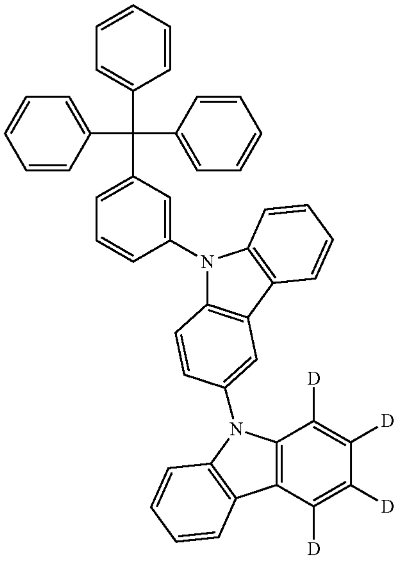
38
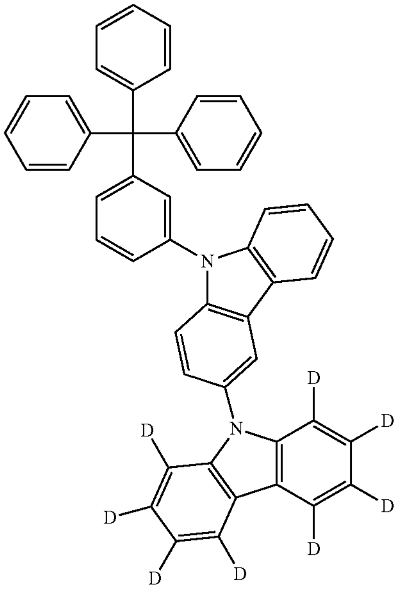
-continued
39
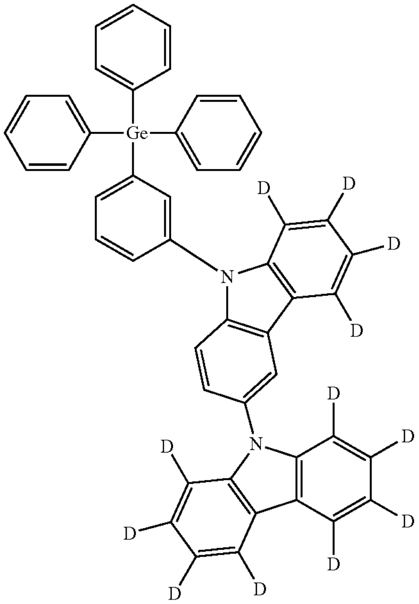
40
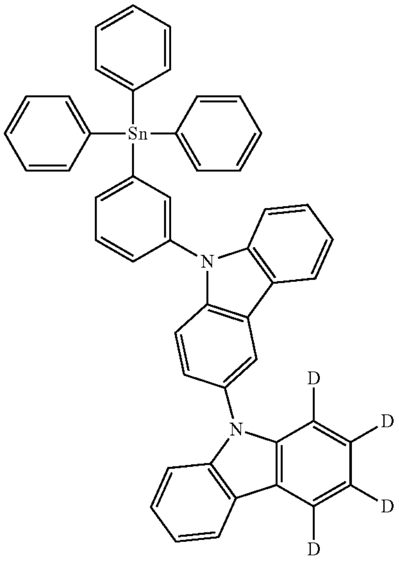

-continued
41
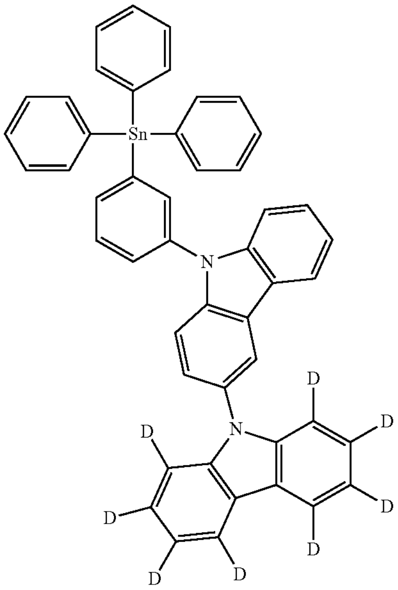
42
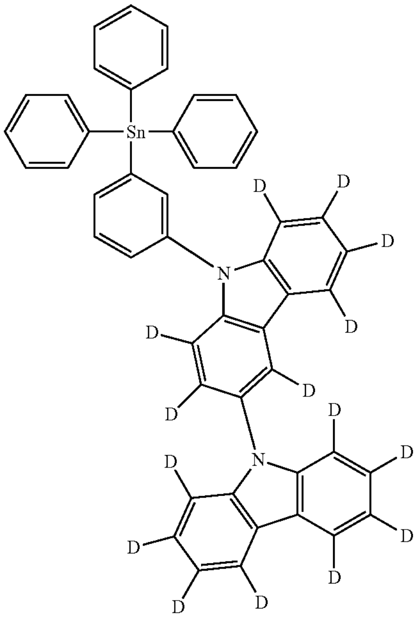
-continued
43
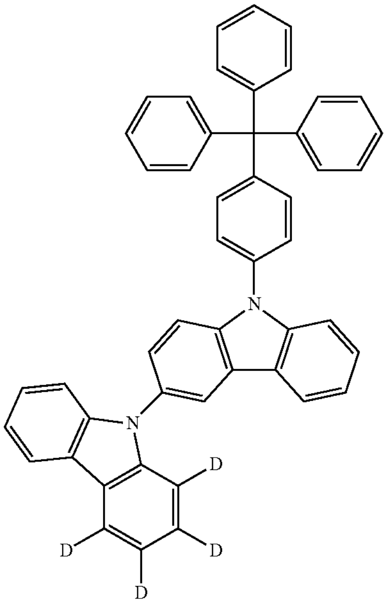
44
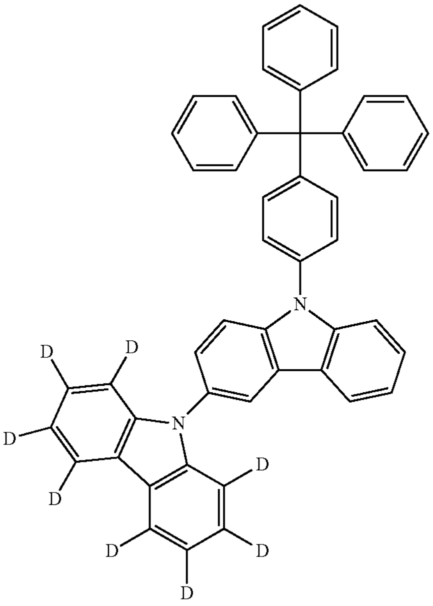

-continued
45
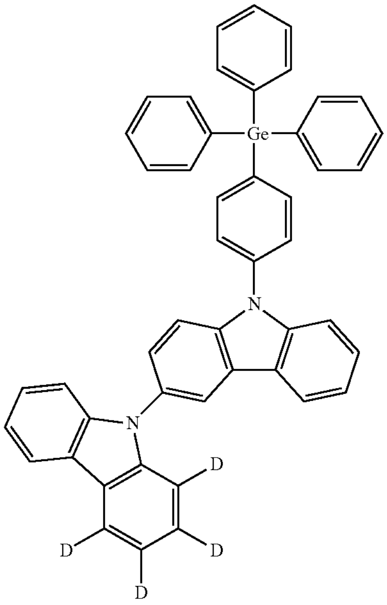
46
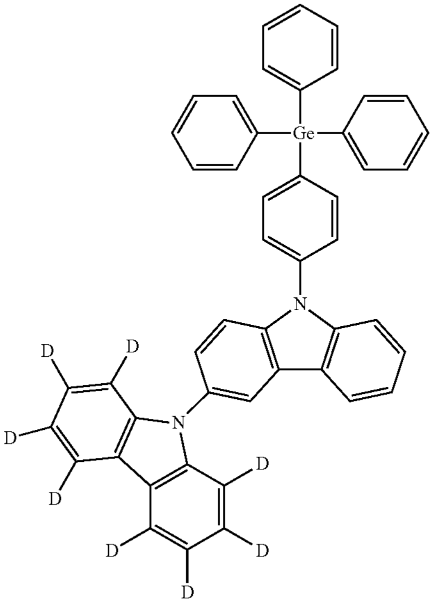
-continued
47
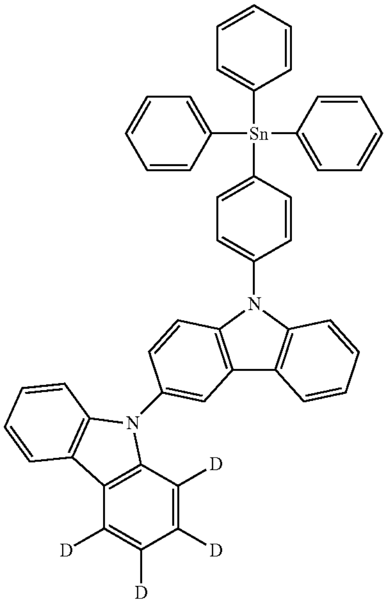
48
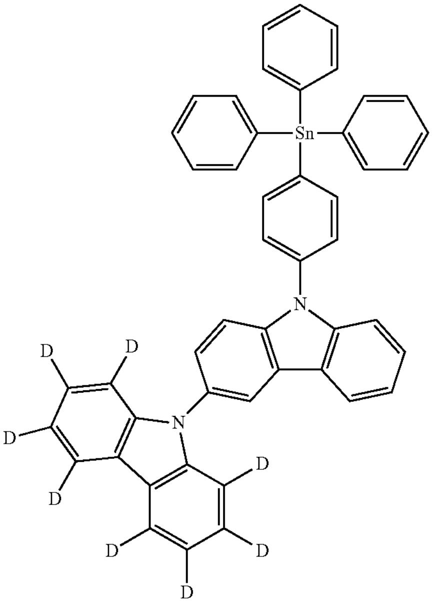

-continued
49
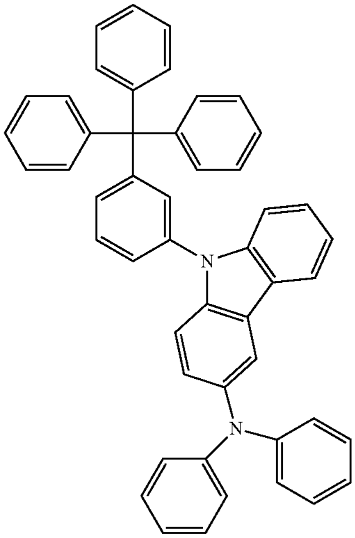
50
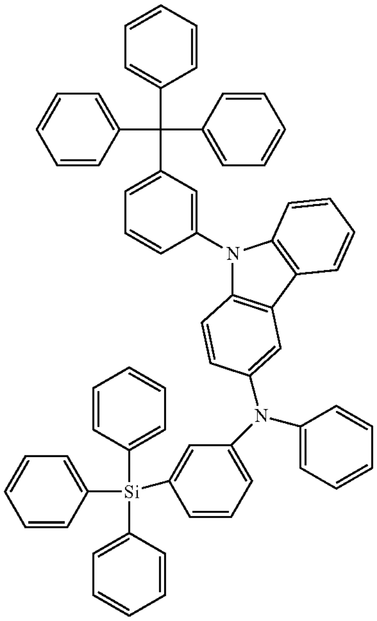
-continued
51
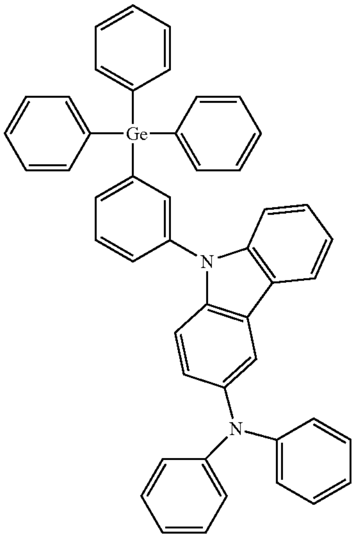
52
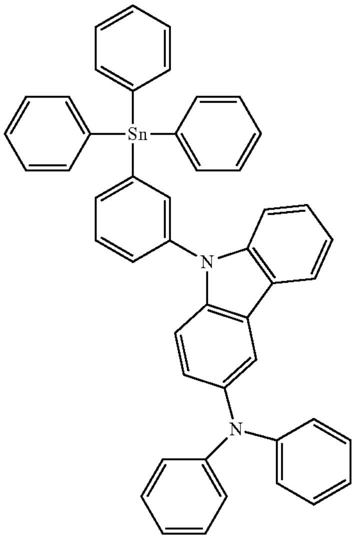
53
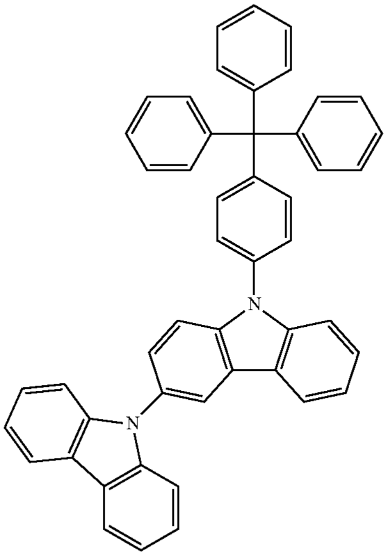

-continued
54
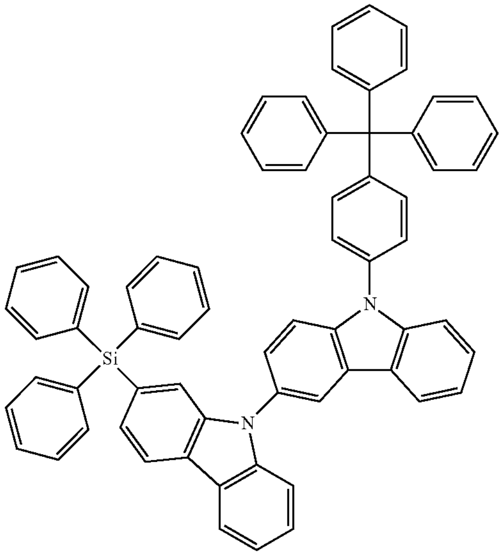
-continued
56
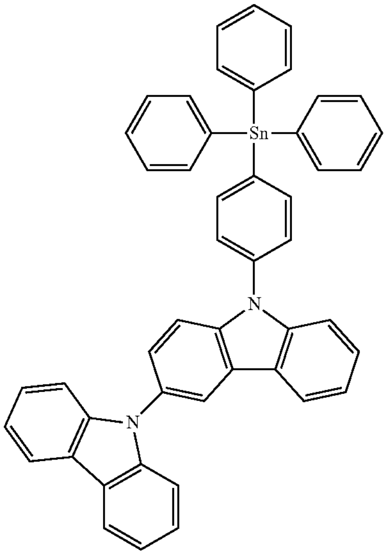
55
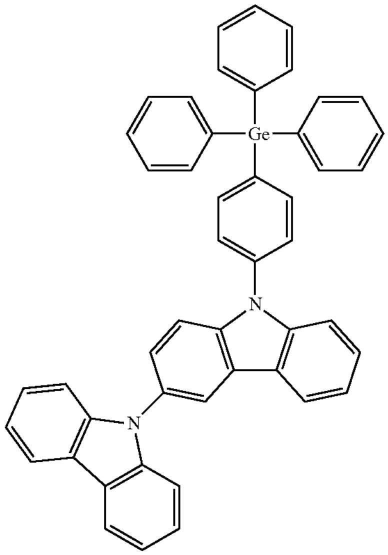
57
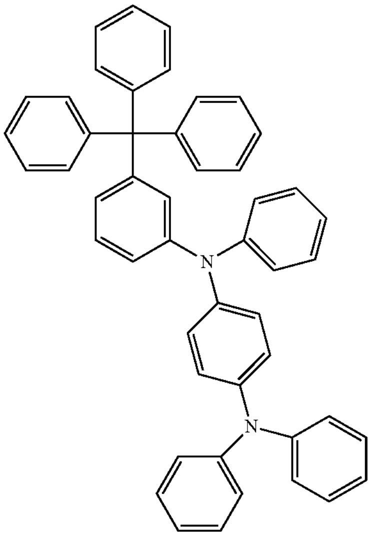

-continued
58
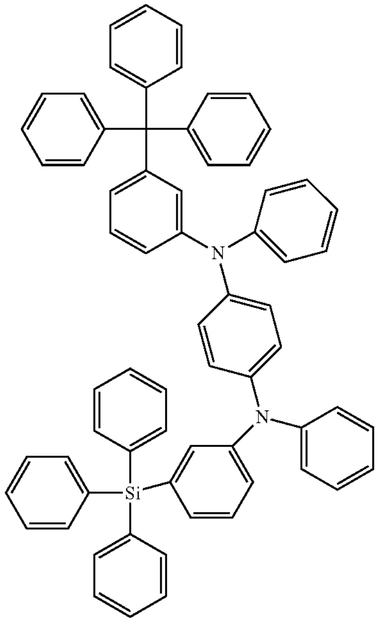
59
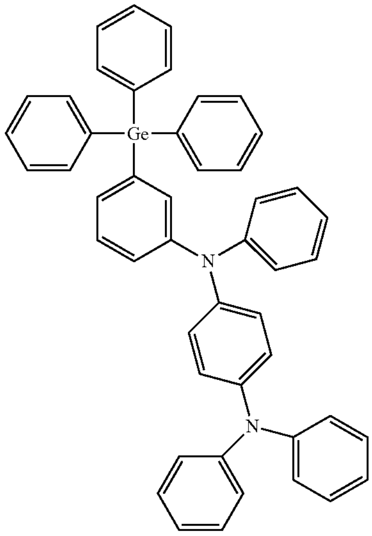
-continued
60
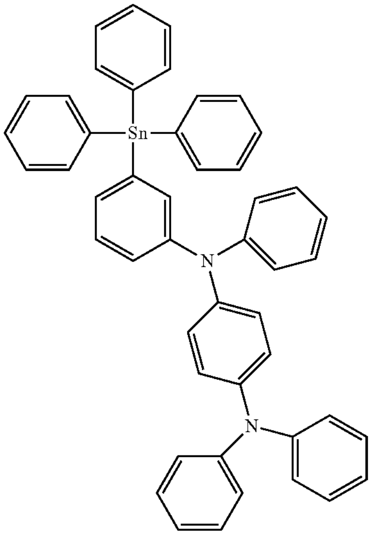
61
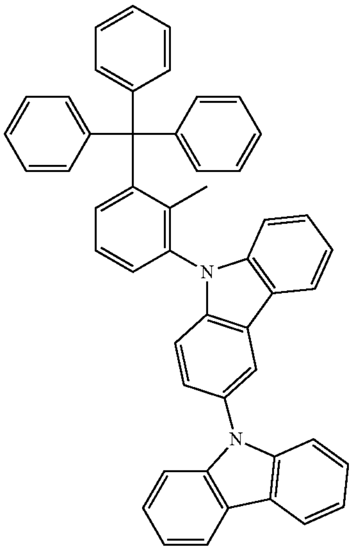
62
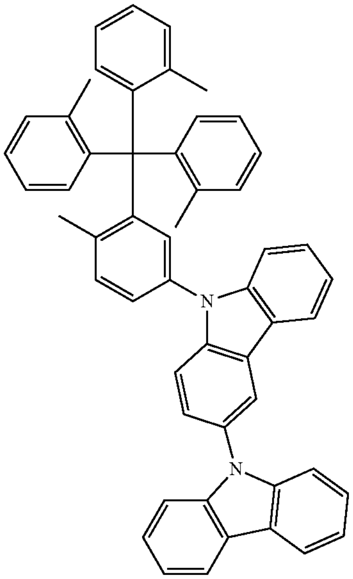

-continued
63
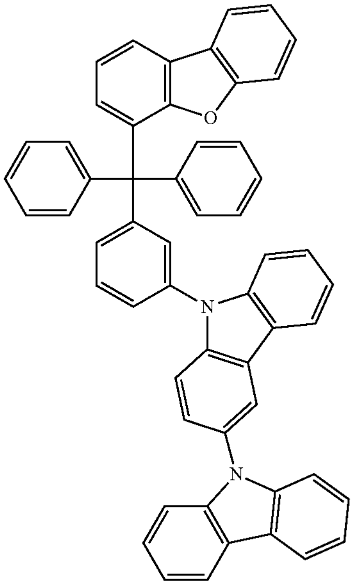
64
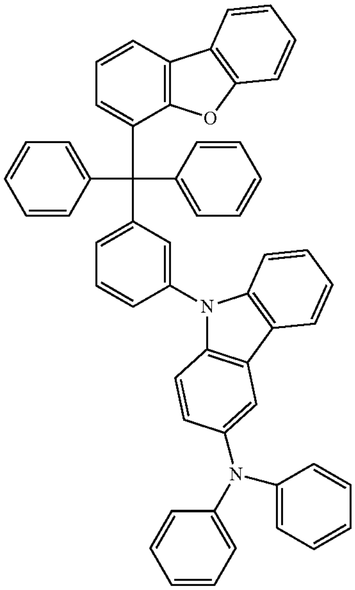
-continued
65
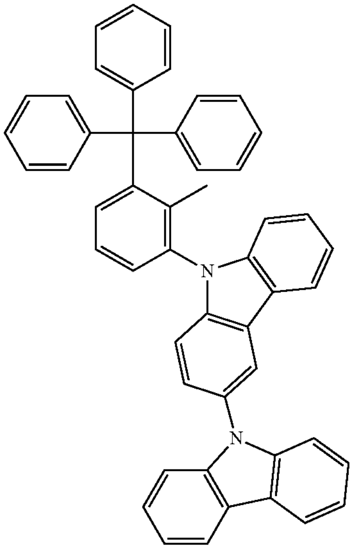
66
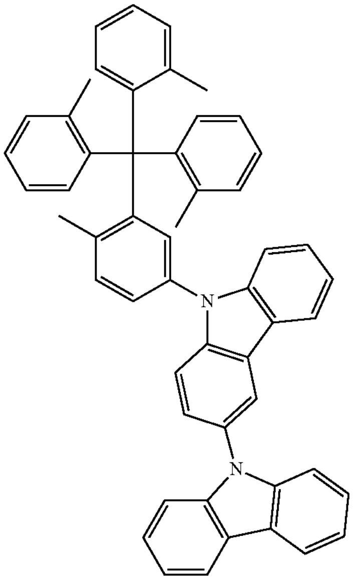

-continued
67
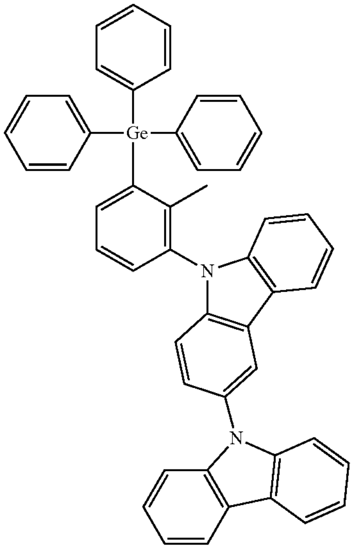
68
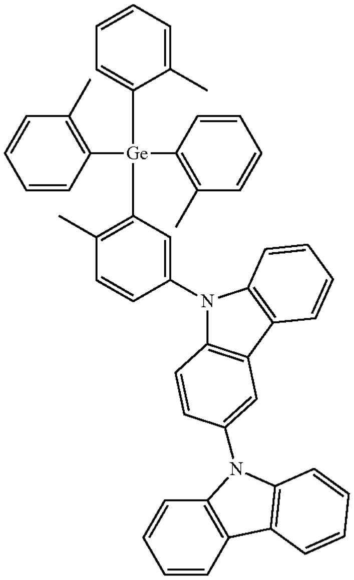
-continued
69
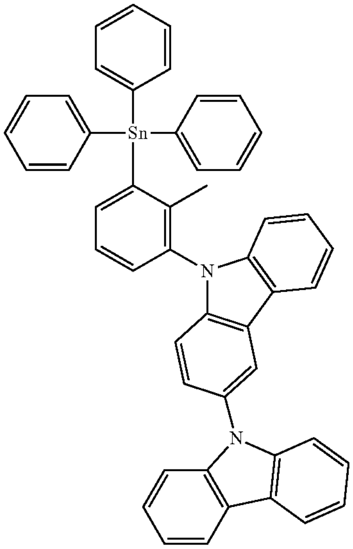
70
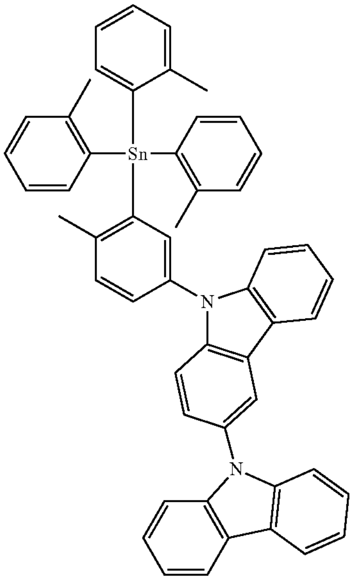

-continued
71
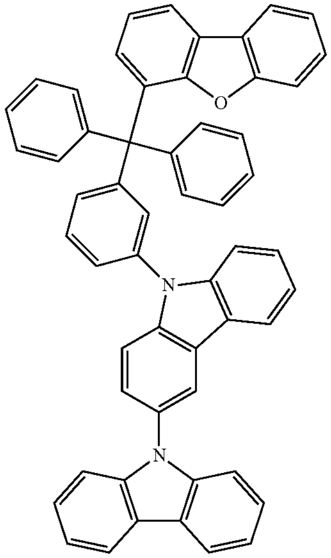
72
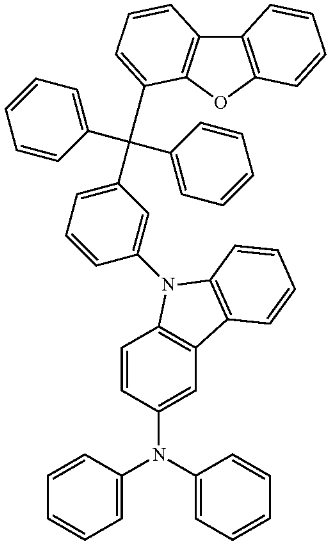
73
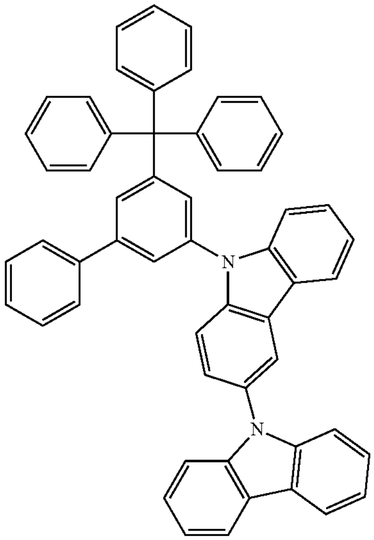
-continued
74
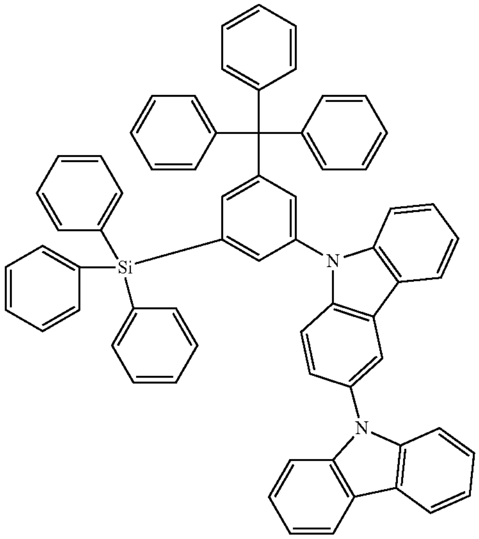
75
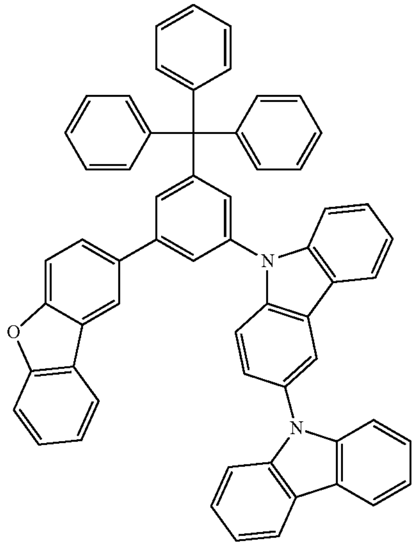
76
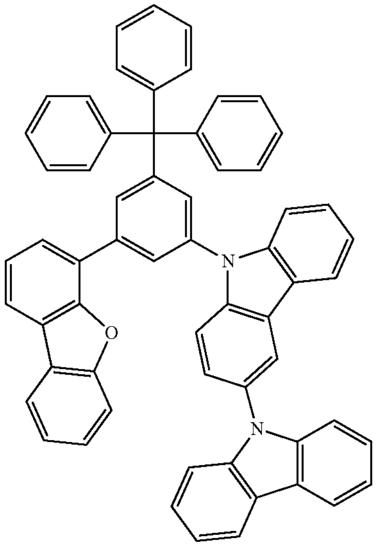

-continued

77

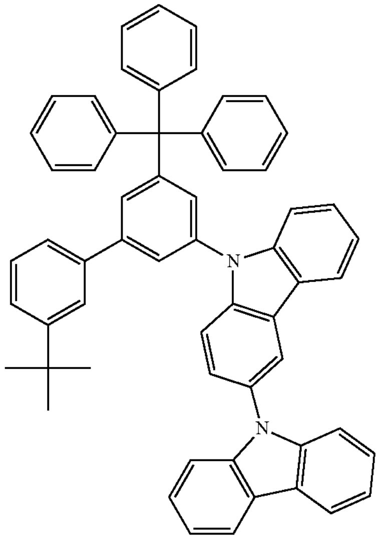

78

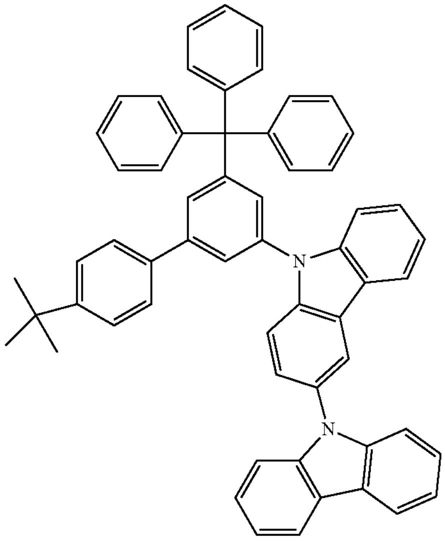

79

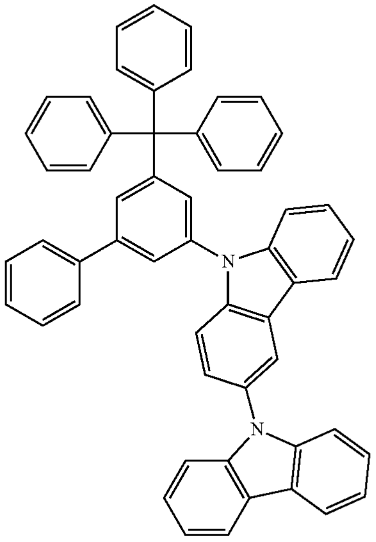

-continued

80

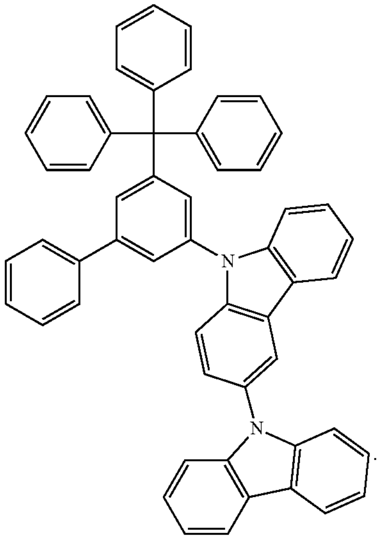

The heterocyclic compound represented by Formula 1 may include a structure in which four cyclic groups are substituted to a carbon group element (atom X in Formula 1) and a structure in which carbazole rings or amine groups are consecutively bound (e.g., bonded to each other) via C—N bonds.

As Formula 1 may include a structure in which four cyclic groups are substituted to a carbon group element (atom X in Formula 1), Formula 1 may be stabilized in terms of energy level due to a vacant d-orbital (e.g., a vacant d-orbital of the atom X) and have a high triplet energy. The carbon group element (atom X) may have different bond energy and different mobility characteristics depending on the period of the atom X (e.g., depending on the row of the Periodic Table that atom X occupies).

As Formula 1 may include a structure in which carbazole rings or amine groups are consecutively bound (e.g., bonded to each other) via C—N bonds, Formula 1 may be excellent in driving voltage improvement, luminescence efficiency, and energy transfer upon a combination with a phosphorescent dopant.

Therefore, an electronic device, e.g., an organic light-emitting device, employing the heterocyclic compound represented by Formula 1 may have a low driving voltage, high maximum quantum yield, high efficiency, and long lifespan.

Methods of synthesizing the heterocyclic compound represented by Formula 1 should be readily apparent to those of ordinary skill in the art by referring to the Examples described herein.

At least one heterocyclic compound represented by Formula 1 may be included between a pair of electrodes in an organic light-emitting device. In some embodiments, the heterocyclic compound may be included in an emission layer. In some embodiments, the heterocyclic compound represented by Formula 1 may be used as a material for forming a capping layer, which is on outer sides of a pair of electrodes in an organic light-emitting device.

According to one or more embodiments, an organic light-emitting device may include: a first electrode; a second electrode facing the first electrode; an organic layer between the first electrode and the second electrode and including an emission layer, and at least one of the heterocyclic compound represented by Formula 1.

As used herein, the expression the "(organic layer) includes at least one heterocyclic compound" may be construed as meaning the "(organic layer) may include one heterocyclic compound of Formula 1 or two different heterocyclic compounds of Formula 1."

For example, the organic layer may include only Compound 1 as the heterocyclic compound. In this embodiment, Compound 1 may be included in the emission layer of the organic light-emitting device. In some embodiments, the organic layer may include Compounds 1 and 2 as the heterocyclic compounds. In this embodiment, Compounds 1 and 2 may be included in the same layer (for example, both Compounds 1 and 2 may be included in an emission layer) or in different layers (for example, Compound 1 may be included in an emission layer, and Compound 2 may be included in an electron transport layer).

In some embodiments, the first electrode may be an anode, the second electrode may be a cathode, and the organic layer may include the heterocyclic compound, and the organic layer may further include a hole transport region between the first electrode and the emission layer and an electron transport region between the emission layer and the second electrode.

In some embodiments, the hole transport region may include a hole injection layer, a hole transport layer, an emission auxiliary layer, an electron blocking layer, or a combination thereof, and the electron transport region may include a hole blocking layer, an electron transport layer, an electron injection layer, or a combination thereof.

In some embodiments, the emission layer may include the heterocyclic compound.

In some embodiments, the emission layer may include a host and a dopant, the host may be different from the dopant, a content of the host may be greater than a content of the dopant, and the host may include the heterocyclic compound.

In some embodiments, the emission layer may emit blue light or blue-green light.

In some embodiments, the dopant may emit blue light or blue-green light having a maximum emission wavelength in a range of about 400 nanometers (nm) to about 500 nm.

In some embodiments, the dopant may include a transition metal and may not include a transition metal-nitrogen bond and a transition metal-oxygen bond.

In some embodiments, the dopant may include a transition metal and a coordinate bond (e.g., a coordinate covalent bond or a dative bond) between the transition metal and a carbon atom.

In some embodiments, the dopant may include a transition metal and a carbon-carbon bond between a transition metal and a carbon atom in a carbene form.

In some embodiments, the dopant may include a transition metal and a ligand, and the ligand may include a carbon atom in a carbene form.

In some embodiments, the heterocyclic compound may be used as a material for a capping layer outside a pair of electrodes of the organic light-emitting device.

In some embodiments, an electronic apparatus may include the organic light-emitting device.

In some embodiments, the electronic apparatus may further include a thin-film transistor, wherein the thin-film transistor may include a source electrode and a drain electrode, and the first electrode of the organic light-emitting device may be electrically coupled to the source electrode or the drain electrode.

The term "organic layer" as used herein refers to a single layer and/or a plurality of layers between the first electrode and the second electrode in an organic light-emitting device. A material included in the "organic layer" is not limited to an organic material. For example, the organic layer may include an inorganic material.

In some embodiments, the organic light-emitting device may have i) a first electrode/organic layer/second electrode/second capping layer structure, ii) a first capping layer/first electrode/organic layer/second electrode structure, or iii) a first capping layer/first electrode/organic layer/second electrode/second capping layer structure, wherein layers of each structure are sequentially stacked in each stated order. At least one of the first capping layer and the second capping layer may include the heterocyclic compound.

Description of FIG. 1

FIG. 1 illustrates a schematic cross-sectional view of an organic light-emitting device 10 according to an embodiment. The organic light-emitting device 10 may include a first electrode 110, an organic layer 150, and a second electrode 190.

Hereinafter, the structure of the organic light-emitting device 10 according to an embodiment and a method of manufacturing an organic light-emitting device according to an embodiment will be described in connection with FIG. 1.

First Electrode 110

In FIG. 1, a substrate may be additionally under the first electrode 110 or above the second electrode 190. The substrate may be a glass substrate and/or a plastic substrate, each having excellent mechanical strength, thermal stability, transparency, surface smoothness, ease of handling, and/or water resistance.

The first electrode 110 may be formed by depositing and/or sputtering, onto the substrate, a material for forming the first electrode 110. When the first electrode 110 is an anode, the material for forming the first electrode 110 may be selected from materials with a high work function that facilitate hole injection.

The first electrode 110 may be a reflective electrode, a semi-transmissive electrode, or a transmissive electrode. When the first electrode 110 is a transmissive electrode, a material for forming the first electrode 110 may be selected from indium tin oxide (ITO), indium zinc oxide (IZO), tin oxide ($SnO_2$), zinc oxide (ZnO), and any combinations thereof, but embodiments are not limited thereto. In some embodiments, when the first electrode 110 is a semi-transmissive electrode or a reflective electrode, as a material for forming the first electrode 110, at least one selected from magnesium (Mg), silver (Ag), aluminum (Al), aluminum-lithium (Al—Li), calcium (Ca), magnesium-indium (Mg—In), magnesium-silver (Mg—Ag), and any combination thereof may be used, but embodiments are not limited thereto.

The first electrode 110 may have a single-layered structure, or a multi-layered structure including two or more layers. In some embodiments, the first electrode 110 may have a triple-layered structure of ITO/Ag/ITO, but embodiments are not limited thereto.

Organic Layer 150

The organic layer 150 may be on the first electrode 110. The organic layer 150 may include an emission layer.

The organic layer 150 may further include a hole transport region between the first electrode 110 and the emission layer and an electron transport region between the emission layer and the second electrode 190.

Hole Transport Region in Organic Layer 150

The hole transport region may have i) a single-layered structure including (e.g., consisting of) a single layer including (e.g., consisting of) a single material, ii) a single-layered structure including (e.g., consisting of) a single layer including a plurality of different materials, or iii) a multi-layered structure having a plurality of layers including a plurality of different materials.

The hole transport region may include at least one selected from a hole injection layer, a hole transport layer, an emission auxiliary layer, and an electron blocking layer.

For example, the hole transport region may have a single-layered structure including a single layer including a plurality of different materials or a multi-layered structure, e.g., a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron blocking layer structure, wherein layers of each structure are sequentially stacked on the first electrode 110 in each stated order, but embodiments are not limited thereto.

The hole transport region may include at least one selected from m-MTDATA, TDATA, 2-TNATA, NPB (NPD), β-NPB, TPD, a spiro-TPD, a spiro-NPB, methylated-NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), (polyaniline)/poly(4-styrenesulfonate) (PANI/PSS), CzSi (9-(4-tert-butylphenyl)-3,6-bis(triphenylsilyl)-9H-carbazole), a compound represented by Formula 201, and a compound represented by Formula 202:

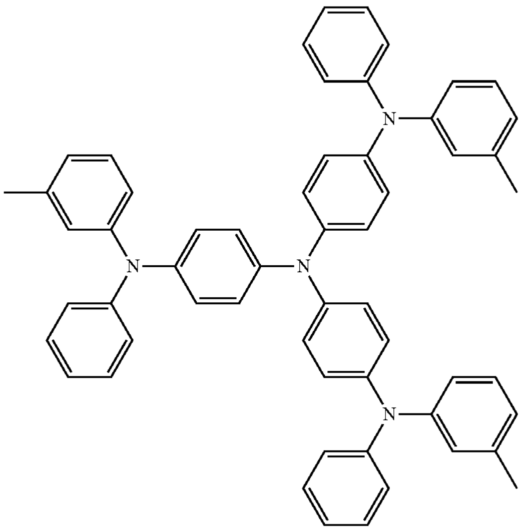

m-MTDATA

-continued

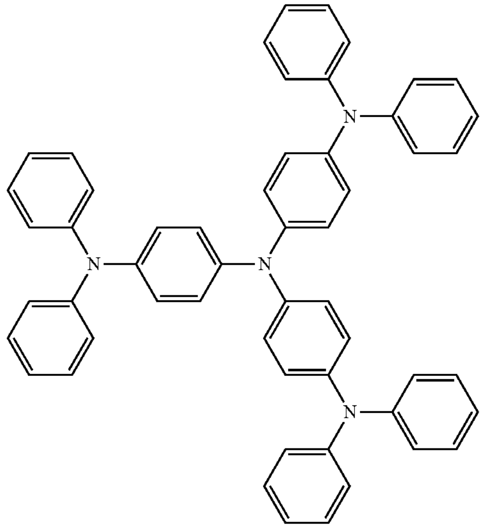

TDATA

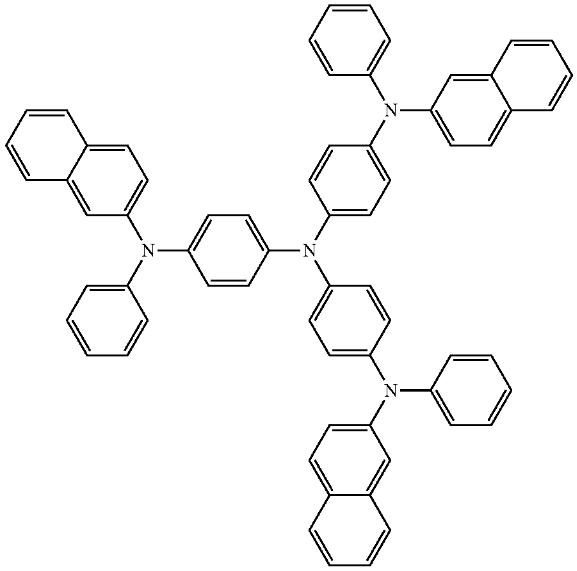

2-TNATA

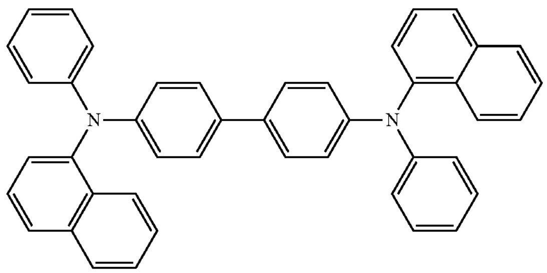

NPB

-continued

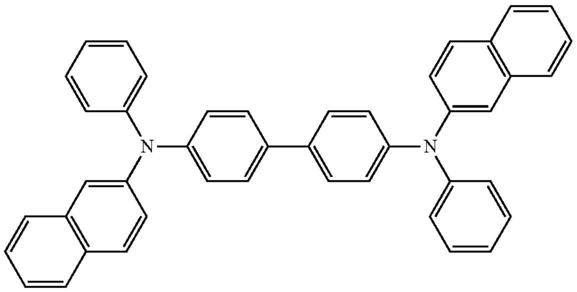

B-NPB

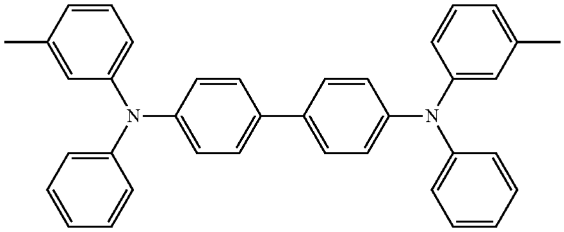

TPD

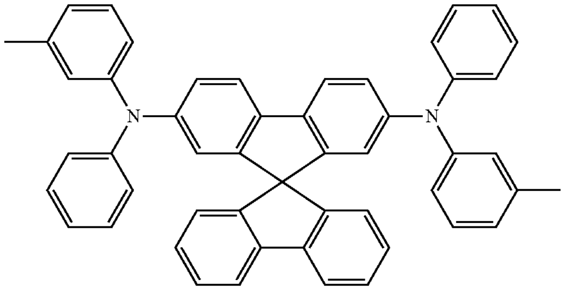

Spiro-TPD

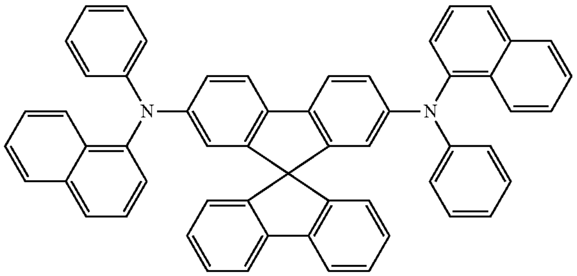

Spiro-NPB

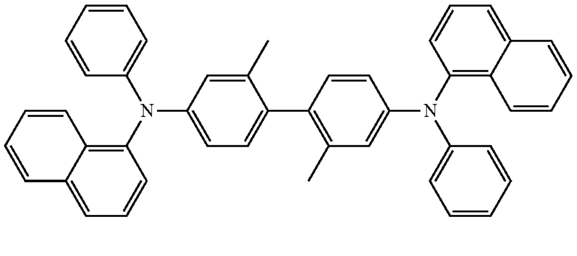

methylated NPB

-continued

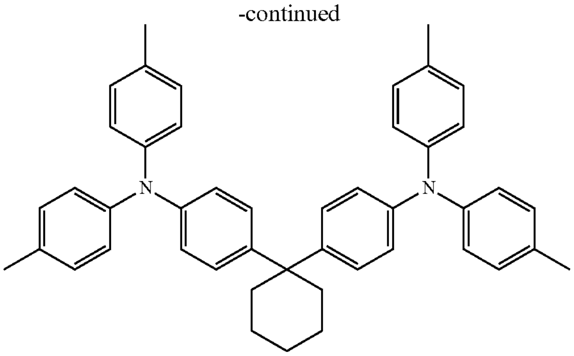

TAPC

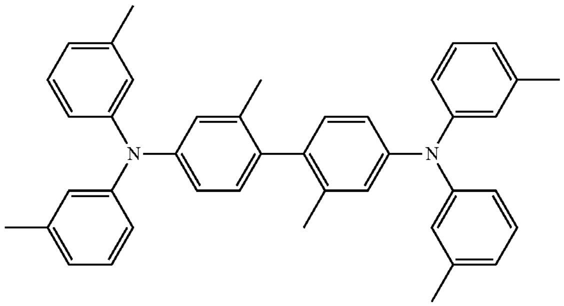

HMTPD

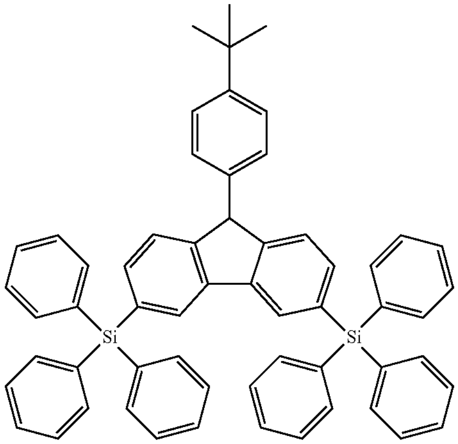

CzSi

Formula 201

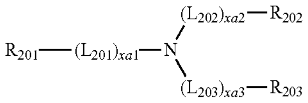

Formula 202

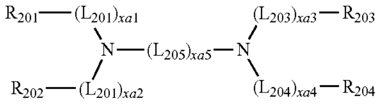

wherein, in Formulae 201 and 202, $L_{201}$ to $L_{204}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, $L_{205}$ may be selected from *—O—*', *—S—*', *—N($Q_{201}$)-*', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xa1 to xa4 may each independently be an integer from 0 to 3, xa5 may be an integer from 1 to 10, and $R_{201}$ to $R_{204}$ and $Q_{201}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In some embodiments, in Formula 202, $R_{201}$ and $R_{202}$ may optionally be bound via a single bond, a dimethyl-methylene group, or a diphenyl-methylene group, and $R_{203}$ and $R_{204}$ may optionally be bound via a single bond, a dimethyl-methylene group, or a diphenyl-methylene group.

In some embodiments, in Formulae 201 and 202, $L_{201}$ to $L_{205}$ may each independently be selected from:

a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xa1 to xa4 may each independently be 0, 1, or 2.

In one or more embodiments, xa5 may be 1, 2, 3, or 4.

In one or more embodiments, $R_{201}$ to $R_{204}$ and $Q_{201}$ may each independently be selected from: a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —$Si(Q_{31})(Q_{32})(Q_{33})$, and —$N(Q_{31})(Q_{32})$, wherein $Q_{31}$ to $Q_{33}$ may respectively be understood by referring to the descriptions of $Q_{31}$ to $Q_{33}$ provided herein.

In one or more embodiments, in Formula 201, at least one of $R_{201}$ to $R_{203}$ may be selected from:

a fluorenyl group, a spiro-bifluorenyl group, a carbazolyl group, a dibenzofuranyl group, and a dibenzothiophenyl group; and a fluorenyl group, a spiro-bifluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but embodiments are not limited thereto.

In one or more embodiments, in Formula 202, i) $R_{201}$ and $R_{202}$ may be bound via a single bond, and/or ii) $R_{203}$ and $R_{204}$ may be bound via a single bond.

In one or more embodiments, in Formula 202, at least one of $R_{201}$ to $R_{204}$ may be selected from:

a carbazolyl group; and a carbazolyl group substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but embodiments are not limited thereto.

The compound represented by Formula 201 may be represented by Formula 201-1:

Formula 201-1

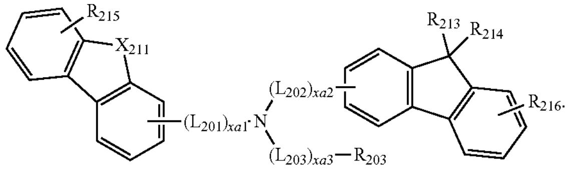

In some embodiments, the compound represented by Formula 201 may be represented by Formula 201-2, but embodiments are not limited thereto:

Formula 201-2

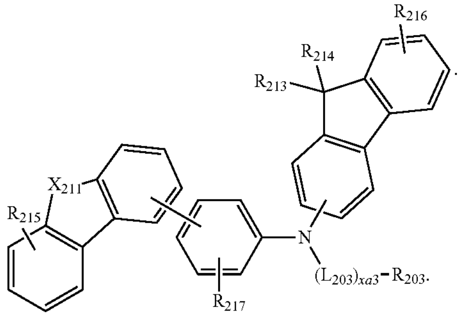

In some embodiments, the compound represented by Formula 201 may be represented by Formula 201-2(1), but embodiments are not limited thereto:

Formula 201-2(1)

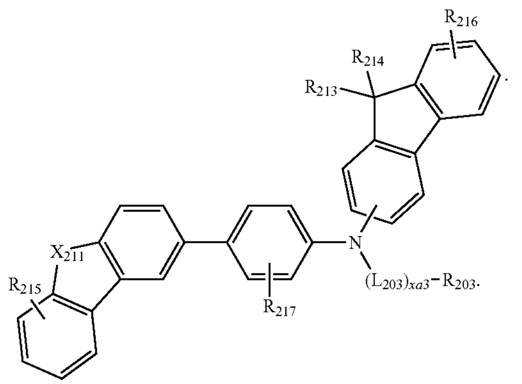

The compound represented by Formula 201 may be represented by Formula 201A:

Formula 201A

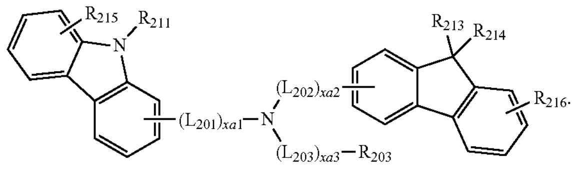

In some embodiments, the compound represented by Formula 201 may be represented by Formula 201A(1), but embodiments are not limited thereto:

Formula 201A(1)

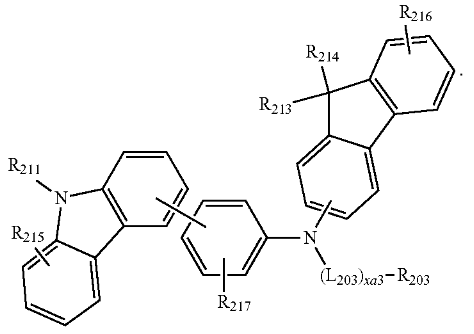

In some embodiments, the compound represented by Formula 201 may be represented by Formula 201A-1, but embodiments are not limited thereto:

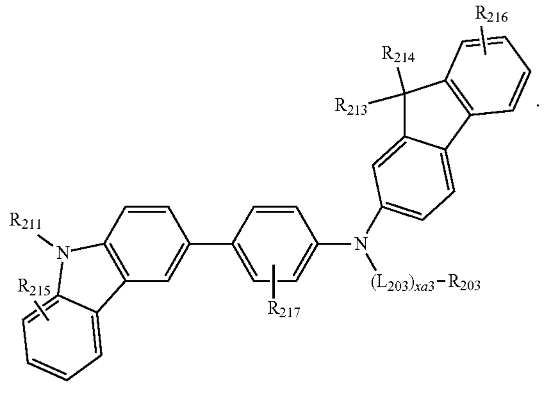

In some embodiments, the compound represented by Formula 202 may be represented by Formula 202-1:

Formula 202-1

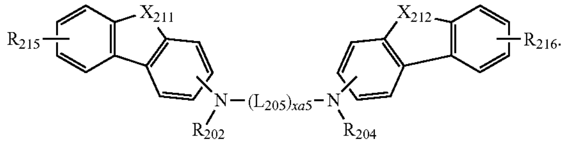

In one or more embodiments, the compound represented by Formula 202 may be represented by Formula 202-1(1):

Formula 202-1(1)

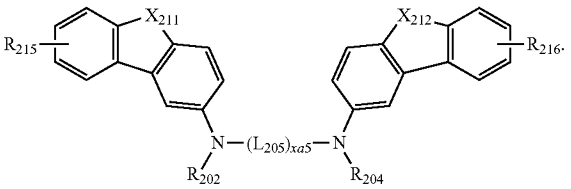

In some embodiments, the compound represented by Formula 202 may be represented by Formula 202A:

Formula 202A

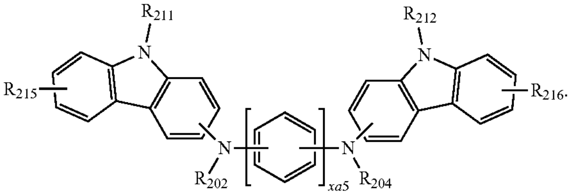

In some embodiments, the compound represented by Formula 202 may be represented by Formula 202A-1:

Formula 202A-1

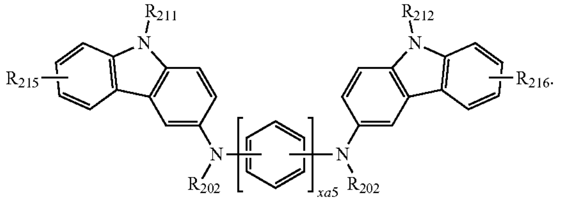

In Formulae 201-1, 201-2, 201-2(1), 201A, 201A(1), 201A-1, 202-1, 202-1(1), 202A, and 202A-1, $L_{201}$ to $L_{203}$, xa1 to xa3, xa5, and $R_{202}$ to $R_{204}$ may respectively be understood by referring to the descriptions of $L_{201}$ to $L_{203}$, xa1 to xa3, xa5, and $R_{202}$ to $R_{204}$ provided herein, $L_{205}$ may be selected from a phenylene group and a fluorenylene group, $X_{211}$ may be selected from O, S, and $N(R_{211})$, $X_{212}$ may be selected from O, S, and $N(R_{212})$, $R_{211}$ and $R_{212}$ may each be understood by referring to the description of $R_{203}$ provided herein, and $R_{213}$ to $R_{217}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

The hole transport region may include at least one compound selected from Compounds HT1 to HT48, but embodiments are not limited thereto:

HT1

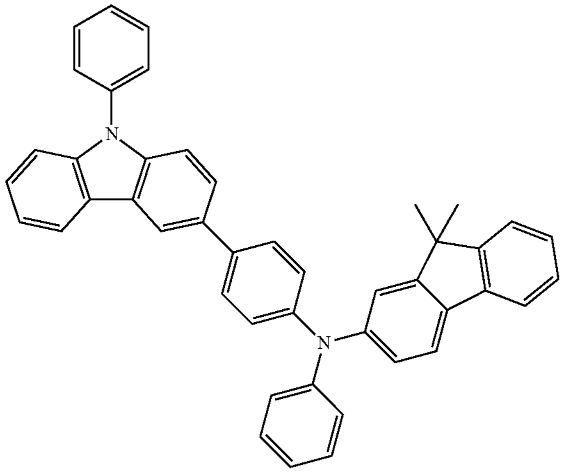

HT2

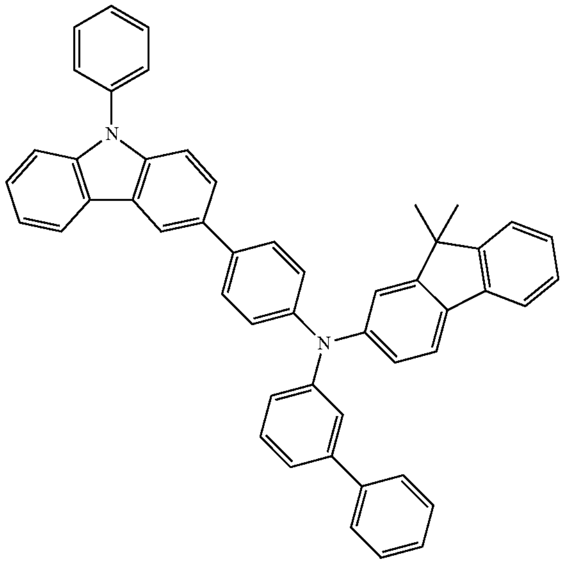

-continued
HT3
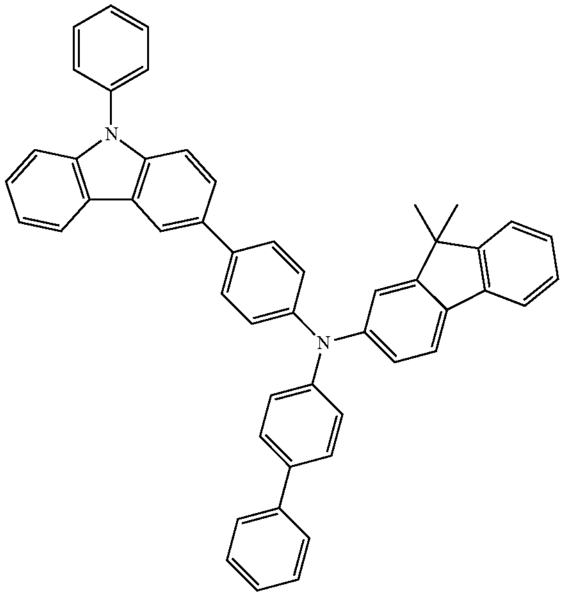
HT4
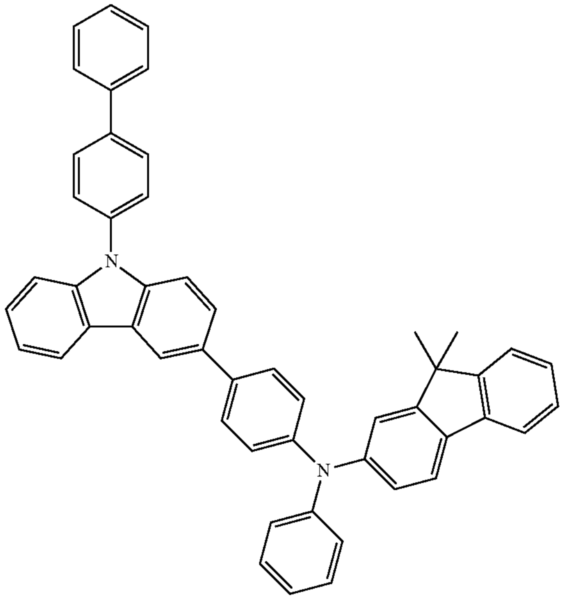
-continued
HT5
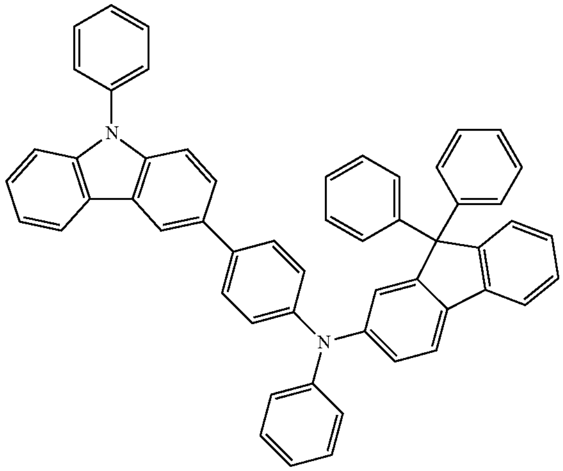
HT6
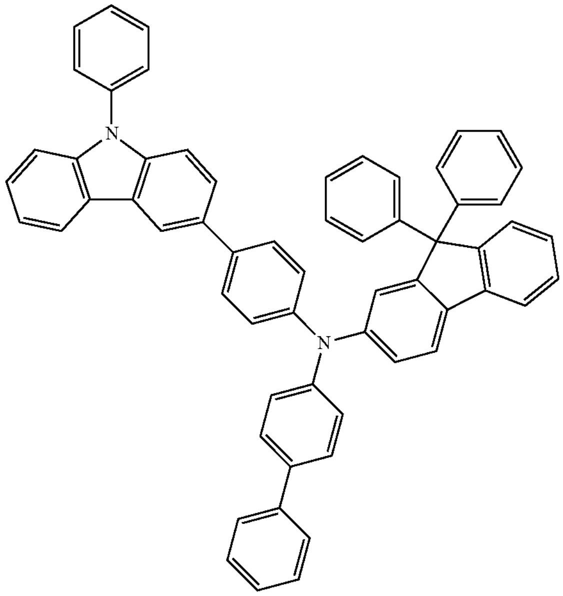

-continued
HT7
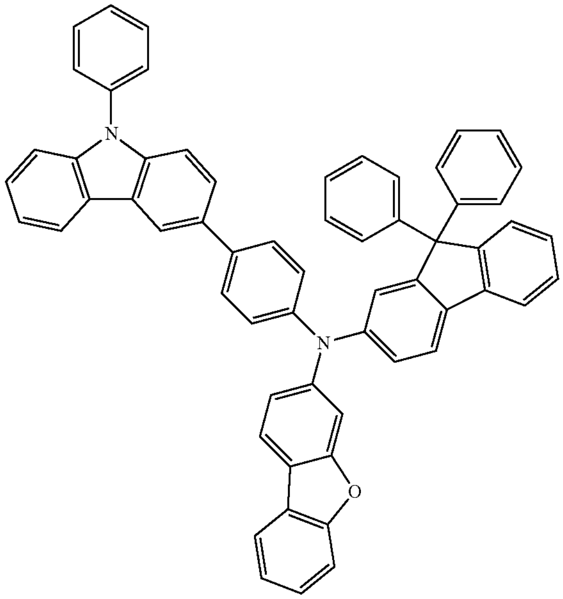
HT8
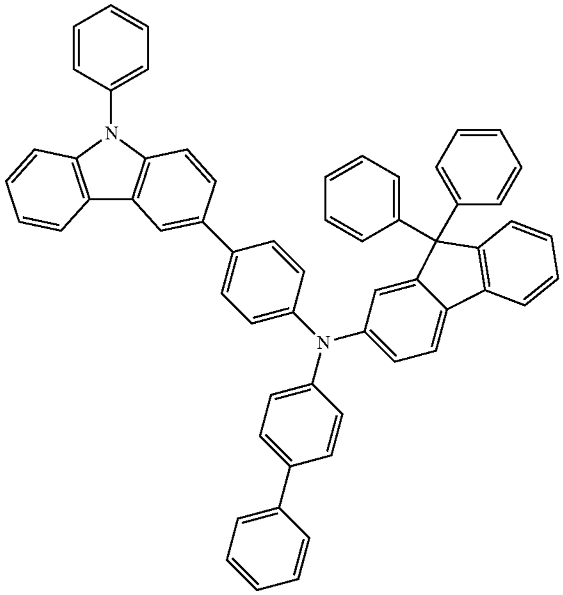
-continued
HT9
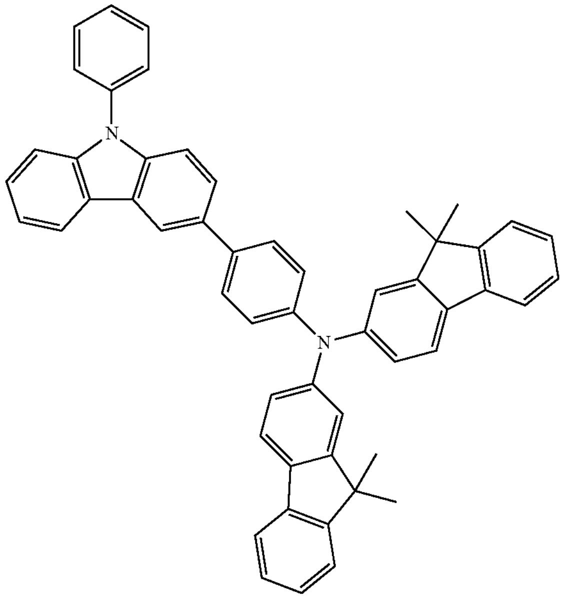
HT10
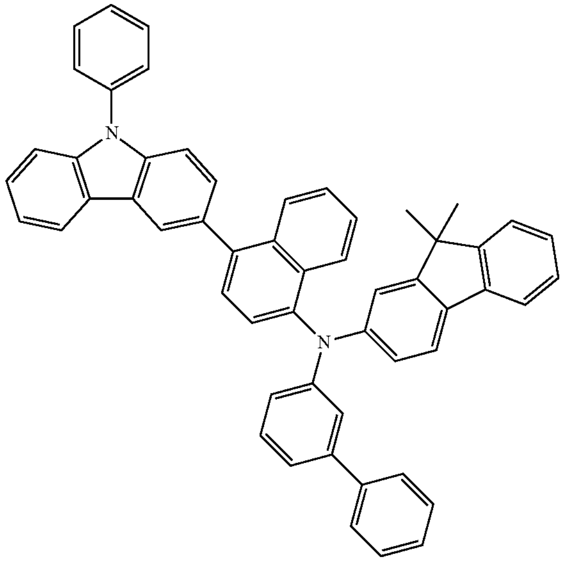

-continued
HT11
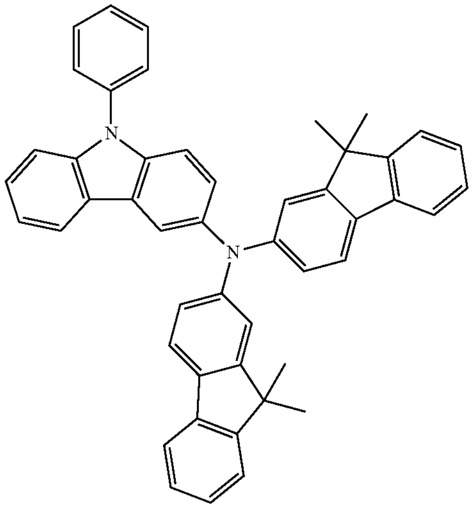
HT12
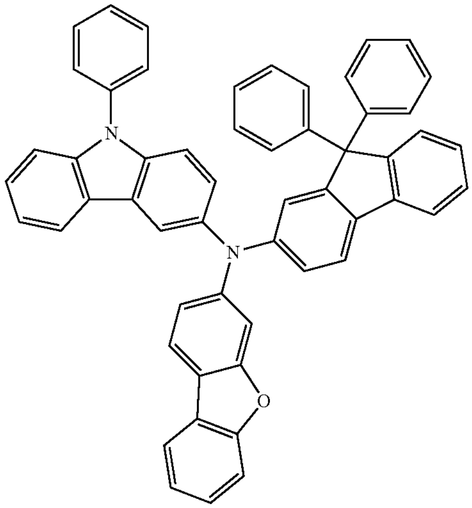
HT13
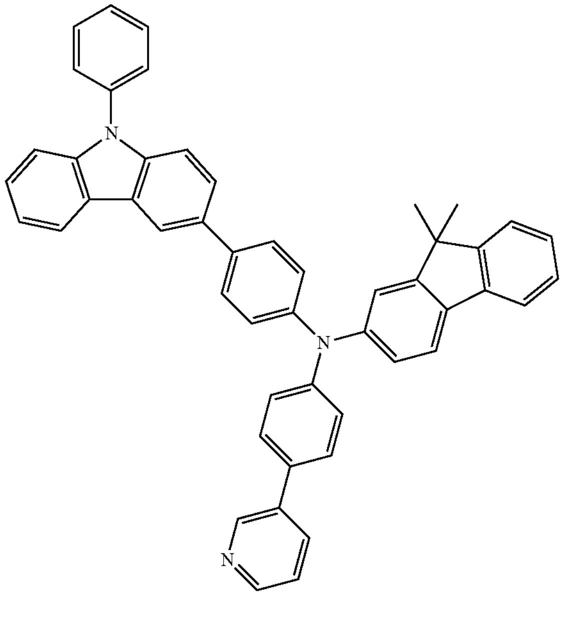
-continued
HT14
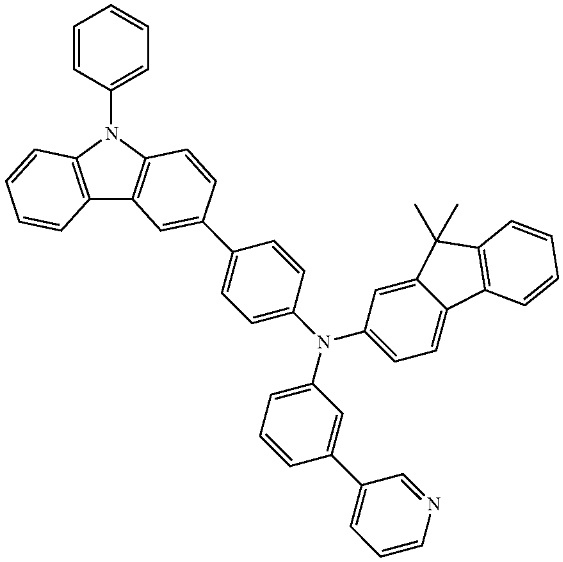
HT15
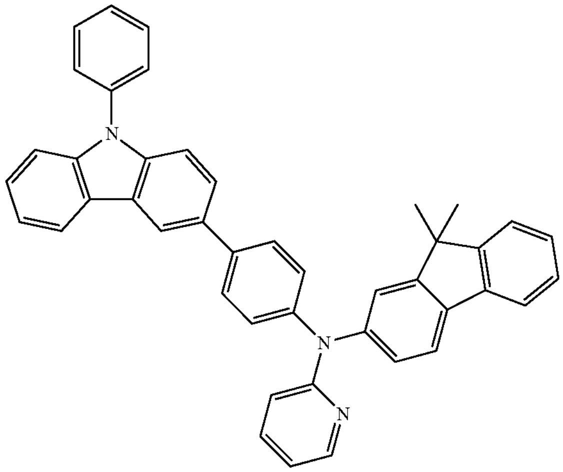
HT16
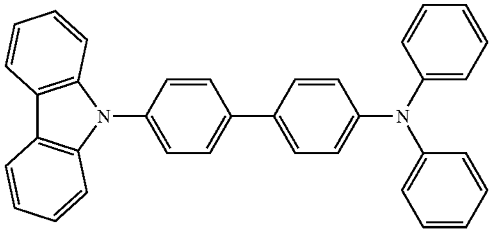

-continued
HT17
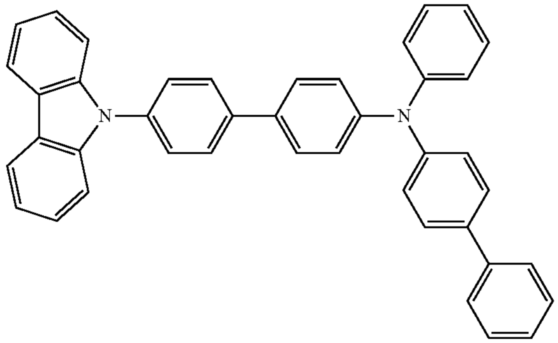
HT18
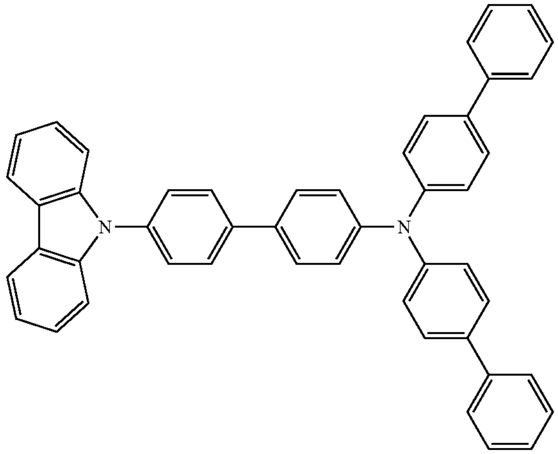
HT25
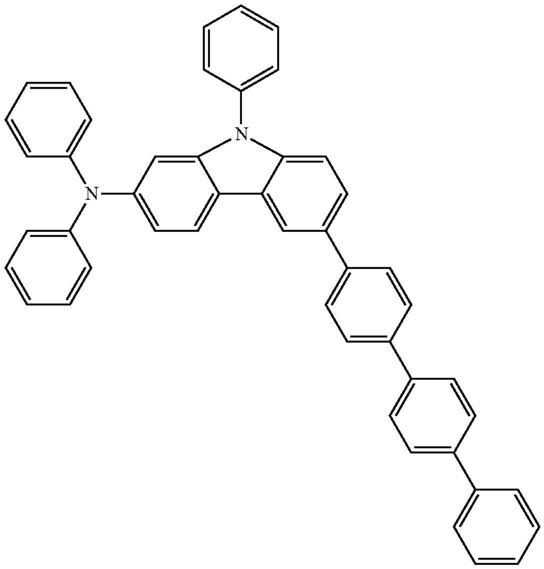
-continued
HT26
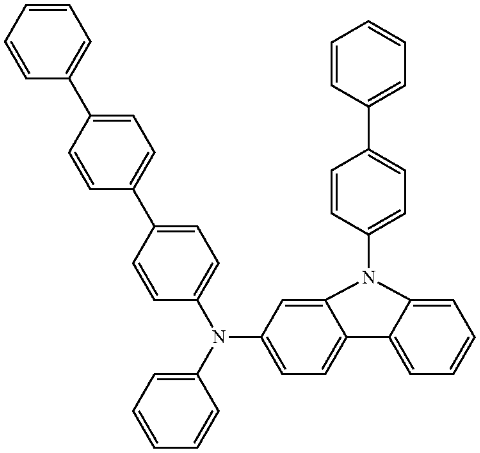
HT27
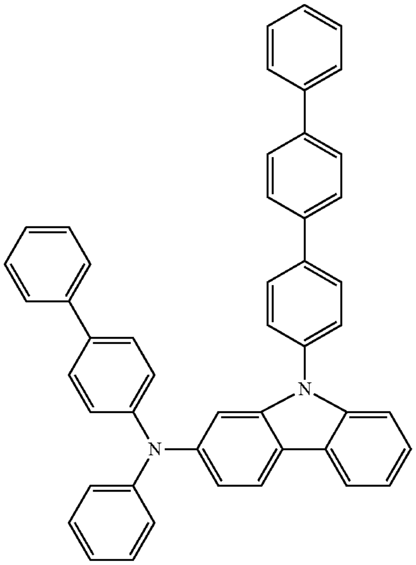
HT28
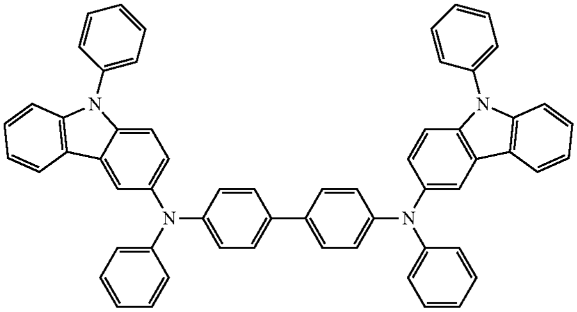

-continued
HT29
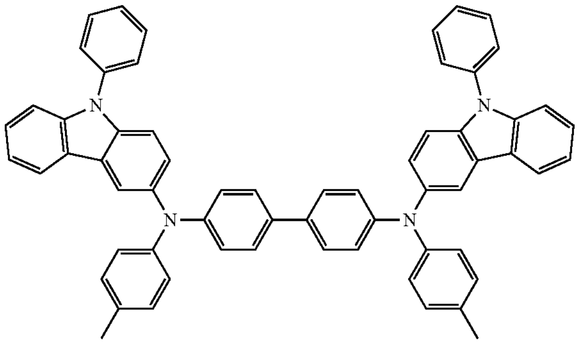
HT30
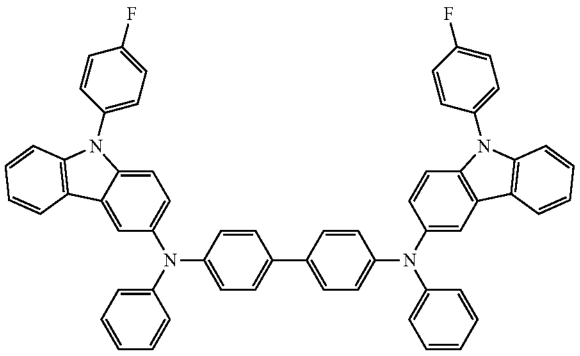
HT31
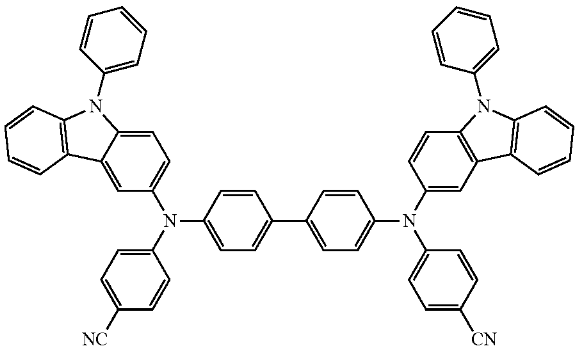
HT32
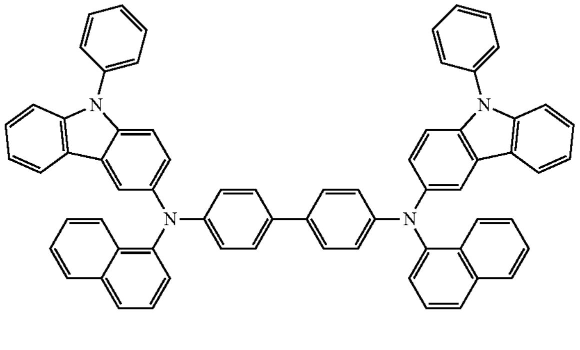
-continued
HT33
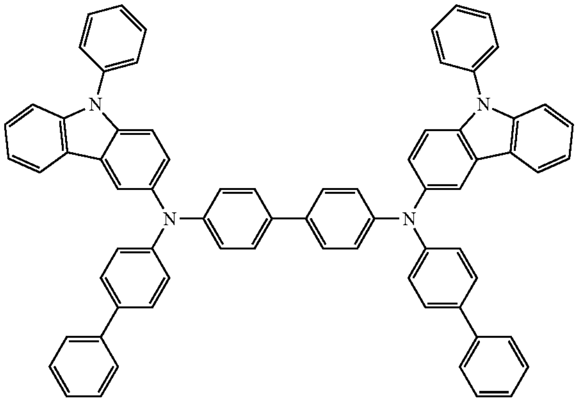
HT34
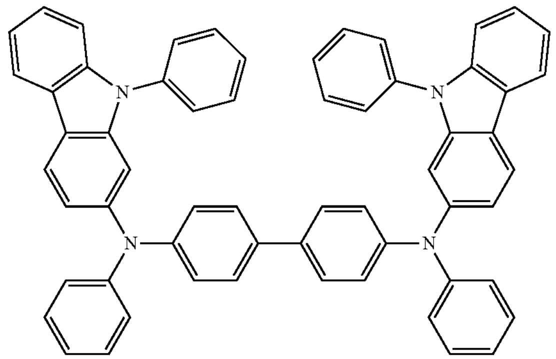
HT35
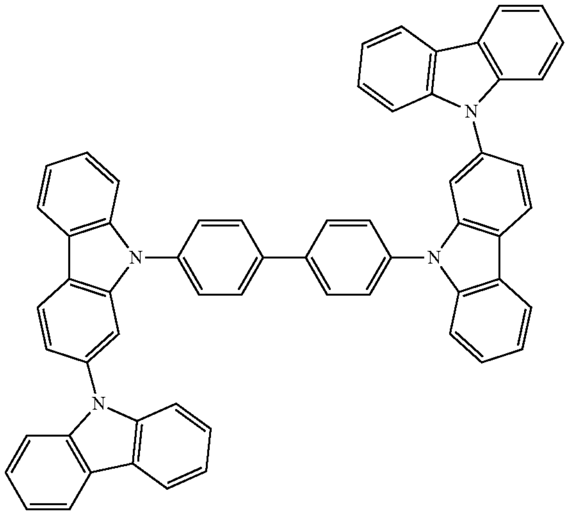

-continued
HT36
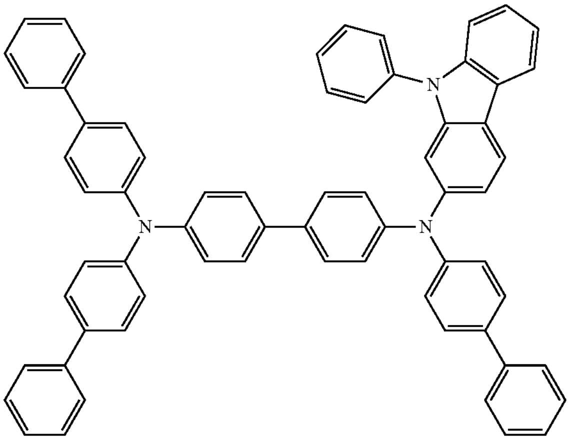
HT37
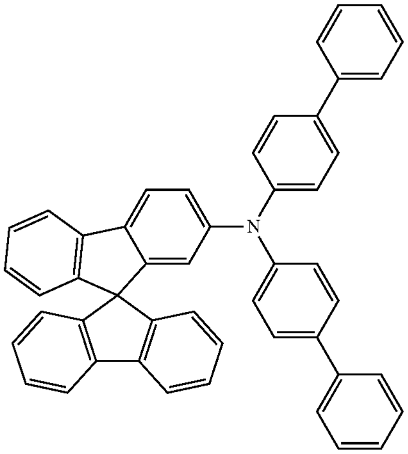
HT38
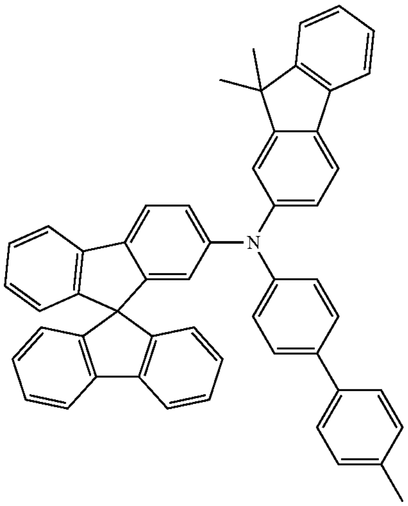
-continued
HT39
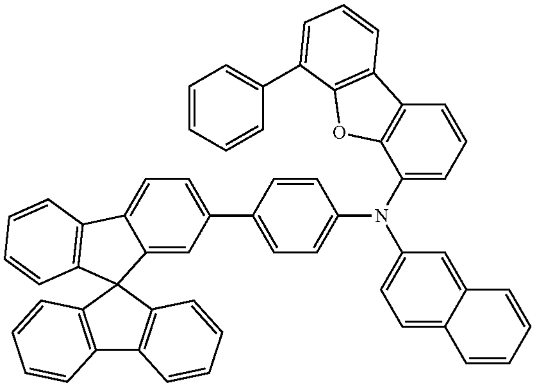
HT40
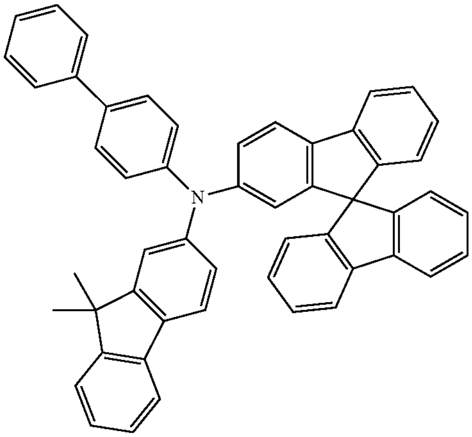
HT41
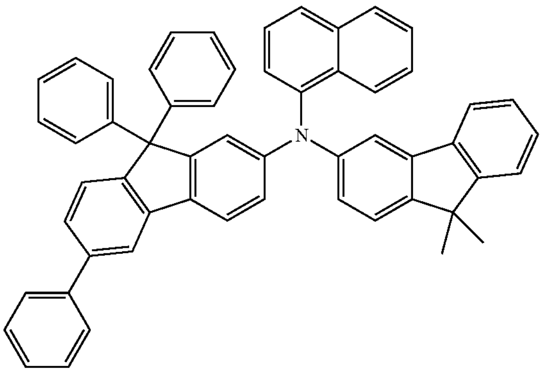

-continued
HT42
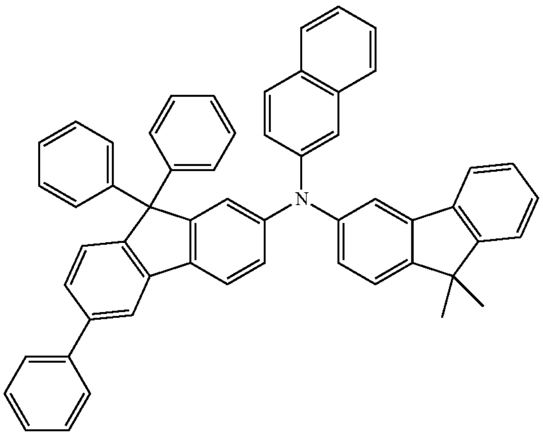
HT43
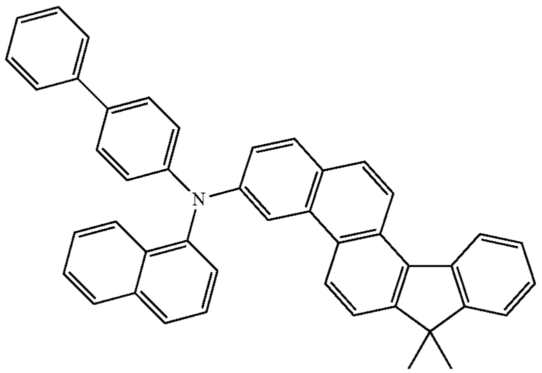
HT44
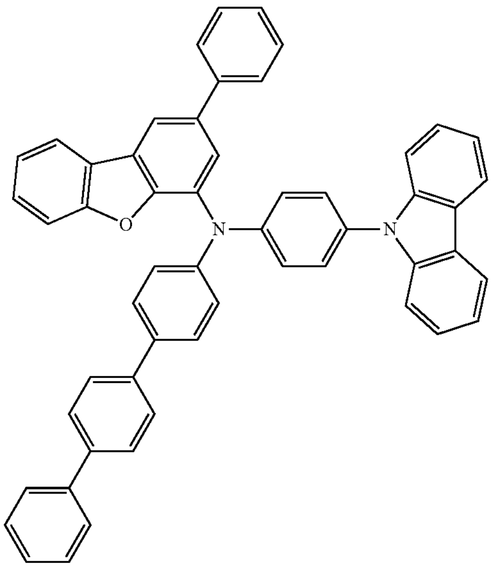
-continued
HT45
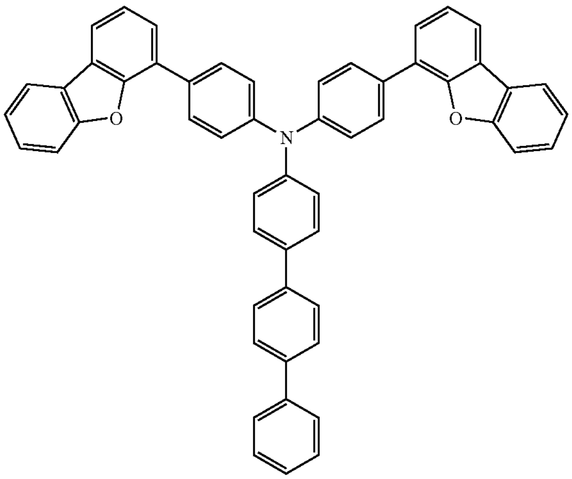
HT46
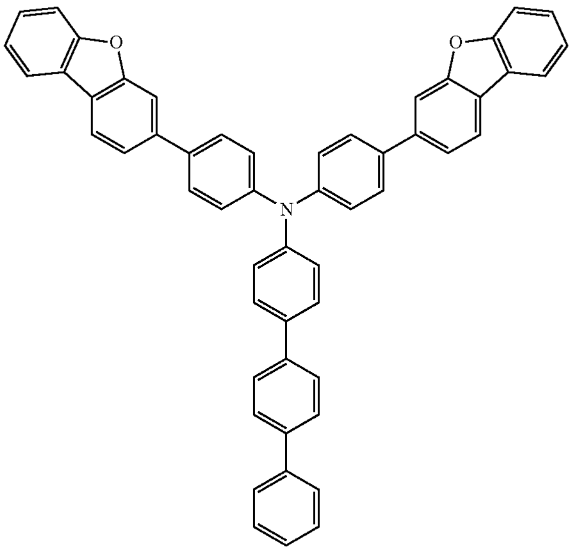
HT47
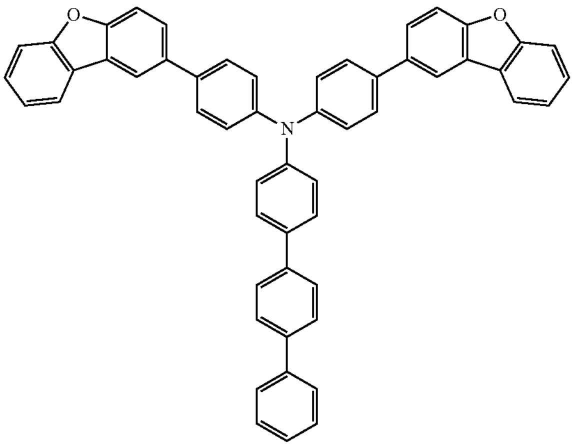

-continued

HT48

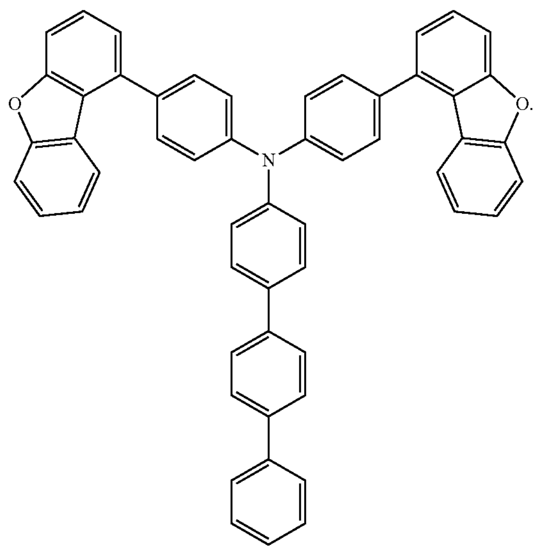

The thickness of the hole transport region may be in a range of about 100 (Angstroms) Å to about 10,000 Å, and in some embodiments, about 100 Å to about 1,000 Å. When the hole transport region includes at least one selected from a hole injection layer and a hole transport layer, the thickness of the hole injection layer may be in a range of about 100 Å to about 9,000 Å, and in some embodiments, about 100 Å to about 1,000 Å, and the thickness of the hole transport layer may be in a range of about 50 Å to about 2,000 Å, and in some embodiments, about 100 Å to about 1,500 Å. When the thicknesses of the hole transport region, the hole injection layer, and the hole transport layer are within any of the foregoing ranges, excellent hole transport characteristics may be obtained without a substantial increase in driving voltage.

The emission auxiliary layer may increase light emission efficiency by compensating for an optical resonance distance according to the wavelength of light emitted by an emission layer. The electron blocking layer may reduce or eliminate the flow of electrons from an electron transport region. The emission auxiliary layer and the electron blocking layer may include the aforementioned materials.

p-Dopant

The hole transport region may include a charge generating material as well as the aforementioned materials, to improve conductive properties of the hole transport region. The charge generating material may be substantially homogeneously or non-homogeneously dispersed in the hole transport region.

The charge generating material may include, for example, a p-dopant.

In some embodiments, the lowest unoccupied molecular orbital (LUMO) energy level of the p-dopant may be −3.5 eV or less.

The p-dopant may include at least one selected from a quinone derivative, a metal oxide, and a cyano group-containing compound, but embodiments are not limited thereto.

In some embodiments, the p-dopant may include:

- a quinone derivative, such as tetracyanoquinodimethane (TCNQ) or 2,3,5,6-tetrafluoro-7,7,8,8-tetracyanoquinodimethane (F4-TCNQ);
- a metal oxide, such as tungsten oxide or molybdenum oxide;
- 1,4,5,8,9,12-hexaazatriphenylene-hexacarbonitrile (HAT-CN); and
- a compound represented by Formula 221, but embodiments are not limited thereto:

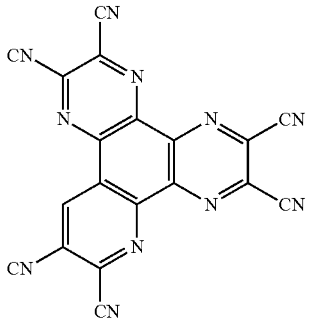

HAT-CN

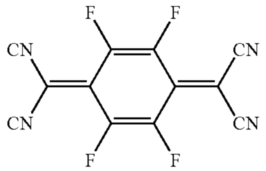

F4-TCNQ

Formula 221

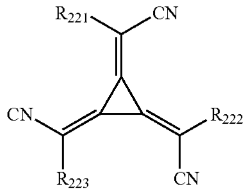

wherein, in Formula 221, $R_{221}$ to $R_{223}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, wherein at least one selected from $R_{221}$ to $R_{223}$ may include at least one substituent selected from a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with —Br, and a $C_1$-$C_{20}$ alkyl group substituted with —I.

Emission Layer in Organic Layer 150

When the organic light-emitting device 10 is a full color organic light-emitting device, the emission layer may be patterned into a red emission layer, a green emission layer, or a blue emission layer, according to a sub-pixel. In one or more embodiments, the emission layer may have a stacked structure. The stacked structure may include two or more layers selected from a red emission layer, a green emission layer, and a blue emission layer. The two or more layers may be in direct contact (e.g., physical contact) with each other. In some embodiments, the two or more layers may be separated from each other. In one or more embodiments, the emission layer may include two or more materials. The two or more materials may include a red light-emitting material, a green light-emitting material, or a blue light-emitting material. The two or more materials may be mixed with each other in a single layer. The two or more materials mixed with each other in the single layer may emit white light.

The emission layer may include the heterocyclic compound represented by Formula 1.

The emission layer may include a host and a luminescent material. The luminescent material may include at least one of a phosphorescent dopant, a fluorescent dopant, and a quantum dot.

The amount of the dopant in the emission layer may be, in general, in a range of about 0.01 parts to about 15 parts by weight based on 100 parts by weight of the host, but embodiments are not limited thereto.

In some embodiments, the emission layer may emit blue light or blue-green light.

In some embodiments, the heterocyclic compound emits blue light or blue-green light having a maximum emission wavelength in a range of about 400 nm to about 500 nm.

The thickness of the emission layer may be in a range of about 100 Å to about 1,000 Å, and in some embodiments, about 200 Å to about 600 Å. When the thickness of the emission layer is within any of the foregoing ranges, improved luminescence characteristics may be obtained without a substantial increase in driving voltage.

Host in Emission Layer

The host may be different from the dopant, and a content (e.g., amount or weight) of the host may be greater than a content (e.g., amount or weight) of the dopant, and the host may include the heterocyclic compound represented by Formula 1.

The host may further include a compound represented by Formula 301:

$$[Ar_{301}]_{xb11}\text{-}[(L_{301})_{xb1}\text{-}R_{301}]_{xb21} \quad \text{Formula 301}$$

wherein, in Formula 301, $Ar_{301}$ may be selected from a substituted or unsubstituted $C_5$-$C_{60}$ carbocyclic group and a substituted or unsubstituted $C_1$-$C_{60}$ heterocyclic group, xb11 may be 1, 2, or 3, $L_{301}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xb1 may be an integer from 0 to 5, $R_{301}$ may be selected from deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $—Si(Q_{301})(Q_{302})(Q_{303})$, $—N(Q_{301})(Q_{302})$, $—B(Q_{301})(Q_{302})$, $—C(=O)(Q_{301})$, $—S(=O)_2(Q_{301})$, and $—P(=O)(Q_{301})(Q_{302})$, and xb21 may be an integer from 1 to 5, wherein $Q_{301}$ to $Q_{303}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments are not limited thereto.

In some embodiments, in Formula 301, $Ar_{301}$ may be selected from:

a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group; and a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, $—Si(Q_{31})(Q_{32})(Q_{33})$, $—N(Q_{31})(Q_{32})$, $—B(Q_{31})(Q_{32})$, $—C(=O)(Q_{31})$, $—S(=O)_2(Q_{31})$, and $—P(=O)(Q_{31})(Q_{32})$, wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments are not limited thereto.

When xb11 in Formula 301 is 2 or greater, at least two $Ar_{301}$(s) may be bound via a single bond.

In one or more embodiments, the compound represented by Formula 301 may be represented by Formula 301-1 or 301-2:

Formula 301-1

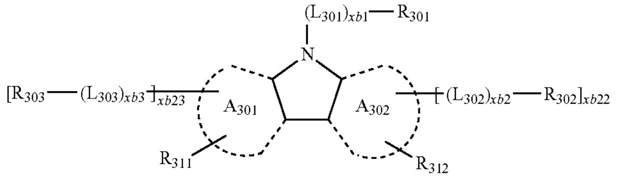

Formula 301-2

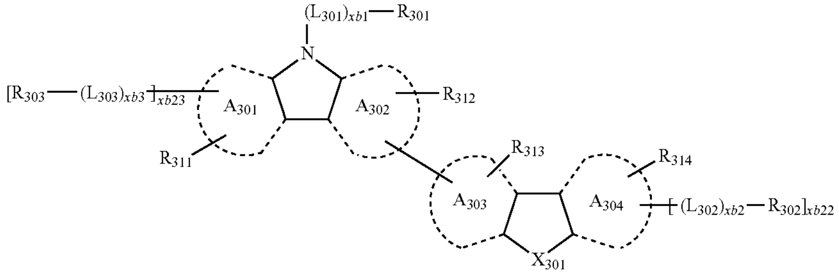

wherein, in Formulae 301-1 to 301-2, $A_{301}$ to $A_{304}$ may each independently be selected from a benzene group, a naphthalene group, a phenanthrene group, a fluoranthene group, a triphenylene group, a pyrene group, a chrysene group, a pyridine group, a pyrimidine group, an indene group, a fluorene group, a spiro-bifluorene group, a benzofluorene group, a dibenzofluorene group, an indole group, a carbazole group, a benzocarbazole group, a dibenzocarbazole group, a furan group, a benzofuran group, a dibenzofuran group, a naphthofuran group, a benzonaphthofuran group, a dinaphthofuran group, a thiophene group, a benzothiophene group, a dibenzothiophene group, a naphthothiophene group, a benzonapthothiophene group, and a dinaphthothiophene group, $X_{301}$ may be O, S, or N-[$(L_{304})_{xb4}$-$R_{304}$], $R_{311}$ to $R_{314}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, and —$P(=O)(Q_{31})(Q_{32})$, xb22 and xb23 may each independently be 0, 1, or 2, $L_{301}$, xb1, $R_{301}$, and $Q_{31}$ to $Q_{33}$ may respectively be understood by referring to the descriptions of $L_{301}$, xb1, $R_{301}$, and $Q_{31}$ to $Q_{33}$ provided herein, $L_{302}$ to $L_{304}$ may each be understood by referring to the description of $L_{301}$ provided herein, xb2 to xb4 may each be understood by referring to the description of xb1 provided herein, and $R_{302}$ to $R_{304}$ may each be understood by referring to the description of $R_{301}$ provided herein.

In some embodiments, in Formulae 301, 301-1, and 301-2, $L_{301}$ to $L_{304}$ may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, and —$P(=O)(Q_{31})(Q_{32})$, wherein $Q_{31}$ to $Q_{33}$ may respectively be understood by referring to the descriptions of $Q_{31}$ to $Q_{33}$ provided herein.

In some embodiments, in Formulae 301, 301-1, and 301-2, $R_{301}$ to $R_{304}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —$Si(Q_{31})(Q_{32})(Q_{33})$, $—N(Q_{31})(Q_{32})$, $—B(Q_{31})(Q_{32})$, $—C(=O)(Q_{31})$, $—S(=O)_2(Q_{31})$, and $—P(=O)(Q_{31})(Q_{32})$, wherein $Q_{31}$ to $Q_{33}$ may respectively be understood by referring to the descriptions of $Q_{31}$ to $Q_{33}$ provided herein.

In some embodiments, the host may include an alkaline earth metal complex. For example, the host may include a beryllium (Be) complex, e.g., Compound H55, a magnesium (Mg) complex, or a zinc (Zn) complex.

The host may include at least one selected from 9,10-di(2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolylbenzene (mCP), 1,3,5-tri(carbazol-9-yl)benzene (TCP), and Compounds H1 to H55, but embodiments are not limited thereto:

H1

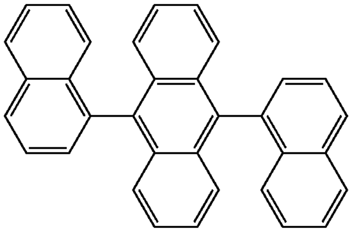

H2

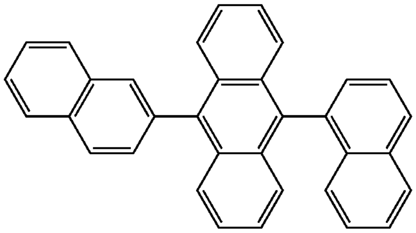

H3

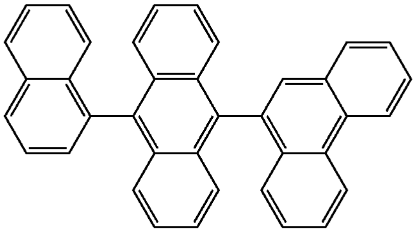

H4

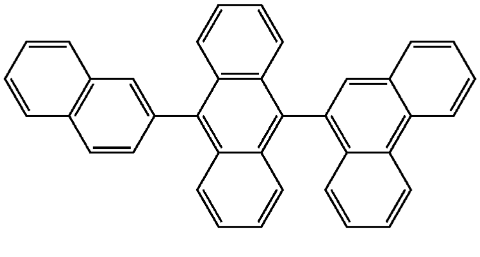

-continued

H5

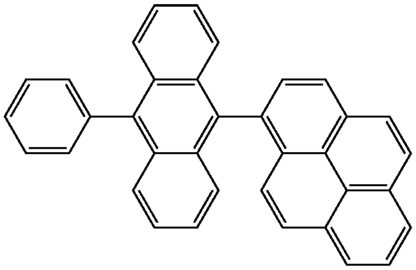

H6

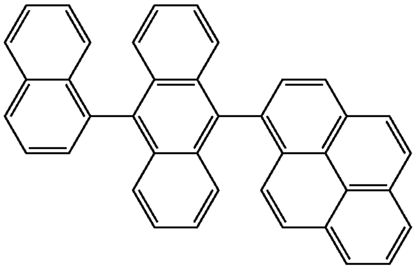

H7

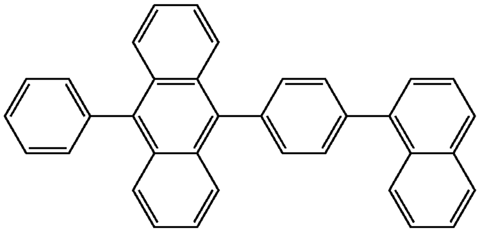

H8

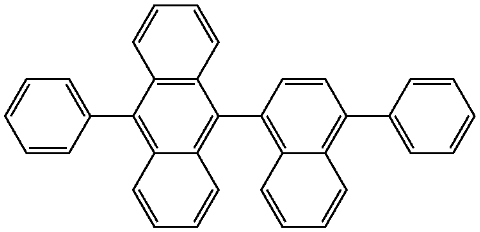

H9

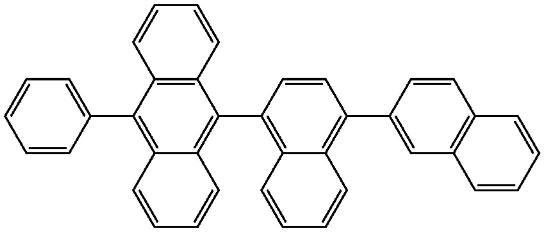

H10

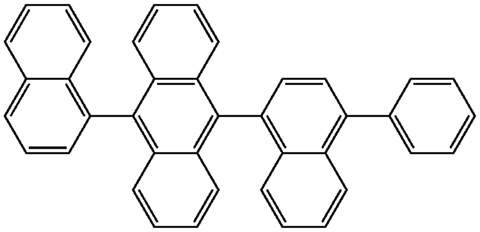

-continued
H11
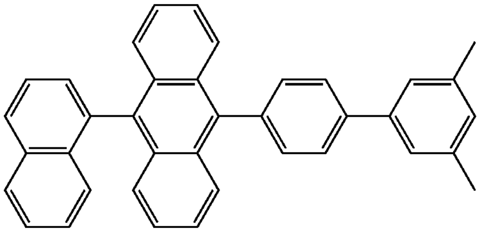
H12
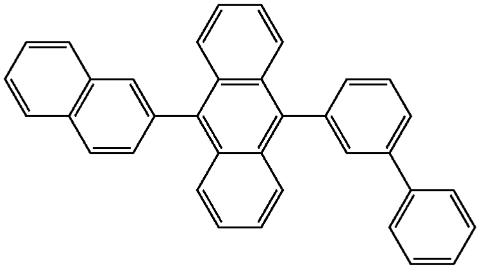
H13
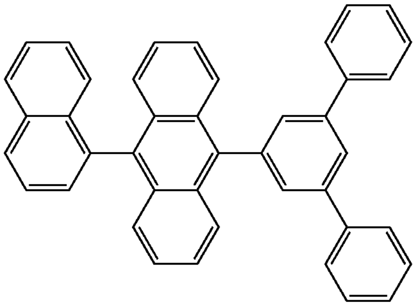
H14
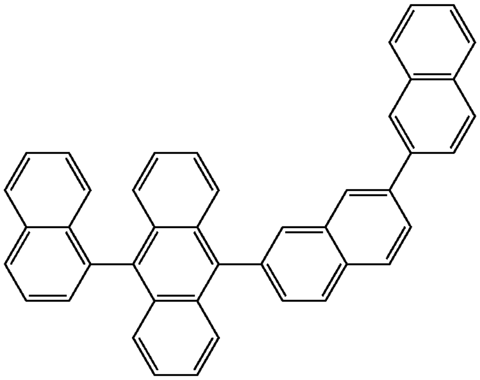
H15
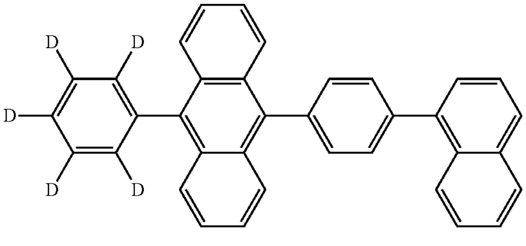
-continued
H16
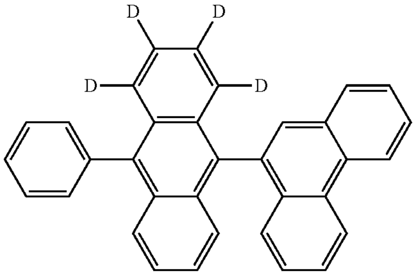
H17
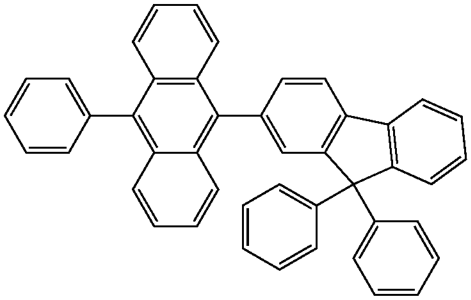
H18
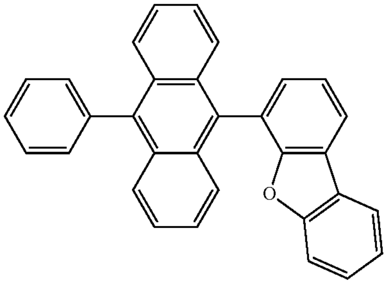
H19
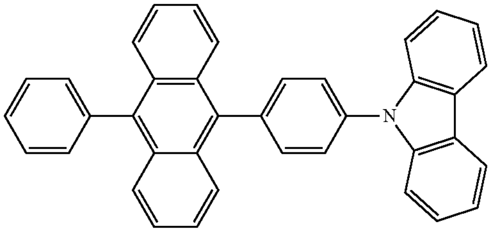
H20
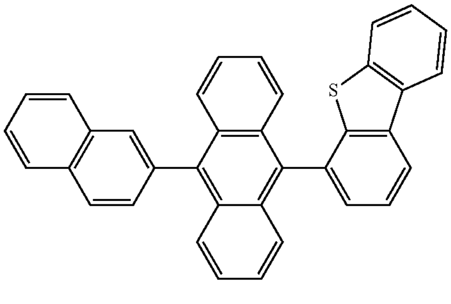

-continued
H21
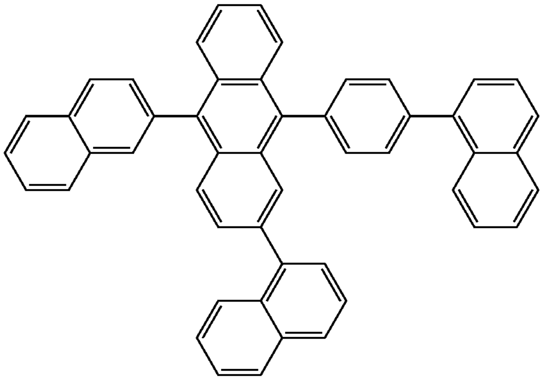
H22
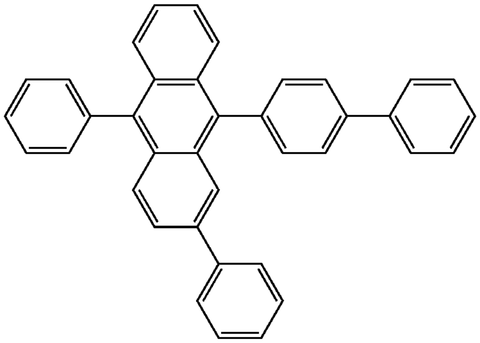
H23
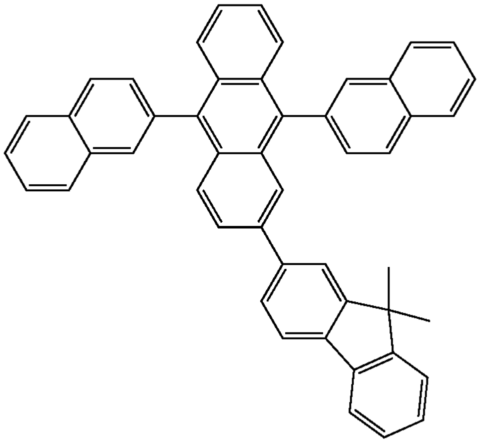
H24
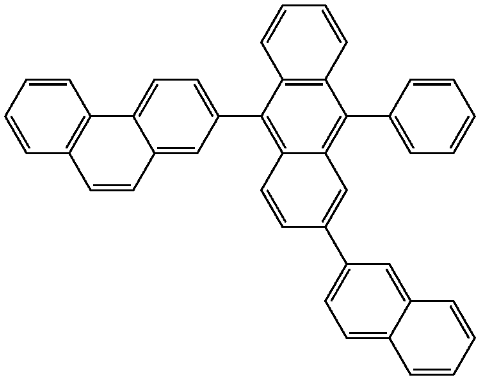
-continued
H25
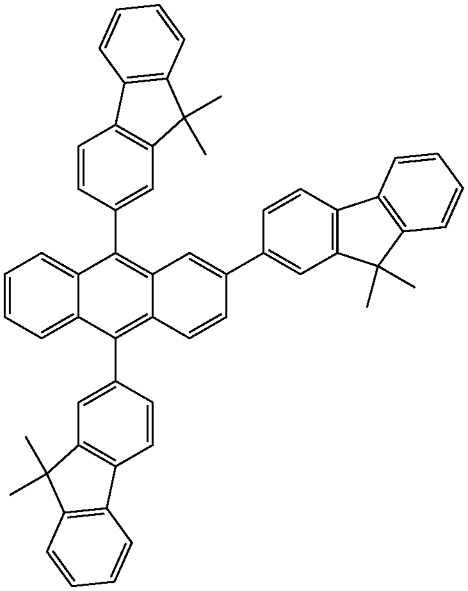
H26
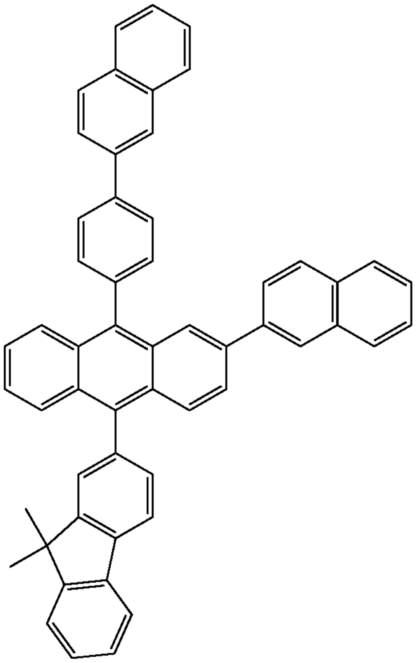

-continued
H27
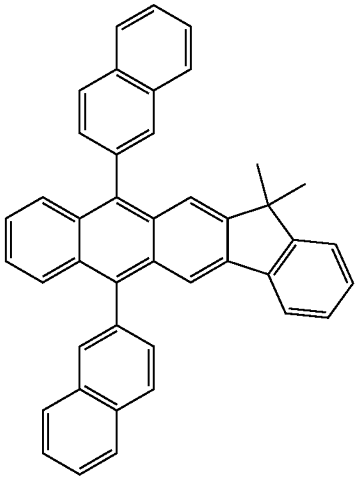
H28
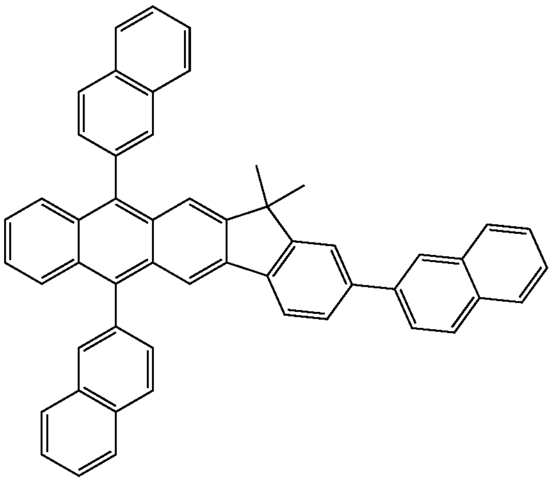
H29
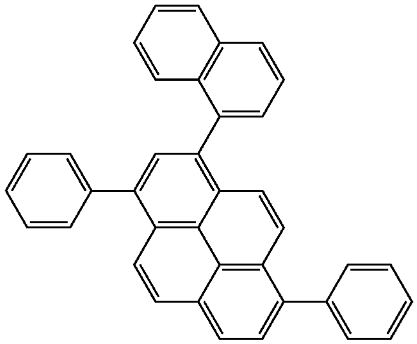
-continued
H30
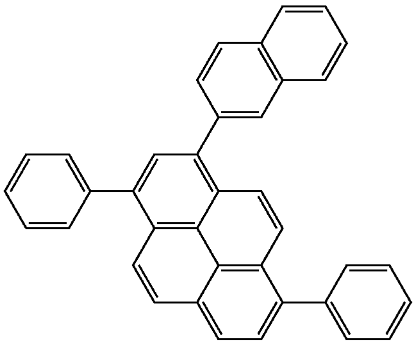
H31
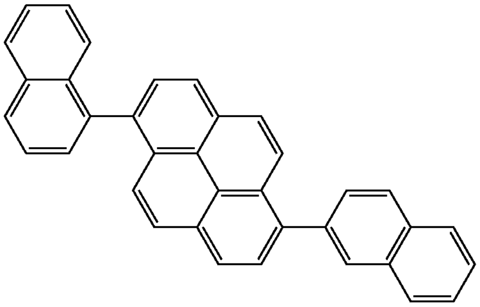
H32
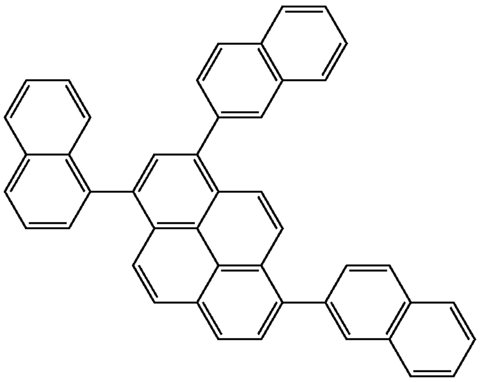
H33
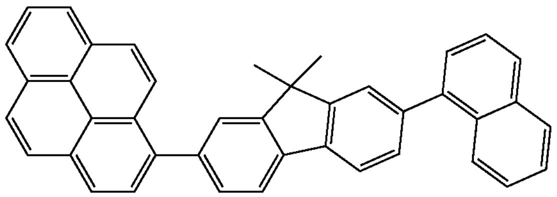
H34
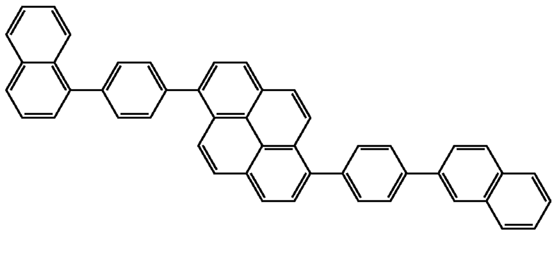

-continued
H35
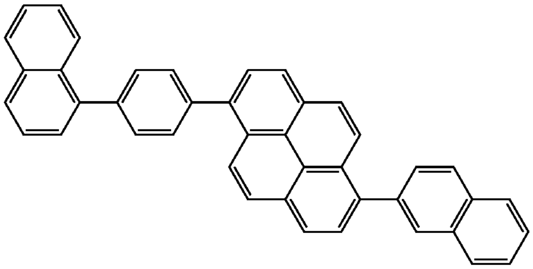
H36
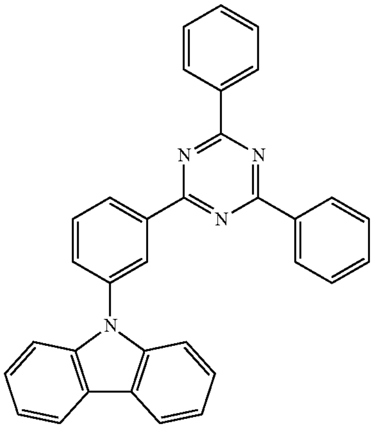
H37
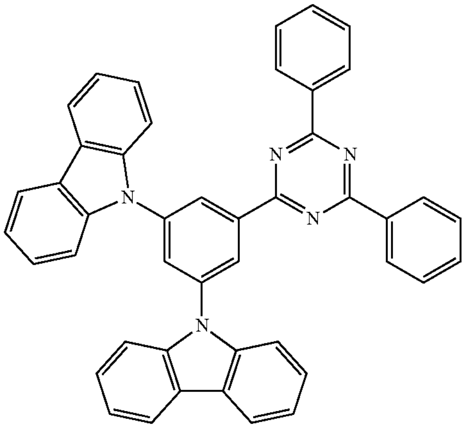
H38
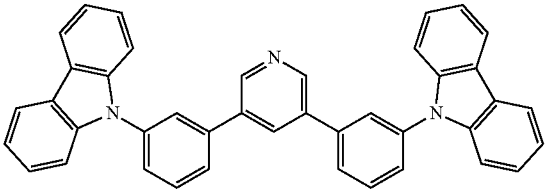
-continued
H39
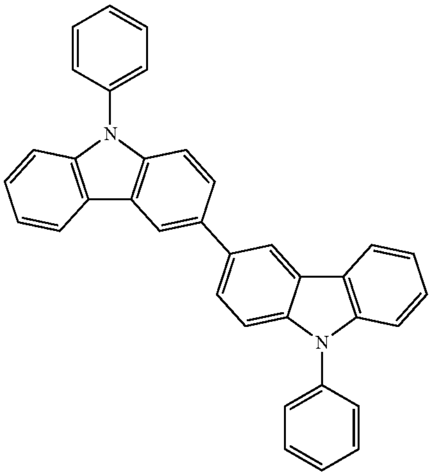
H40
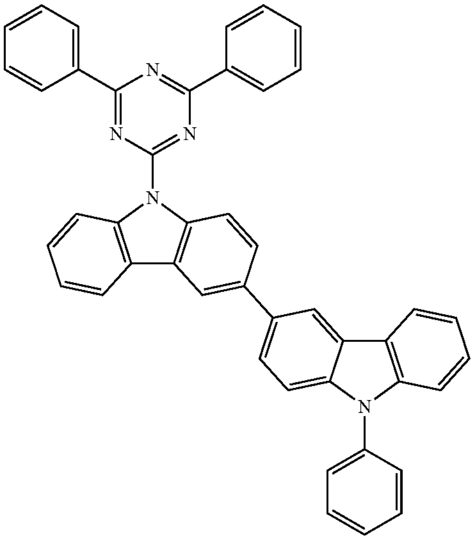
H41
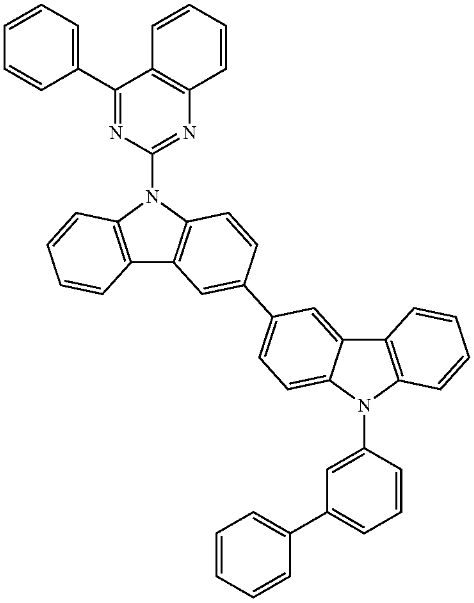

-continued
H42
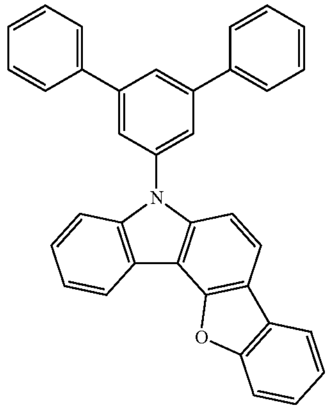
H43
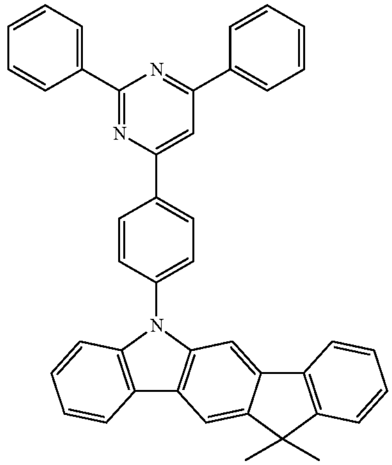
H44
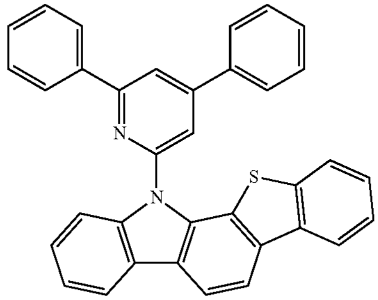
H45
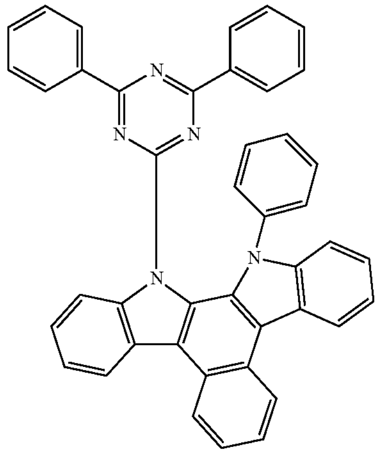
-continued
H46
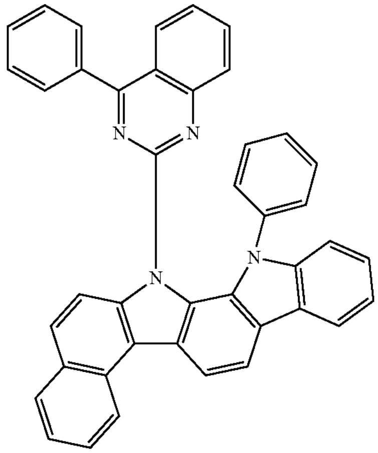
H47
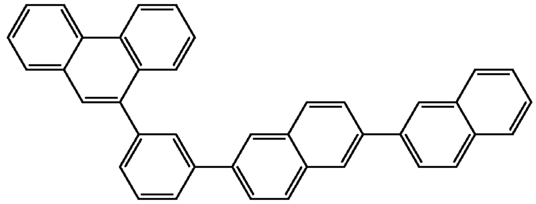
H48
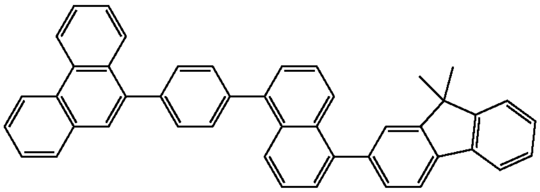
H49
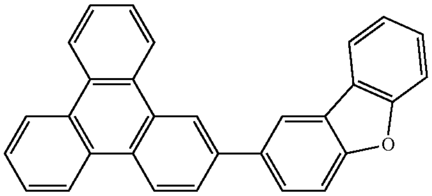
H50
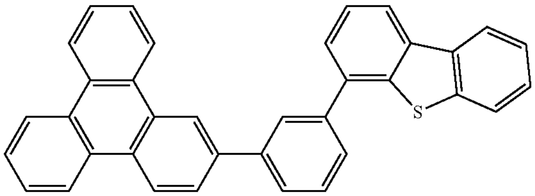
H51
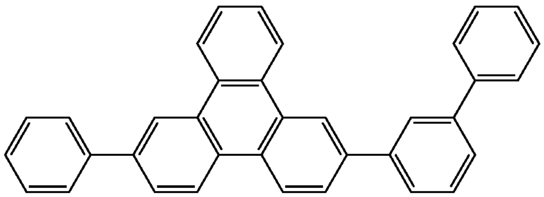

-continued

H52

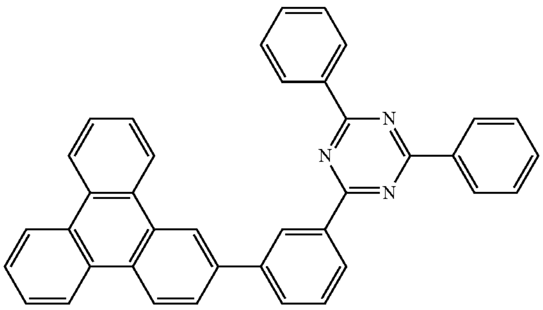

H53

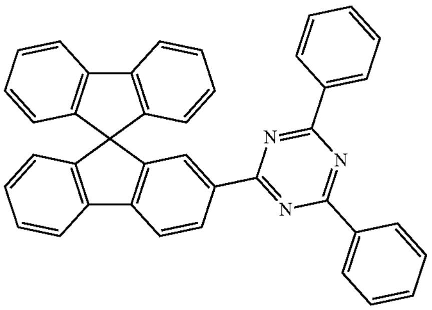

H54

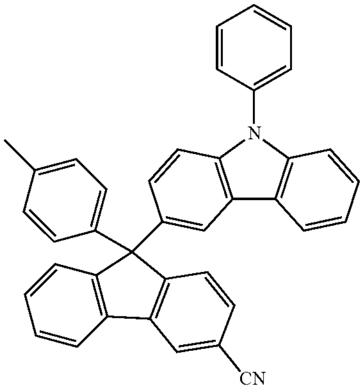

H55

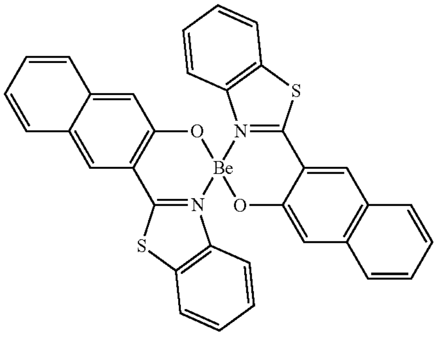

Phosphorescent Dopant Included in Emission Layer of Organic Layer 150

The phosphorescent dopant may include an organometallic complex represented by Formula 401:

$$M(L_{401})_{xc1}(L_{402})_{xc2}$$ Formula 401

Formula 402

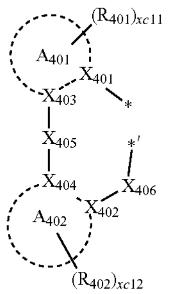

wherein, in Formulae 401 and 402,

M may be selected from iridium (Ir), platinum (Pt), palladium (Pd), osmium (Os), titanium (Ti), zirconium (Zr), hafnium (Hf), europium (Eu), terbium (Tb), rhodium (Rh), and thulium (Tm), $L_{401}$ may be selected from ligands represented by Formula 402, and xc1 may be 1, 2, or 3, and when xc1 is 2 or greater, at least two $L_{401}$(s) may be identical to or different from each other, $L_{402}$ may be an organic ligand, and xc2 may be an integer selected from 0 to 4, and when xc2 is 2 or greater, at least two $L_{402}$(s) may be identical to or different from each other, $X_{401}$ to $X_{404}$ may each independently be a nitrogen or a carbon, $X_{401}$ and $X_{403}$ may be bound to each other via a single bond or a double bond, $X_{402}$ and $X_{404}$ may be bound to each other via a single bond or a double bond, $A_{401}$ and $A_{402}$ may each independently be a $C_5$-$C_{60}$ carbocyclic group or a $C_1$-$C_{60}$ heterocyclic group, $X_{405}$ may be a single bond, *—O—*', *—S—*', *—C(=O)—*', *—N($Q_{411}$)-*', *—C($Q_{411}$)($Q_{412}$)-*', *—C($Q_{411}$)=C($Q_{412}$)-*', *—C($Q_{411}$)=*', or *=C=*', wherein $Q_{411}$ and $Q_{412}$ may each independently be hydrogen, deuterium, a $C_1$-$C_{20}$ alkyl group, a $C_1$-$C_{20}$ alkoxy group, a phenyl group, a biphenyl group, a terphenyl group, or a naphthyl group, $X_{406}$ may be a single bond, O, or S, $R_{401}$ and $R_{402}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{20}$ alkyl group, a substituted or unsubstituted $C_1$-$C_{20}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{401}$)($Q_{402}$)($Q_{403}$), —N($Q_{401}$)

$(Q_{402})$, —$B(Q_{401})(Q_{402})$, —C(═O)$(Q_{401})$, —S(═O)$_2$$(Q_{401})$, and —P(═O)$(Q_{401})(Q_{402})$, wherein $Q_{401}$ to $Q_{403}$ may each independently be selected from a $C_1$-$C_{10}$ alkyl group, a $C_1$-$C_{10}$ alkoxy group, a $C_6$-$C_{20}$ aryl group, and a $C_1$-$C_{20}$ heteroaryl group, xc11 and xc12 may each independently be an integer from 0 to 10, and

* and *' in Formula 402 each indicate a binding site to M in Formula 401.

In some embodiments, in Formula 402, $A_{401}$ and $A_{402}$ may each independently be selected from a benzene group, a naphthalene group, a fluorene group, a spiro-bifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, and a dibenzothiophene group.

In one or more embodiments, in Formula 402, i) $X_{401}$ may be nitrogen, and $X_{402}$ may be carbon, or ii) $X_{401}$ and $X_{402}$ may each be nitrogen.

In an embodiment, in Formula 402, $R_{401}$ and $R_{402}$ may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a phenyl group, a naphthyl group, a cyclopentyl group, a cyclohexyl group, an adamantyl group, a norbornanyl group, and a norbornenyl group;

a cyclopentyl group, a cyclohexyl group, an adamantyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group;

a cyclopentyl group, a cyclohexyl group, an adamantyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, an adamantyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group; and —$Si(Q_{401})(Q_{402})(Q_{403})$, —$N(Q_{401})(Q_{402})$, —$B(Q_{401})(Q_{402})$, —C(═O)$(Q_{401})$, —S(═O)$_2$$(Q_{401})$, and —P(═O)$(Q_{401})(Q_{402})$, wherein $Q_{401}$ to $Q_{403}$ may each independently be selected from a $C_1$-$C_{10}$ alkyl group, a $C_1$-$C_{10}$ alkoxy group, a phenyl group, a biphenyl group, and a naphthyl group, but embodiments are not limited thereto.

In one or more embodiments, when xc1 in Formula 401 is 2 or greater, two $A_{401}$(s) of at least two $L_{401}$(s) may optionally be linked via $X_{407}$ as a linking group; or two $A_{402}$(s) may optionally be linked via $X_{408}$ as a linking group (see Compounds PD1 to PD4 and PD7 herein). $X_{407}$ and $X_{408}$ may each independently be selected from a single bond, *—O—*', *—S—*', *—C(═O)—*', *—$N(Q_{413})$-*', *—$C(Q_{413})(Q_{414})$-*, and *—$C(Q_{413})$═$C(Q_{414})$-*, wherein $Q_{413}$ and $Q_{414}$ may each independently be hydrogen, deuterium, a $C_1$-$C_{20}$ alkyl group, a $C_1$-$C_{20}$ alkoxy group, a phenyl group, a biphenyl group, a terphenyl group, or a naphthyl group, but embodiments are not limited thereto.

$L_{402}$ in Formula 401 may be any suitable monovalent, divalent, or trivalent organic ligand. For example, $L_{402}$ may be selected from halogen, diketone (e.g., acetylacetonate), a carboxylic acid (e.g., picolinate), —C(═O), isonitrile, —CN, and phosphorus (e.g., phosphine or phosphite), but embodiments are not limited thereto.

In some embodiments, the phosphorescent dopant may include, for example, at least one selected from Compounds PD1 to PD25, but embodiments are not limited thereto:

PD1

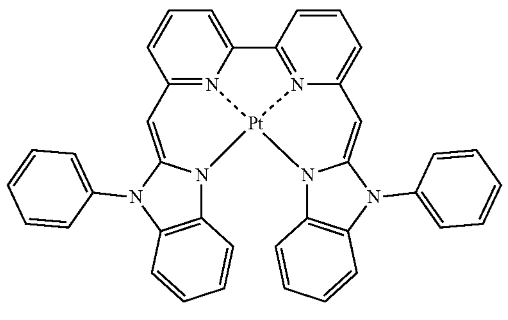

PD2

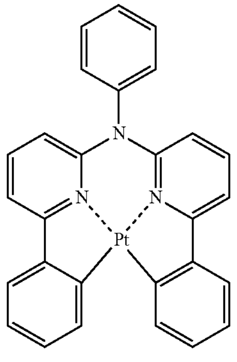

-continued
PD3
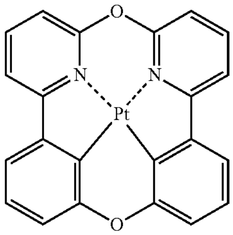
PD4
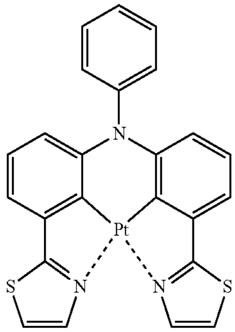
PD5
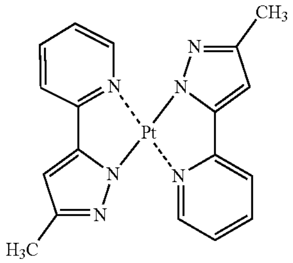
PD6
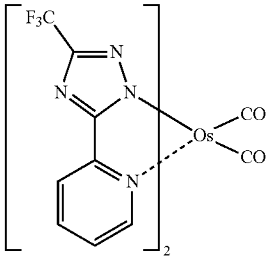
PD7
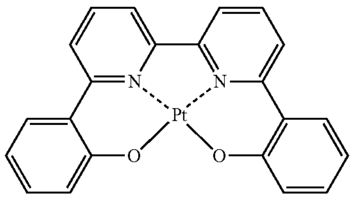
PD8
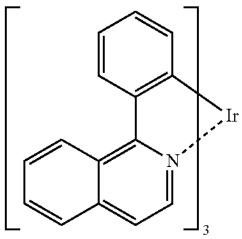
-continued
PD9
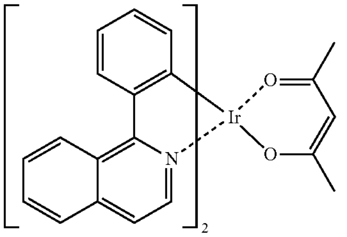
PD10
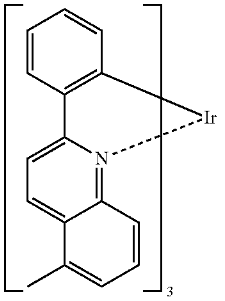
PD11
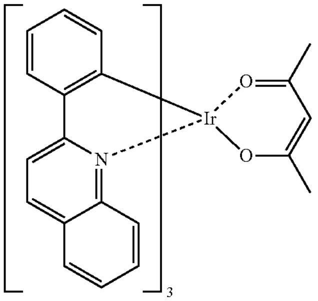
PD12
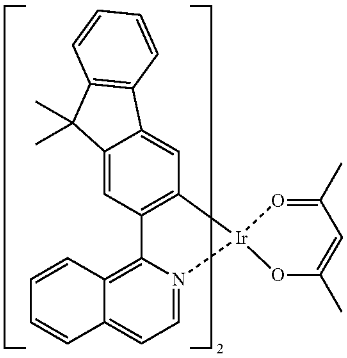
PD13
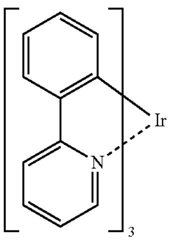

-continued
PD14
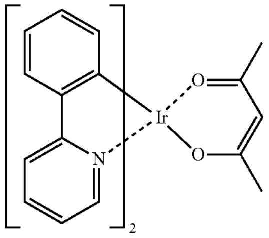
PD15
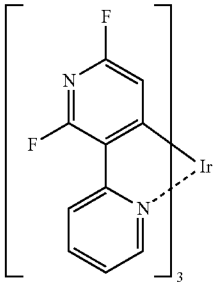
PD16
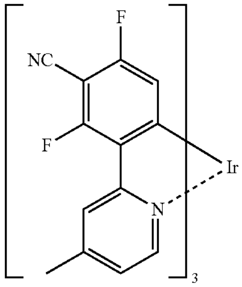
PD17
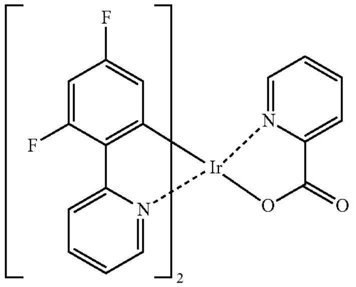
PD18
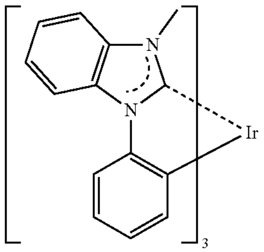
-continued
PD19
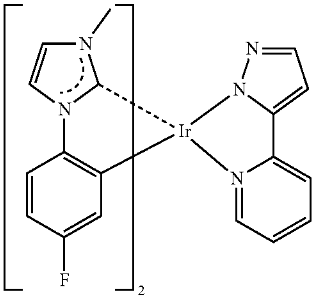
PD20
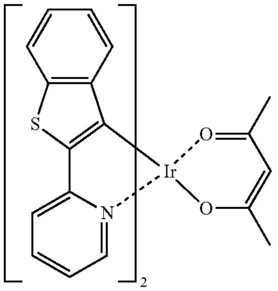
PD21
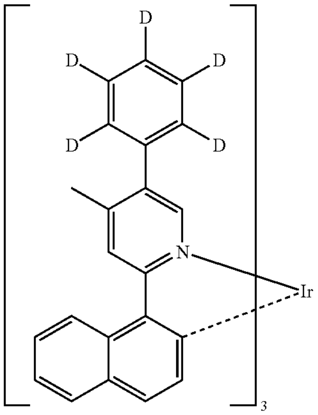
PD22
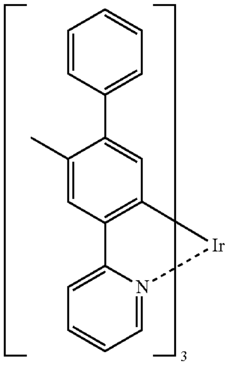

-continued

PD23

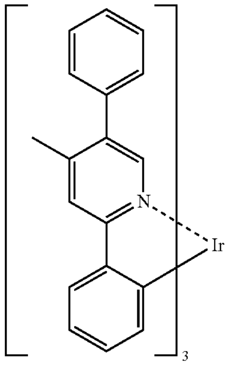

PD24

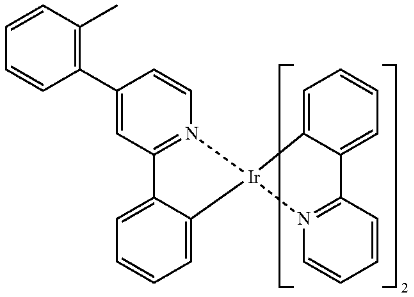

PD25

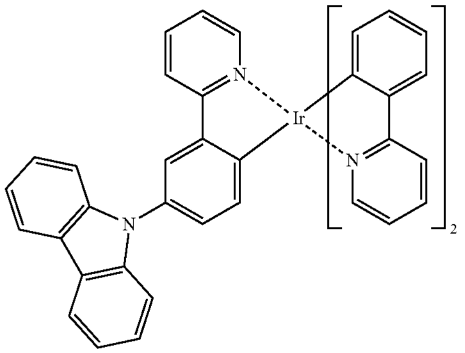

Fluorescent Dopant in Emission Layer

In some embodiments, the fluorescent dopant may include a heterocyclic compound represented by Formula 1:

The fluorescent dopant may further include an arylamine compound or a styrylamine compound.

In some embodiments, the fluorescent dopant may further include a compound represented by Formula 501:

Formula 501

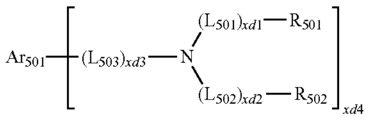

wherein, in Formula 501, $Ar_{501}$ may be selected from a substituted or unsubstituted $C_5$-$C_{60}$ carbocyclic group and a substituted or unsubstituted $C_1$-$C_{60}$ heterocyclic group, $L_{501}$ to $L_{503}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xd1 to xd3 may each independently be an integer from 0 to 3, $R_{501}$ and $R_{502}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and xd4 may be an integer from 1 to 6.

In some embodiments, in Formula 501, $Ar_{501}$ may be selected from:

a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group; and a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In an embodiment, in Formula 501, $L_{501}$ and $L_{503}$ may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

In an embodiment, in Formula 501, $R_{501}$ and $R_{502}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —Si($Q_{31}$)($Q_{32}$)($Q_{33}$), wherein $Q_{31}$ to $Q_{33}$ may be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xd4 in Formula 501 may be 2, but embodiments are not limited thereto.

In some embodiments, the fluorescent dopant may be selected from Compounds FD1 to FD22:

FD1

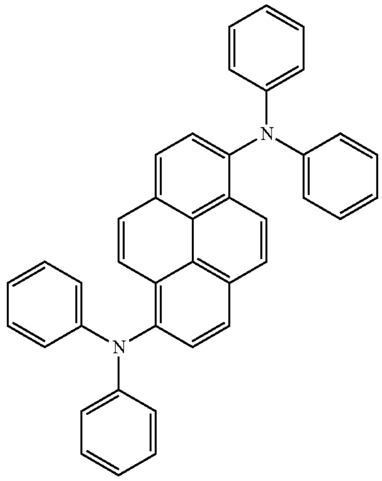

FD2

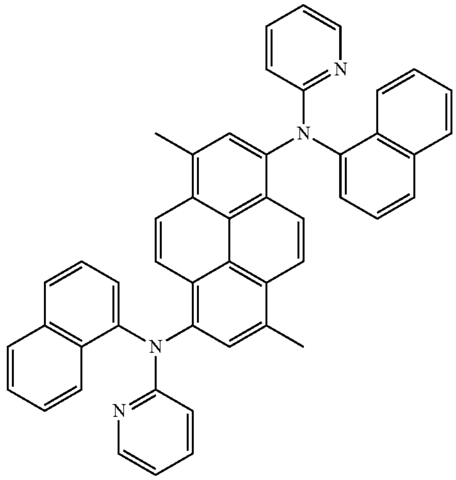

-continued
FD3
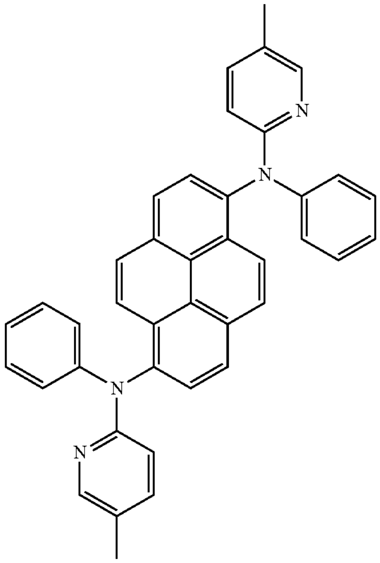
FD4
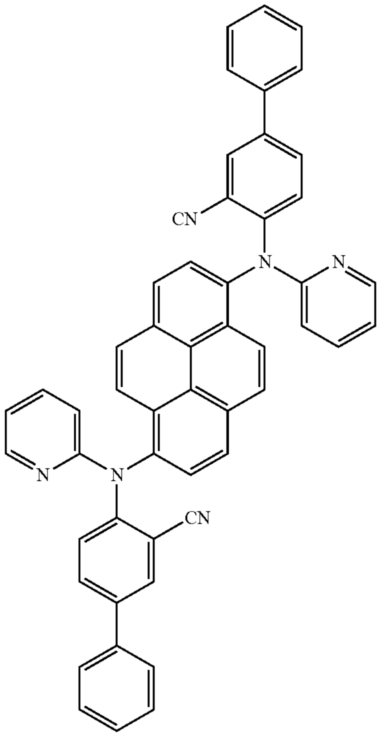
-continued
FD5
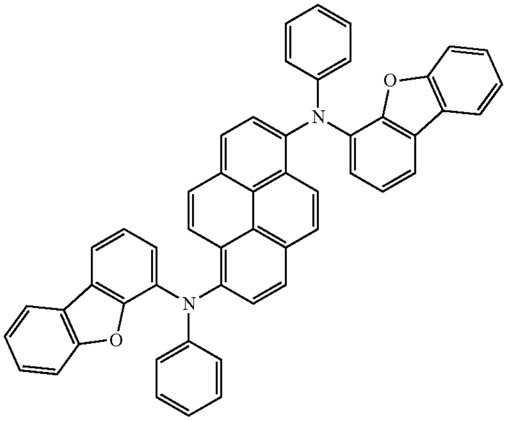
FD6
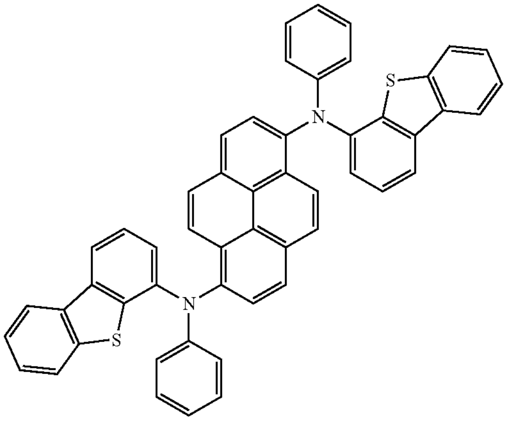
FD7
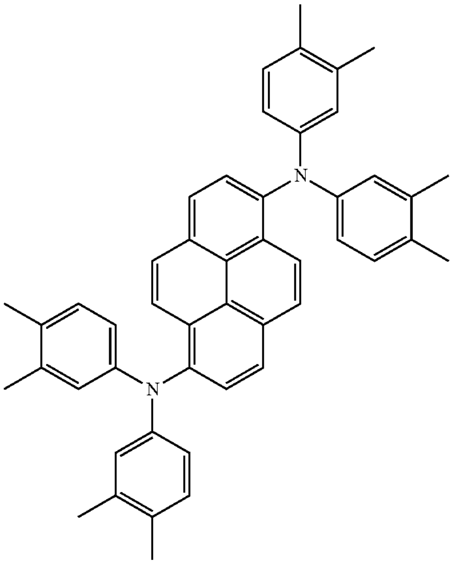

-continued
FD8
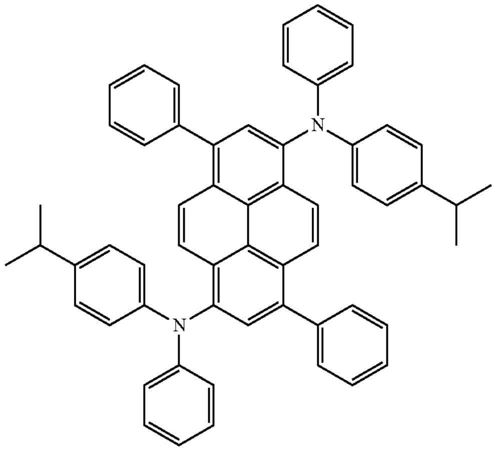
FD9
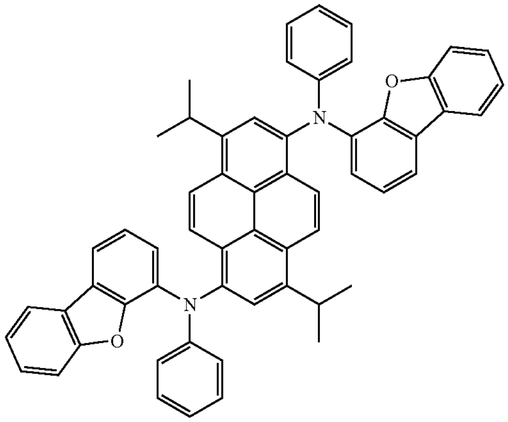
FD10
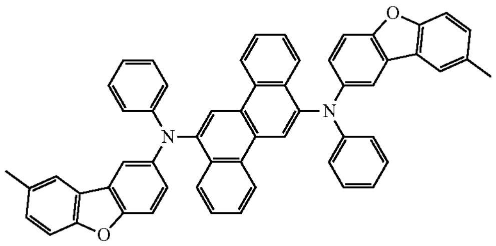
FD11
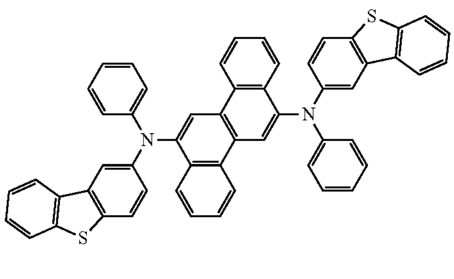
-continued
FD12
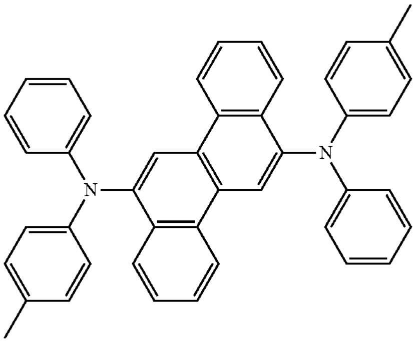
FD13
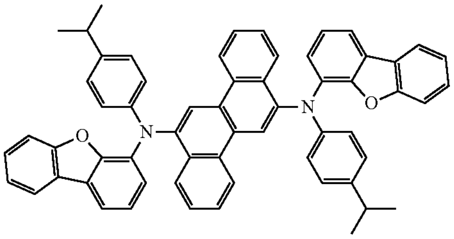
FD14
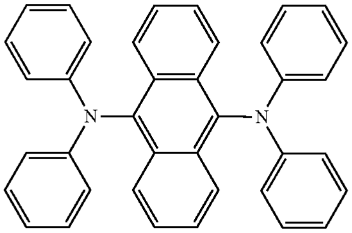
FD15
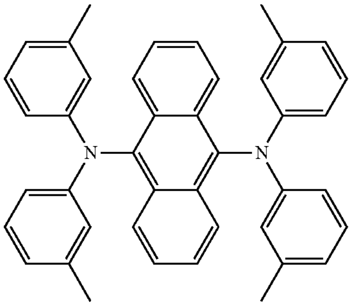
FD16
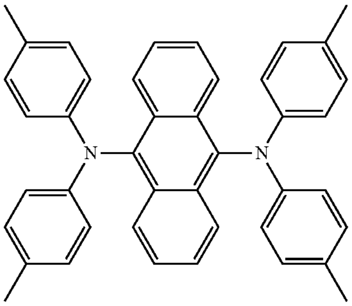

-continued
FD17
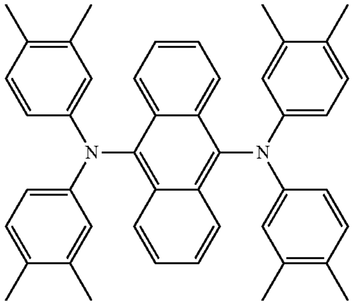
FD18
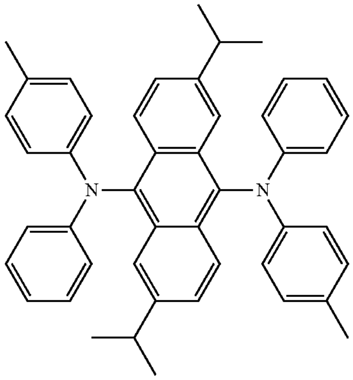
FD19
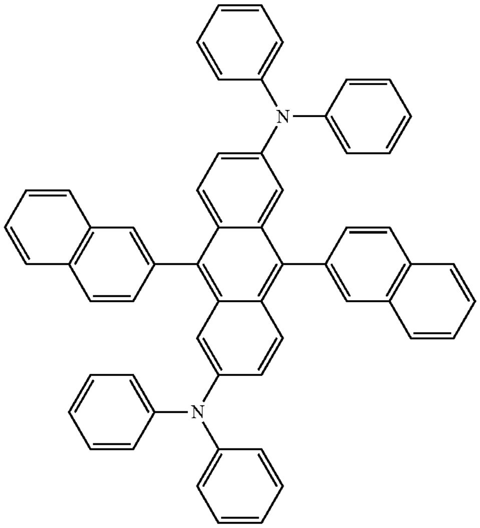
-continued
FD20
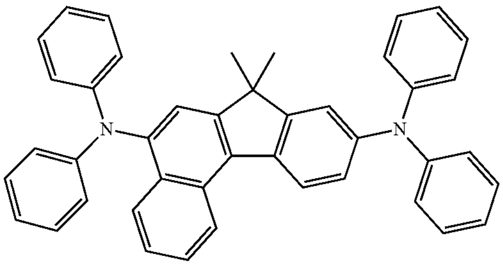
FD21
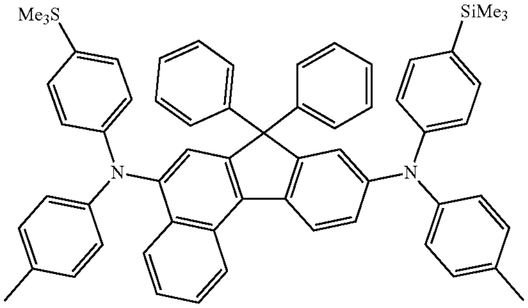
FD22
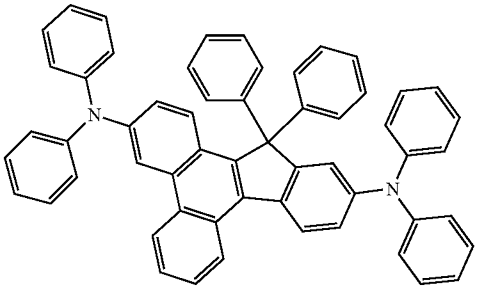
In some embodiments, the fluorescent dopant may be selected from the following compounds, but embodiments are not limited thereto:
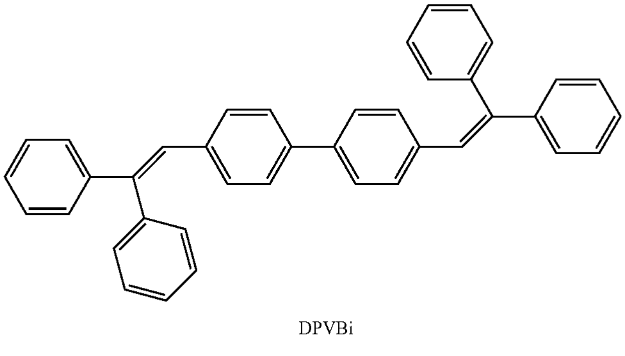
DPVBi -continued

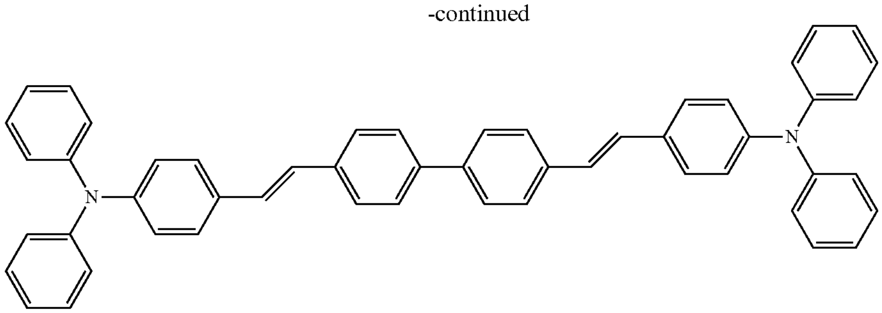

DPAVBi

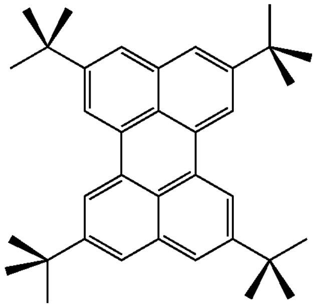

TBPe

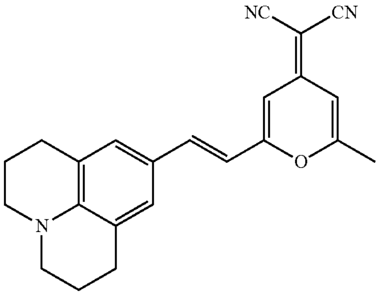

DCM

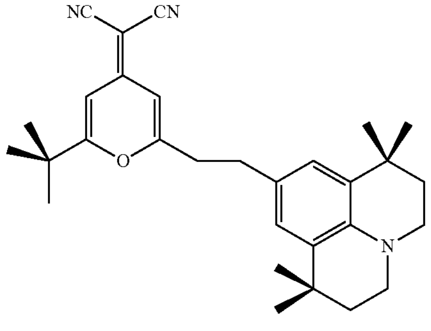

DCJTB

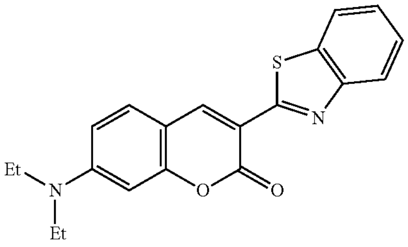

Coumarin 6

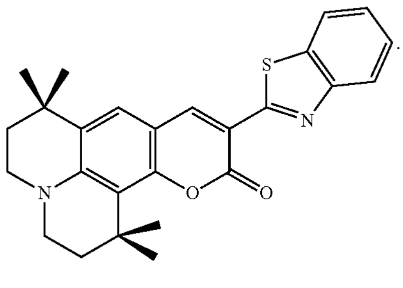

C545T

Quantum Dot

The emission layer included in the organic light-emitting device of embodiments of the present disclosure may include a quantum dot material.

The quantum dot is a particle having a crystal structure of several to tens of nanometers in size. The quantum dot may include hundreds to thousands of atoms.

Because the quantum dot is very small in size, a quantum confinement effect may occur. The quantum confinement effect is a phenomenon in which a band gap of an object becomes larger when the object becomes smaller than a nanometer size. Accordingly, when light of a wavelength having an energy larger than a band gap of the quantum dot is incident on the quantum dot, the quantum dot is excited by absorbing the light, emits light of a set or specific wavelength, and falls to the ground state. In this case, the wavelength of the emitted light may have a value corresponding to the band gap.

A core of the quantum dot may include a Group II-VI compound, a Group III-VI compound, a Group III-V compound, a Group IV-VI compound, a Group IV element or compound, a Group I-III-VI compound, or a combination thereof.

The Group II-VI compound may be selected from a binary compound selected from the group consisting of CdS, CdSe, CdTe, ZnS, ZnSe, ZnTe, ZnO, HgS, HgSe, HgTe, MgSe, MgS, and a mixture thereof; a ternary compound selected from the group consisting of CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, and a mixture thereof; and a quaternary compound selected from the group consisting of CdZnSeS, CdZnSeTe, CdZnSTe, CdHgSeS, CdHgSeTe, CdHgSTe, HgZnSeS, HgZnSeTe, HgZnSTe, and a mixture thereof.

The Group III-VI compound may include a binary compound such as $In_2S_3$ and/or $In_2Se_3$; a ternary compound such as $InGaS_3$ and/or $InGaSe_3$; or any combination thereof.

The Group III-V compound may be selected from a binary compound selected from the group consisting of GaN, GaP, GaAs, GaSb, AlN, AlP, AlAs, AlSb, InN, InP, InAs, InSb and a mixture thereof; a ternary compound selected from the group consisting of GaNP, GaNAs, GaNSb, GaPAs, GaPSb, AlNP, AlNAs, AlNSb, AlPAs, AlPSb, InGaP, InAlP, InNP, InNAs, InNSb, InPAs, InPSb, GaAlNP, and a mixture thereof; and a quaternary compound selected from the group consisting of GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, and a mixture thereof. The Group III-V semiconductor compound may further include a Group II metal (e.g., InZnP).

The Group IV-VI compound may be selected from a binary compound selected from the group consisting of SnS, SnSe, SnTe, PbS, PbSe, PbTe, and a mixture thereof; a ternary compound selected from the group consisting of SnSeS, SnSeTe, SnSTe, PbSeS, PbSeTe, PbSTe, SnPbS, SnPbSe, SnPbTe, and a mixture thereof; and a quaternary compound selected from the group consisting of SnPbSSe, SnPbSeTe, SnPbSTe, and a mixture thereof. The Group IV element may be selected from the group consisting of Si, Ge, and a mixture thereof. The IV compound may be a binary compound selected from the group consisting of SiC, SiGe, and a mixture thereof.

In this embodiment, the binary compound, the ternary compound, or the quaternary compound may be present in particles at a uniform (e.g., substantially uniform) concentration or in the same particle by being partially divided into different concentrations. In addition, one quantum dot may have a core-shell structure surrounding another quantum dot. An interface between a core and a shell may have a concentration gradient where a concentration of elements present in the shell decreases along a direction toward the core.

In some embodiments, the quantum dot may have a core-shell structure including a core including the nanocrystals described above and a shell surrounding the core. The shell of the quantum dot may serve as a protective layer for preventing or reducing chemical denaturation of the core to maintain semiconductor characteristics and/or as a charging layer for imparting electrophoretic characteristics to the quantum dot. The shell may be monolayer or multilayer. An interface between a core and a shell may have a concentration gradient where a concentration of elements present in the shell decreases along a direction toward the core. Examples of the shell of the quantum dot include metal and/or nonmetal oxide, a semiconductor compound, or a combination thereof.

In some embodiments, the metal or nonmetal oxide may be a binary compound such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $CO_3O_4$, and/or NiO or a ternary compound such as $MgAl_2O_4$, $CoFe_2O_4$, $NiFe_2O_4$, and/or $CoMn_2O_4$, but embodiments are not limited thereto.

In addition, the semiconductor compound may be CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, and/or AlSb, but embodiments are not limited thereto.

The quantum dot may have a full width of half maximum (FWHM) of an emission wavelength spectrum of about 45 nm or less, about 40 nm or less, or about 30 nm or less. When the FWHM of the emission wavelength spectrum of the quantum dot is within any of the foregoing ranges, color purity or color reproducibility may be improved. In addition, because light emitted through the quantum dot is emitted in all directions, an optical viewing angle may be improved.

In addition, the form of the quantum dot may be any suitable form generally used in the art and is not particularly limited. The quantum dot may have a spherical form, a pyramidal form, a multi-armed form, or a cubic nanoparticle, a nanotube, a nanowire, a nanofiber, a nano-plate particle, or the like.

The quantum dot may control color of emitted light according to the particle size. Accordingly, the quantum dot may have various suitable emission colors such as blue, red, or green.

Electron Transport Region in Organic Layer 150

The electron transport region may have i) a single-layered structure including (e.g., consisting of) a single layer including (e.g., consisting of) a single material, ii) a single-layered structure including (e.g., consisting of) a single layer including a plurality of different materials, or iii) a multi-layered structure each having a plurality of layers, each having a plurality of different materials.

The electron transport region may include at least one selected from a buffer layer, a hole blocking layer, an electron control layer, an electron transport layer, and an electron injection layer, but embodiments are not limited thereto.

In some embodiments, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein layers of each structure are sequentially stacked on the emission layer in each stated order, but embodiments are not limited thereto.

The electron transport region (e.g., the buffer layer, the hole blocking layer, the electron control layer, the electron transport layer, and/or the electron injection layer in the electron transport region) may include a heterocyclic compound represented by Formula 1.

In some embodiments, the electron transport region may include the heterocyclic compound represented by Formula 1 and may further include a metal-free compound containing at least one π electron-depleted nitrogen-containing ring.

The term "π electron-depleted nitrogen-containing ring," as used herein, refers to a $C_1$-$C_{60}$ heterocyclic group having at least one $*—N=*'$ moiety as a ring-forming moiety.

For example, the "π electron-depleted nitrogen-containing ring" may be i) a 5-membered to 7-membered heteromonocyclic group having at least one $*—N=*'$ moiety, ii) a heteropolycyclic group in which at least two 5-membered to 7-membered heteromonocyclic groups, each having at least one $*—N=*'$ moiety, are condensed, or iii) a heteropolycyclic group in which at least one of a 5-membered to 7-membered heteromonocyclic group, each having at least one $*—N=*'$ moiety, is condensed with (e.g., combined together with) at least one $C_5$-$C_{60}$ carbocyclic group.

Examples of the π electron-depleted nitrogen-containing ring may include imidazole, pyrazole, thiazole, isothiazole, oxazole, isoxazole, pyridine, pyrazine, pyrimidine, pyridazine, indazole, purine, quinoline, isoquinoline, benzoquinoline, phthalazine, naphthyridine, quinoxaline, quinazoline, cinnoline, phenanthridine, acridine, phenanthroline, phenazine, benzimidazole, isobenzothiazole, benzoxazole, isobenzoxazole, triazole, tetrazole, oxadiazole, triazine, thiadiazole, imidazopyridine, imidazopyrimidine, and azacarbazole, but embodiments are not limited thereto.

In some embodiments, the electron transport region may include a compound represented by Formula 601:

$$[Ar_{601}]_{xe11}\text{-}[(L_{601})_{xe1}\text{-}R_{601}]_{xe21} \quad \text{Formula 601}$$

wherein, in Formula 601, $Ar_{601}$ may be selected from a substituted or unsubstituted $C_5$-$C_{60}$ carbocyclic group and a substituted or unsubstituted $C_1$-$C_{60}$ heterocyclic group, xe11 may be 1, 2, or 3, $L_{601}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xe1 may be an integer from 0 to 5, $R_{601}$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$Si(Q_{601})(Q_{602})(Q_{603})$, —$C(=O)(Q_{601})$, —$S(=O)_2(Q_{601})$, and —$P(=O)(Q_{601})(Q_{602})$, wherein $Q_{601}$ to $Q_{603}$ may each independently be a $C_1$-$C_{10}$ alkyl group, a $C_1$-$C_{10}$ alkoxy group, a phenyl group, a biphenyl group, a terphenyl group, or a naphthyl group, and xe21 may be an integer from 1 to 5.

In some embodiments, at least one selected from $Ar_{601}$(s) in the number of xe11 and $R_{601}$(s) in the number of xe21 may include the π electron-depleted nitrogen-containing ring.

In some embodiments, in Formula 601, $Ar_{601}$ may be selected from:

a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group; and a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —$Si(Q_{31})(Q_{32})(Q_{33})$, —$S(=O)_2(Q_{31})$, and —$P(=O)(Q_{31})(Q_{32})$, wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

When xe11 in Formula 601 is 2 or greater, at least two $Ar_{601}$(s) may be bound via a single bond.

In one or more embodiments, $Ar_{601}$ in Formula 601 may be an anthracene group.

In some embodiments, the compound represented by Formula 601 may be represented by Formula 601-1:

Formula 601-1

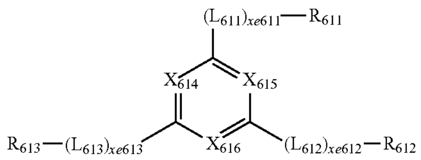

wherein, in Formula 601-1, $X_{614}$ may be N or $C(R_{614})$, $X_{615}$ may be N or $C(R_{615})$, $X_{616}$ may be N or $C(R_{616})$, at least one selected from $X_{614}$ to $X_{616}$ may be N, $L_{611}$ to $L_{613}$ may each independently be understood by referring to the description of $L_{601}$ provided herein, xe611 to xe613 may each independently be understood by referring to the description of xe1 provided herein, $R_{611}$ to $R_{613}$ may each independently be understood by referring to the description of $R_{601}$ provided herein, and $R_{614}$ to $R_{616}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In some embodiments, in Formulae 601 and 601-1, $L_{601}$ and $L_{611}$ to $L_{613}$ may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, but embodiments are not limited thereto.

In one or more embodiments, in Formulae 601 and 601-1, xe1 and xe611 to xe613 may each independently be 0, 1, or 2.

In one or more embodiments, in Formulae 601 and 601-1, $R_{601}$ and $R_{611}$ to $R_{613}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and $—S(=O)_2(Q_{601})$ and $—P(=O)(Q_{601})(Q_{602})$, wherein $Q_{601}$ and $Q_{602}$ may respectively be understood by referring to the descriptions of $Q_{601}$ and $Q_{602}$ provided herein.

The electron transport region may include at least one compound selected from Compounds ET1 to ET36, but embodiments are not limited thereto:

ET1

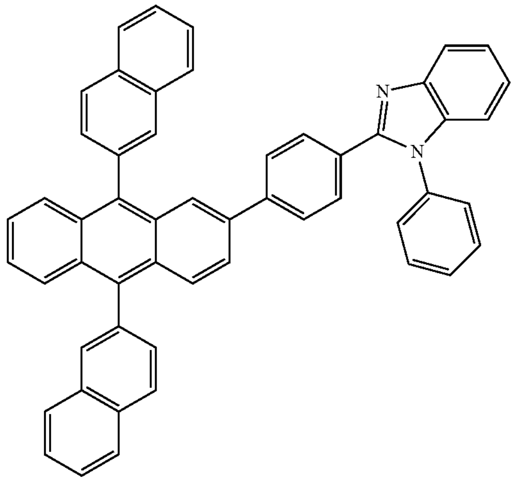

ET2

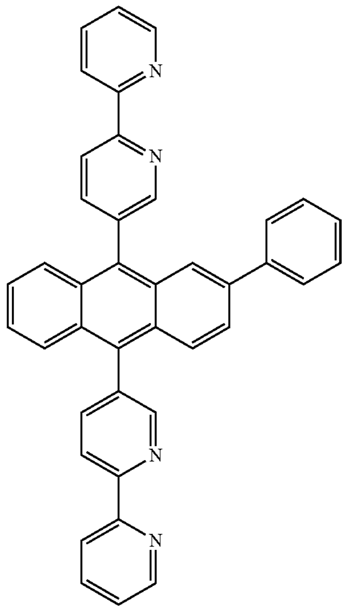

-continued
ET3
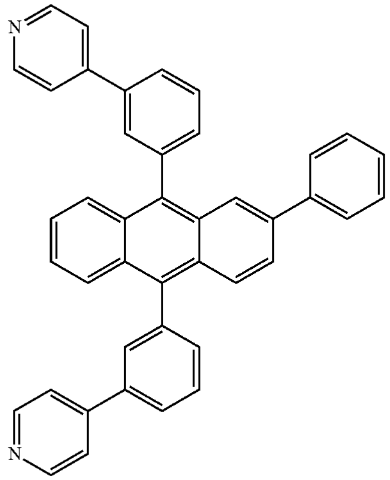
ET4
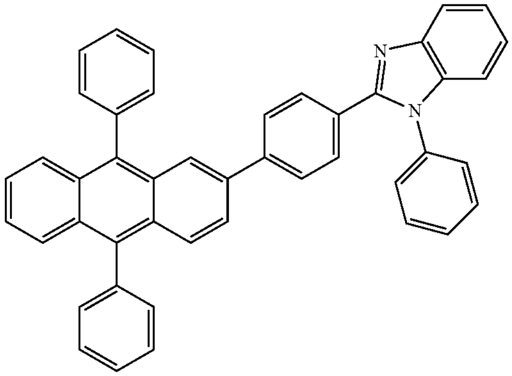
ET5
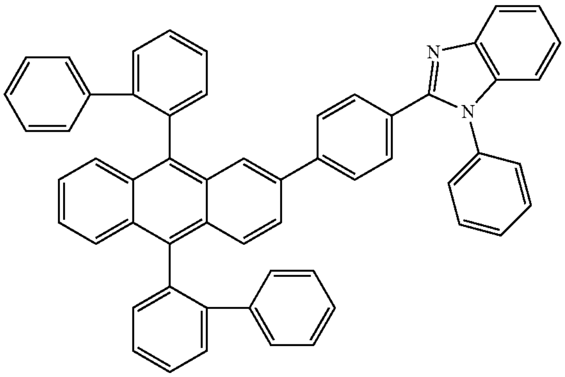
-continued
ET6
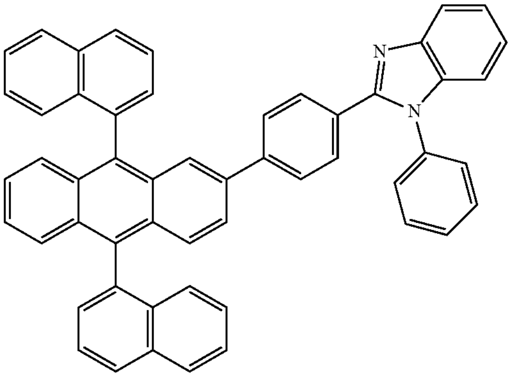
ET7
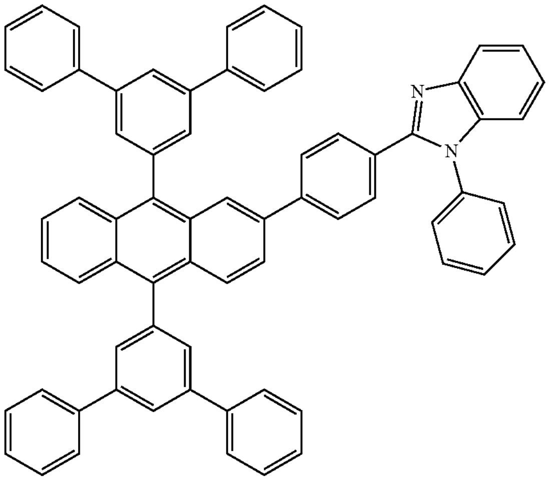
ET8
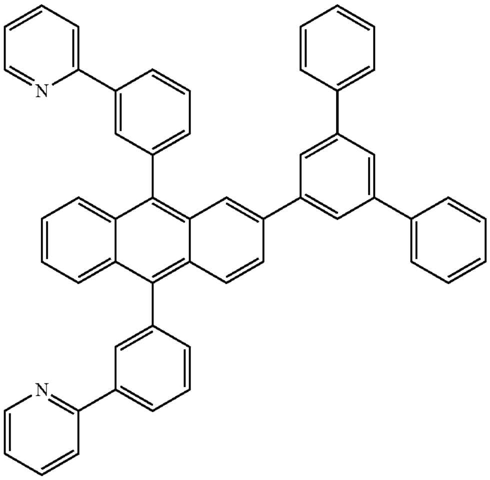

-continued
ET9
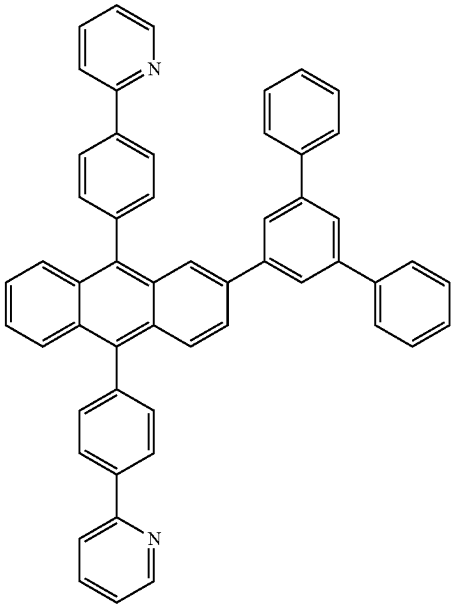
ET10
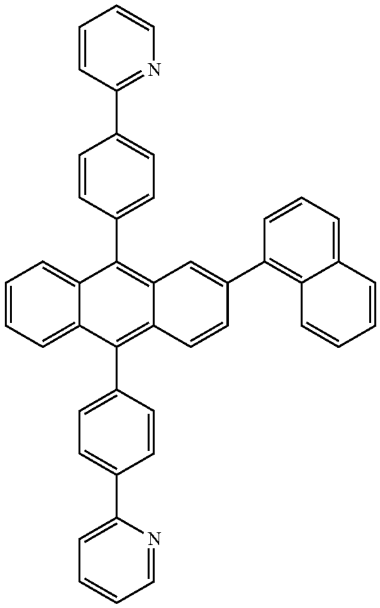
-continued
ET11
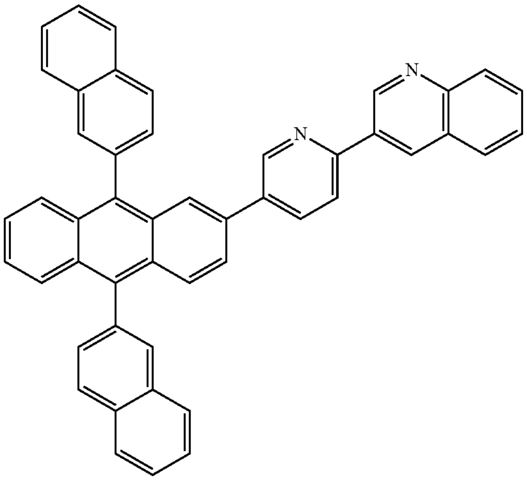
ET12
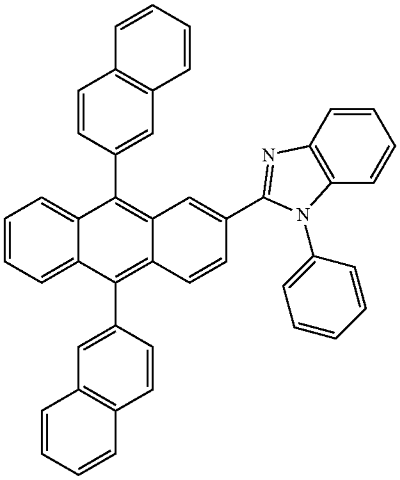
ET13
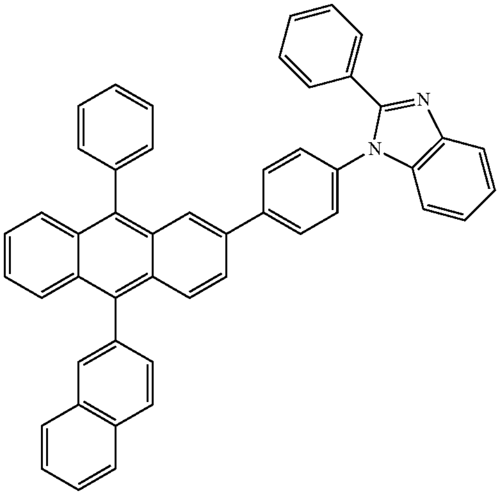

-continued
ET14
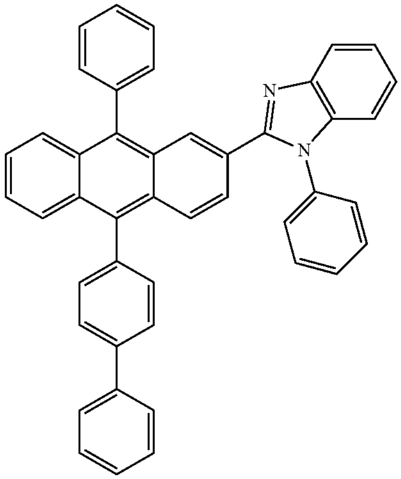
ET15
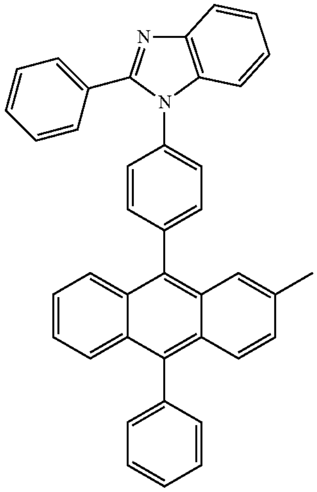
ET16
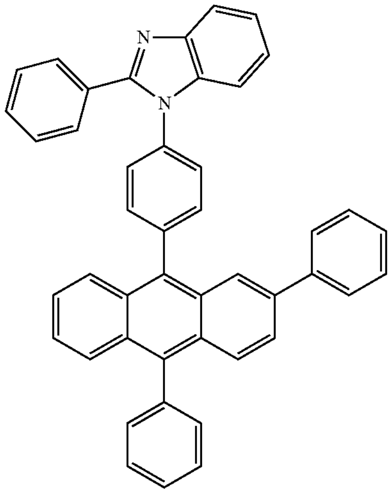
-continued
ET17
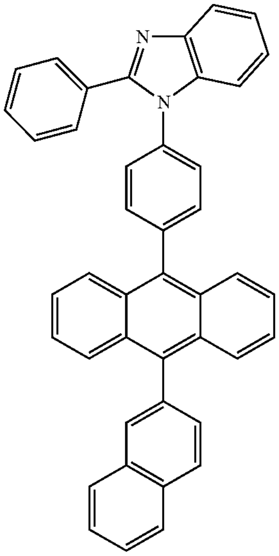
ET18
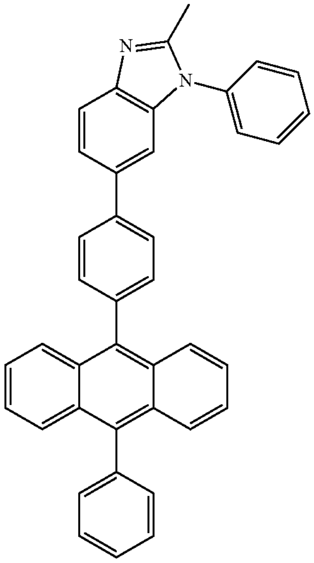
ET19
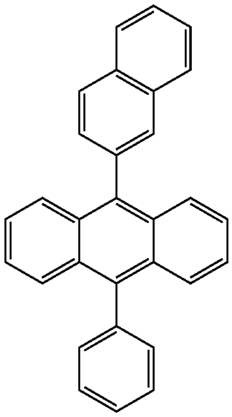

ET20
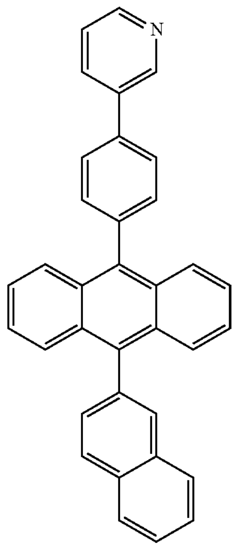
ET21
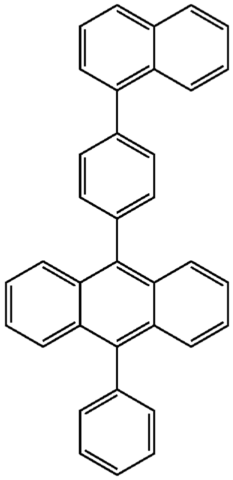
ET22
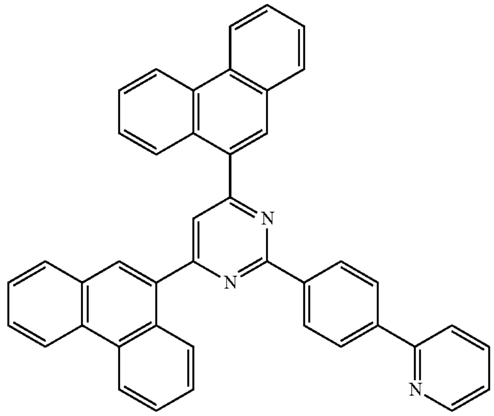
ET23
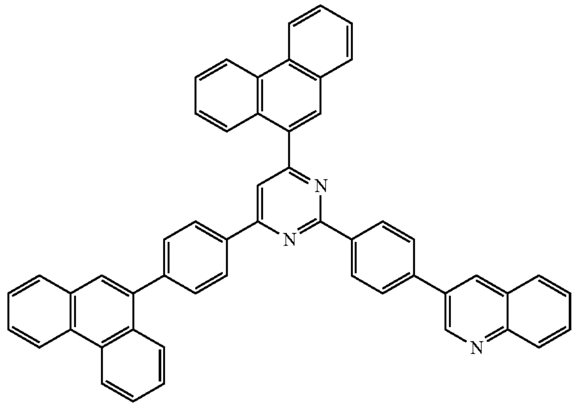
ET24
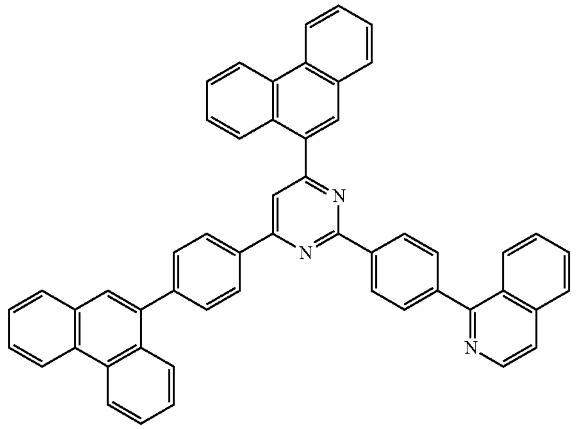
ET25
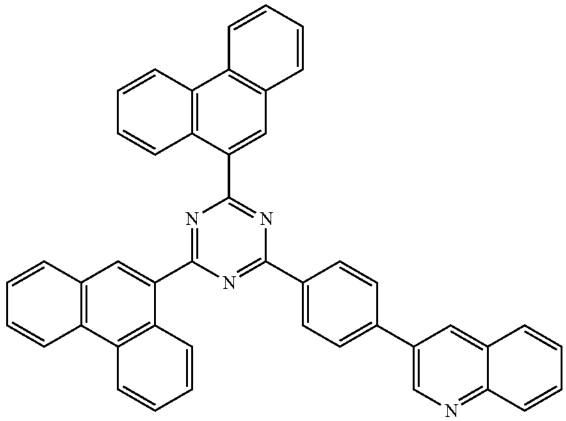

-continued
ET26
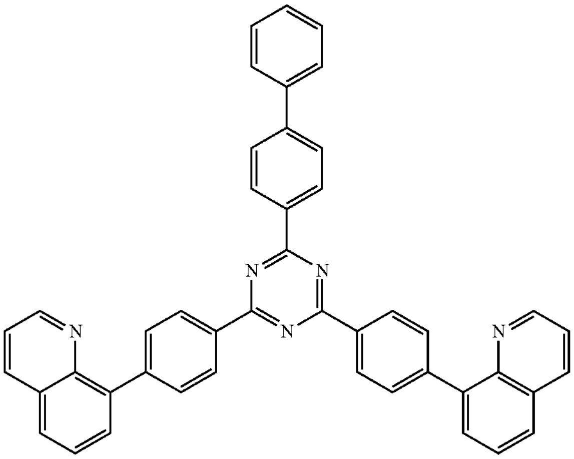
ET27
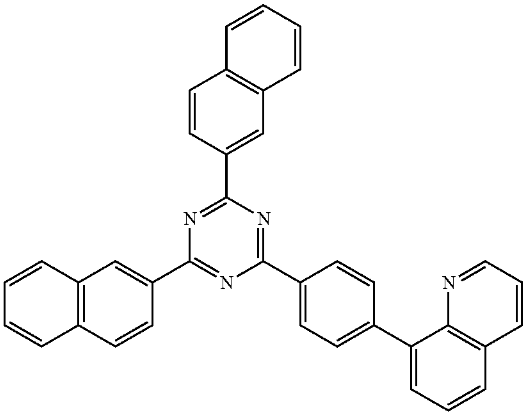
ET28
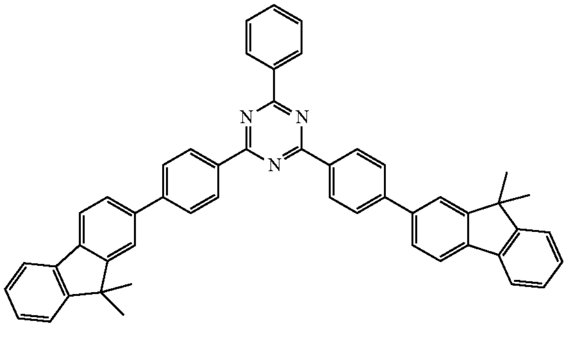
-continued
ET29
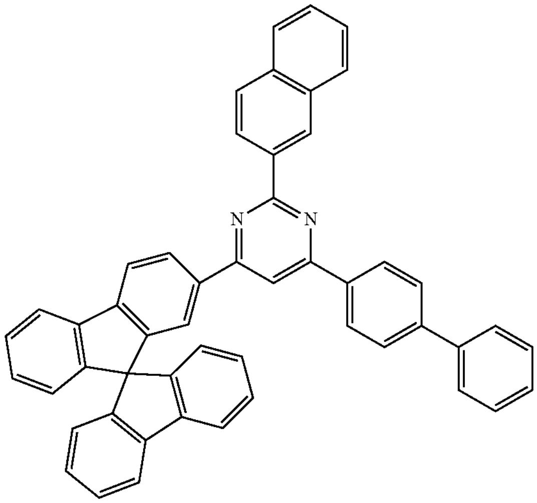
ET30
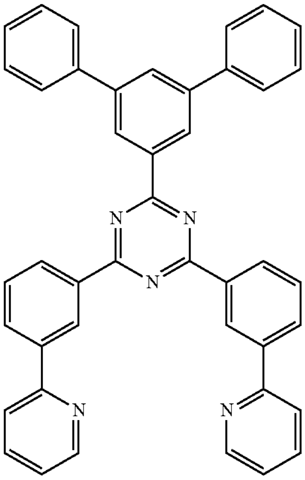
ET31
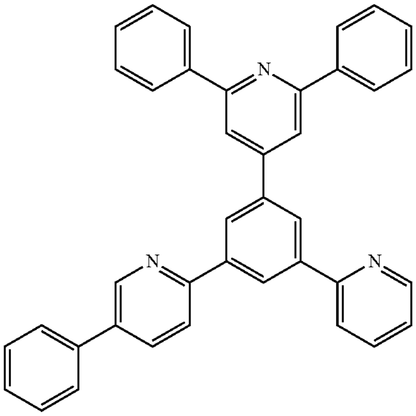

-continued

ET32

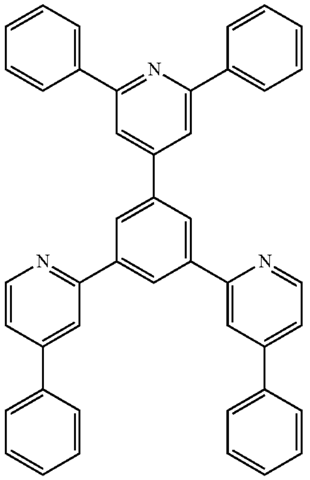

ET33

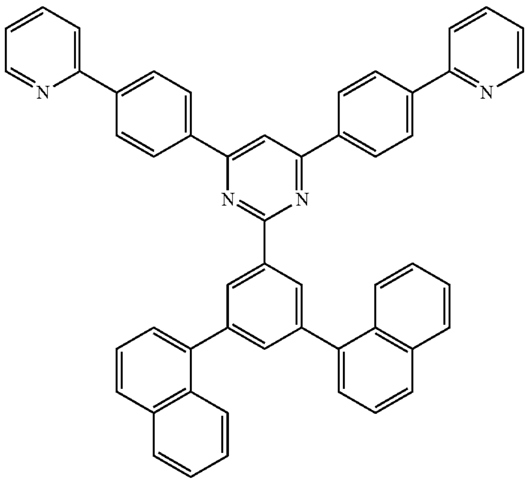

ET34

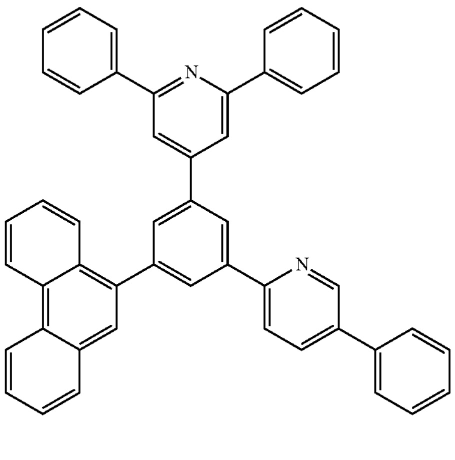

-continued

ET35

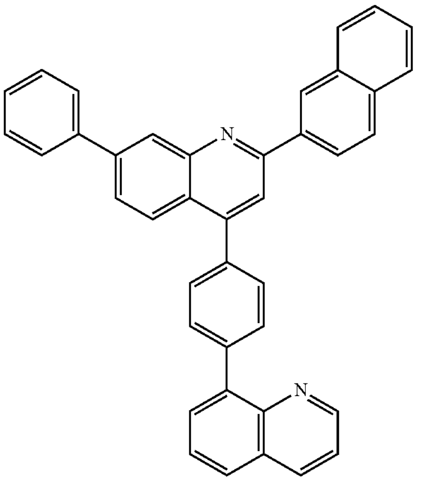

ET36

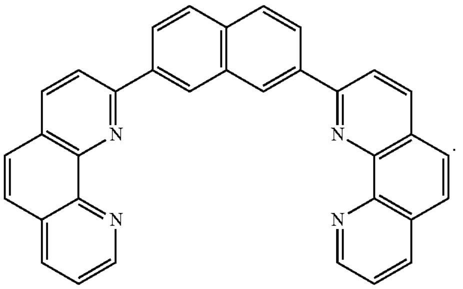

In some embodiments, the electron transport region may include at least one compound selected from 2,9-dimethyl-4,7-diphenyl-1,10-phenanthroline (BCP), 4,7-diphenyl-1,10-phenanthroline (Bphen), Alq3, BAlq, 3-(biphenyl-4-yl)-5-(4-tert-butylphenyl)-4-phenyl-4H-1,2,4-triazole (TAZ), NTAZ, diphenyl[4-(triphenylsilyl)phenyl]phosphine oxide *(TSPO1), and 2,2',2"-(1,3,5-benzinetriyl)-tris(1-phenyl-1-H-benzimidazole) (TPBi):

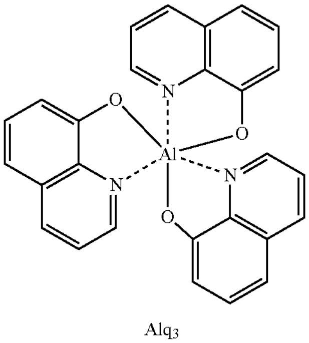

Alq3

-continued

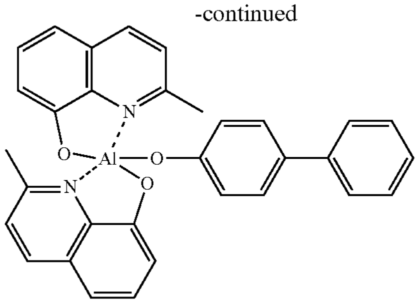

BAlq

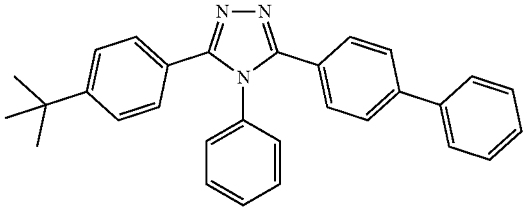

TAZ

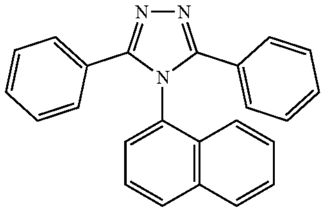

NTAZ

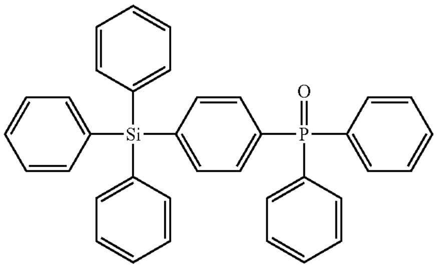

TSPO1

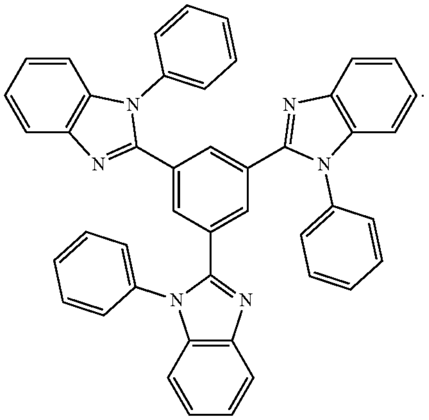

TPBi

The thicknesses of the buffer layer, the hole blocking layer, or the electron control layer may each independently be in a range of about 20 Å to about 1,000 Å, and in some embodiments, about 30 Å to about 300 Å. When the thicknesses of the buffer layer, the hole blocking layer or the electron control layer are within any of the foregoing ranges, excellent hole blocking characteristics or excellent electron controlling characteristics may be obtained without a substantial increase in driving voltage.

The thickness of the electron transport layer may be in a range of about 100 Å to about 1,000 Å, and in some embodiments, about 150 Å to about 500 Å. When the thickness of the electron transport layer is within any of the foregoing ranges, excellent electron transport characteristics may be obtained without a substantial increase in driving voltage.

The electron transport region (for example, the electron transport layer in the electron transport region) may further include, in addition to the materials described above, a metal-containing material.

The metal-containing material may include at least one selected from an alkali metal complex and an alkaline earth metal complex. The alkali metal complex may include a metal ion selected from a lithium (Li) ion, a sodium (Na) ion, a potassium (K) ion, a rubidium (Rb) ion, and a cesium (Cs) ion. The alkaline earth metal complex may include a metal ion selected from a beryllium (Be) ion, a magnesium (Mg) ion, a calcium (Ca) ion, a strontium (Sr) ion, and a barium (Ba) ion. Each ligand coordinated with the metal ion of the alkali metal complex and the alkaline earth metal complex may independently be selected from hydroxyquinoline, hydroxyisoquinoline, hydroxybenzoquinoline, hydroxyacridine, hydroxyphenanthridine, hydroxyphenyloxazole, hydroxyphenylthiazole, hydroxyphenyloxadiazole, hydroxyphenylthiadiazole, hydroxyphenylpyridine, hydroxyphenylbenzimidazole, hydroxyphenylbenzothiazole, bipyridine, phenanthroline, and cyclopentadiene, but embodiments are not limited thereto.

For example, the metal-containing material may include a Li complex. The Li complex may include, e.g., Compound ET-D1 (LiQ) or Compound ET-D2:

ET-D1

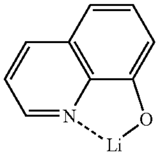

ET-D2

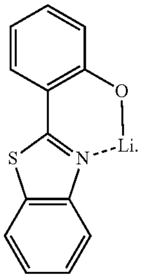

The electron transport region may include an electron injection layer that facilitates injection of electrons from the second electrode 190. The electron injection layer may be in direct contact with the second electrode 190.

The electron injection layer may have i) a single-layered structure including (e.g., consisting of) a single layer including (e.g., consisting of) a single material, ii) a single-layered structure including (e.g., consisting of) a single layer including a plurality of different materials, or iii) a multi-layered structure having a plurality of layers, each including a plurality of different materials.

The electron injection layer may include an alkali metal, an alkaline earth metal, a rare earth metal, an alkali metal compound, an alkaline earth metal compound, a rare earth metal compound, an alkali metal complex, an alkaline earth metal complex, a rare earth metal complex, or a combination thereof.

The alkali metal may be selected from $L_1$, Na, K, Rb, and Cs. In some embodiments, the alkali metal may be $L_1$, Na, or Cs. In one or more embodiments, the alkali metal may be Li or Cs, but embodiments are not limited thereto.

The alkaline earth metal may be selected from Mg, Ca, Sr, and Ba.

The rare earth metal may be selected from Sc, Y, Ce, Tb, Yb, and Gd.

The alkali metal compound, the alkaline earth metal compound, and the rare earth metal compound may each independently be selected from oxides and halides (e.g., fluorides, chlorides, bromides, or iodines) of the alkali metal, the alkaline earth metal, and the rare earth metal, respectively.

The alkali metal compound may be selected from alkali metal oxides, such as $Li_2O$, $Cs_2O$, and $K_2O$, and alkali metal halides, such as LiF, NaF, CsF, KF, LiI, NaI, CsI, and KI. In some embodiments, the alkali metal compound may be selected from LiF, $Li_2O$, NaF, LiI, NaI, CsI, and KI, but embodiments are not limited thereto.

The alkaline earth-metal compound may be selected from alkaline earth-metal compounds, such as BaO, SrO, CaO, $Ba_xSr_{1-x}O$ (wherein $0<x<1$), and $Ba_xCa_{1-x}O$ (wherein $0<x<1$). In some embodiments, the alkaline earth metal compound may be selected from BaO, SrO, and CaO, but embodiments are not limited thereto.

The rare earth metal compound may be selected from $YbF_3$, $ScF_3$, $Sc_2O_3$, $Y_2O_3$, $Ce_2O_3$, $GdF_3$, and $TbF_3$. In some embodiments, the rare earth metal compound may be selected from $YbF_3$, $ScF_3$, $TbF_3$, $YbI_3$, $ScI_3$, and $TbI_3$, but embodiments are not limited thereto.

The alkali metal complex, the alkaline earth metal complex, and the rare earth metal complex may each include ions of the above-described alkali metal, alkaline earth metal, and rare earth metal. Each ligand coordinated with the metal ion of the alkali metal complex, the alkaline earth metal complex, and the rare earth metal complex may independently be selected from hydroxyquinoline, hydroxyisoquinoline, hydroxybenzoquinoline, hydroxyacridine, hydroxyphenanthridine, hydroxyphenyloxazole, hydroxyphenylthiazole, hydroxyphenyloxadiazole, hydroxyphenylthiadiazole, hydroxyphenylpyridine, hydroxyphenylbenzimidazole, hydroxyphenylbenzothiazole, bipyridine, phenanthroline, and cyclopentadiene, but embodiments are not limited thereto.

The electron injection layer may include (e.g., consist of) an alkali metal, an alkaline earth metal, a rare earth metal, an alkali metal compound, an alkaline earth metal compound, a rare earth metal compound, an alkali metal complex, an alkaline earth metal complex, a rare earth metal complex, or a combination thereof, as described above. In some embodiments, the electron injection layer may further include an organic material. When the electron injection layer further includes an organic material, the alkali metal, the alkaline earth metal, the rare earth metal, the alkali metal compound, the alkaline earth metal compound, the rare earth metal compound, the alkali metal complex, the alkaline earth metal complex, the rare earth metal complex, or a combination thereof may be homogeneously or non-homogeneously dispersed in a matrix including the organic material.

The thickness of the electron injection layer may be in a range of about 1 Å to about 100 Å, and in some embodiments, about 3 Å to about 90 Å. When the thickness of the electron injection layer is within any of the foregoing ranges, excellent electron injection characteristics may be obtained without a substantial increase in driving voltage.

Second Electrode 190

The second electrode 190 may be on the organic layer 150. In an embodiment, the second electrode 190 may be a cathode (e.g., an electron injection electrode). In this embodiment, a material for forming the second electrode 190 may be a material having a low work function such as, for example, a metal, an alloy, an electrically conductive compound, or a combination thereof.

The second electrode 190 may include at least one selected from lithium (Li), silver (Ag), magnesium (Mg), aluminum (Al), aluminum-lithium (Al—Li), calcium (Ca), magnesium-indium (Mg—In), magnesium-silver (Mg—Ag), silver-magnesium (Ag—Mg), ytterbium (Yb), silver-ytterbium (Ag—Yb), ITO, and IZO, but embodiments are not limited thereto. The second electrode 190 may be a transmissive electrode, a semi-transmissive electrode, or a reflective electrode.

The second electrode 190 may have a single-layered structure, or a multi-layered structure including two or more layers.

Figure 2:
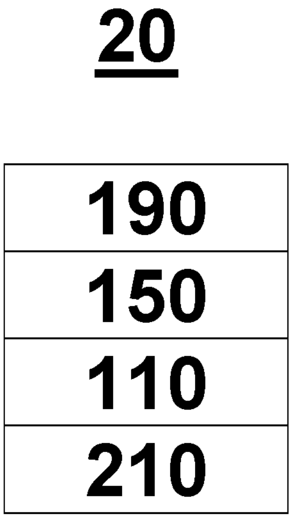
FIG. 2 is a schematic cross-sectional view of an embodiment of an organic light-emitting device.
Figure 3:
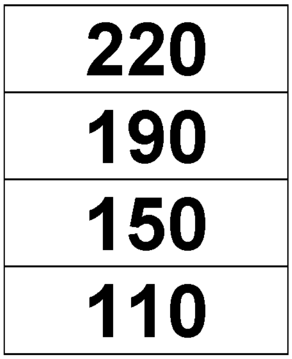
FIG. 3 is a schematic cross-sectional view of an embodiment of an organic light-emitting device.
Figure 4:
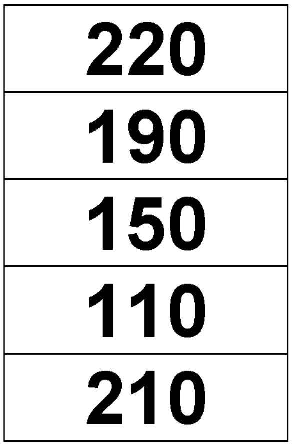
FIG. 4 is a schematic cross-sectional view of an embodiment of an organic light-emitting device.

Description of FIGS. 2 to 4

Referring to FIG. 2, an organic light-emitting device 20 has a first capping layer 210, the first electrode 110, the organic layer 150, and the second electrode 190 structure, wherein the layers are sequentially stacked in this stated order. Referring to FIG. 3, an organic light-emitting device 30 has the first electrode 110, the organic layer 150, the second electrode 190, and a second capping layer 220 structure, wherein the layers are sequentially stacked in this stated order. Referring to FIG. 4, an organic light-emitting device 40 has the first capping layer 210, the first electrode 110, the organic layer 150, the second electrode 190, and the second capping layer 220 structure, wherein the layers are stacked in this stated order.

The first electrode 110, the organic layer 150, and the second electrode 190 illustrated in FIGS. 2 to 4 may be substantially the same as those illustrated in FIG. 1.

In the organic light-emitting devices 20 and 40, light emitted from the emission layer in the organic layer 150 may pass through the first electrode 110 (which may be a semi-transmissive electrode or a transmissive electrode) and through the first capping layer 210 to the outside. In the organic light-emitting devices 30 and 40, light emitted from the emission layer in the organic layer 150 may pass through the second electrode 190 (which may be a semi-transmissive electrode or a transmissive electrode) and through the second capping layer 220 to the outside.

The first capping layer 210 and the second capping layer 220 may improve the external luminescence efficiency based on the principle of constructive interference.

The first capping layer 210 and the second capping layer 220 may each independently include an organic matter, an inorganic matter, or any combination thereof.

At least one of the first capping layer 210 and the second capping layer 220 may each independently include at least one selected from a carbocyclic compound, a heterocyclic compound, an amine group-containing compound, a porphine derivative, a phthalocyanine derivative, a naphthalocyanine derivative, an alkali metal complex, an alkaline earth metal complex, a silicon-based inorganic matter such as SiON, SiNx, or SiOx, a silicon-based organic matter, an acrylic compound, and an epoxy compound. The carbocyclic compound, the heterocyclic compound, and the amine group-containing compound may optionally be substituted with a substituent containing at least one element selected from O, N, S, Se, Si, F, Cl, Br, and I. In some embodiments, at least one of the first capping layer 210 and the second capping layer 220 may each independently include an amine-based compound.

In one or more embodiments, at least one of the first capping layer 210 and the second capping layer 220 may each independently include a compound represented by Formula 201 or a compound represented by 202.

In one or more embodiments, at least one of the first capping layer 210 and the second capping layer 220 may each independently include a compound selected from Compounds HT28 to HT33 and Compound CP1 to CP5, but embodiments are not limited thereto:

CP1

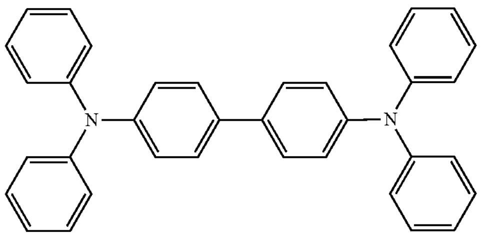

CP2

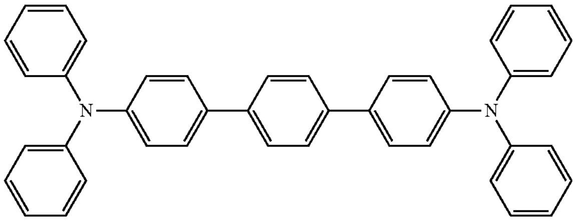

CP3

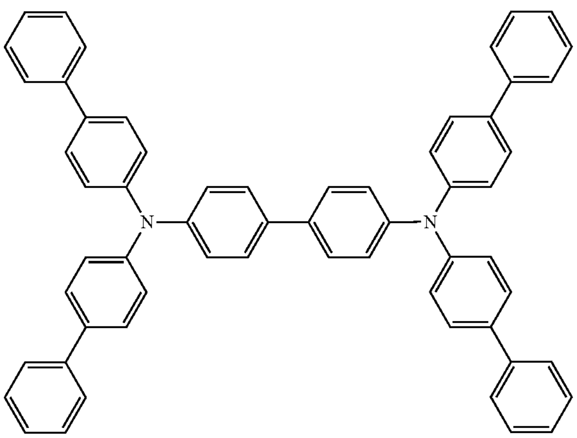

-continued

CP4

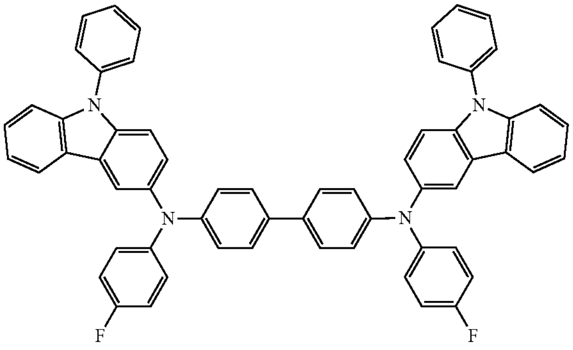

CP5

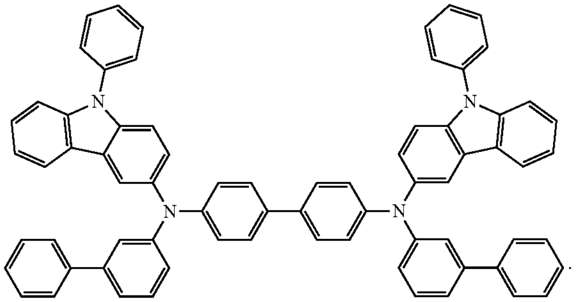

Hereinbefore, the organic light-emitting device has been described with reference to FIGS. 1 to 4, but embodiments are not limited thereto.

The layers constituting the hole transport region, the emission layer, and the layers constituting the electron transport region may be formed in a set or specific region by using one or more suitable methods such as vacuum deposition, spin coating, casting, Langmuir-Blodgett (LB) deposition, ink-jet printing, laser printing, and laser-induced thermal imaging.

When the layers constituting the hole transport region, the emission layer, and the layers constituting the electron transport region are each formed by vacuum deposition, the vacuum deposition may be performed at a deposition temperature in a range of about 100° C. to about 500° C. at a vacuum degree in a range of about $10^{-8}$ torr to about $10^{-3}$ torr, and at a deposition rate in a range of about 0.01 Angstroms per second (Å/sec) to about 100 Å/sec, depending on the material to be included in each layer and the structure of each layer to be formed.

When the layers constituting the hole transport region, the emission layer, and the layers constituting the electron transport region are each formed by spin coating, the spin coating may be performed at a coating rate of about 2,000 revolutions per minute (rpm) to about 5,000 rpm and at a heat treatment temperature of about 80° C. to about 200° C., depending on the material to be included in each layer and the structure of each layer to be formed.

General Definitions of at Least Some of the Substituents

The term "$C_1$-$C_{60}$ alkyl group," as used herein, refers to a linear or branched aliphatic hydrocarbon monovalent group having 1 to 60 carbon atoms. Examples thereof include a methyl group, an ethyl group, a propyl group, an iso-butyl group, a sec-butyl group, a tert-butyl group, a pentyl group, an iso-amyl group, and a hexyl group. The term "$C_1$-$C_{60}$ alkylene group," as used herein, refers to a divalent group having substantially the same structure as the $C_1$-$C_{60}$ alkyl group.

The term "$C_2$-$C_{60}$ alkenyl group," as used herein, refers to a hydrocarbon group having at least one carbon-carbon double bond at a main chain (e.g., in the middle) or at a terminal end (e.g., the terminus) of the $C_2$-$C_{60}$ alkyl group. Examples thereof include an ethenyl group, a propenyl group, and a butenyl group. The term "$C_2$-$C_{60}$ alkenylene group," as used herein, refers to a divalent group having substantially the same structure as the $C_2$-$C_{60}$ alkenyl group.

The term "$C_2$-$C_{60}$ alkynyl group," as used herein, refers to a hydrocarbon group having at least one carbon-carbon triple bond in the middle or at the terminus of the $C_2$-$C_{60}$ alkyl group. Examples thereof include an ethynyl group and a propynyl group. The term "$C_2$-$C_{60}$ alkynylene group" as used herein refers to a divalent group having substantially the same structure as the $C_2$-$C_{60}$ alkynyl group.

The term "$C_1$-$C_{60}$ alkoxy group," as used herein, refers to a monovalent group represented by -$OA_{101}$ (wherein $A_{101}$ is a $C_1$-$C_1$ alkyl group). Examples thereof include a methoxy group, an ethoxy group, and an isopropyloxy group.

The term "$C_3$-$C_{10}$ cycloalkyl group," as used herein, refers to a monovalent saturated hydrocarbon monocyclic group including 3 to 10 carbon atoms. Examples thereof include a cyclopropyl group, a cyclobutyl group, a cyclopentyl group, a cyclohexyl group, and a cycloheptyl group. The term "$C_3$-$C_{10}$ cycloalkylene group," as used herein, refers to a divalent group having substantially the same structure as the $C_3$-$C_{10}$ cycloalkyl group.

The term "$C_1$-$C_{10}$ heterocycloalkyl group," as used herein, refers to a monovalent monocyclic group including at least one heteroatom selected from N, O, Si, P, and S as a ring-forming atom and 1 to 10 carbon atoms. Examples thereof include a 1,2,3,4-oxatriazolidinyl group, a tetrahydrofuranyl group, and a tetrahydrothiophenyl group. The term "$C_1$-$C_{10}$ heterocycloalkylene group," as used herein, refers to a divalent group having substantially the same structure as the $C_1$-$C_{10}$ heterocycloalkyl group.

The term "$C_3$-$C_{10}$ cycloalkenyl group," as used herein, refers to a monovalent monocyclic group that has 3 to 10 carbon atoms and at least one double bond in its ring, and is not aromatic. Examples thereof include a cyclopentenyl group, a cyclohexenyl group, and a cycloheptenyl group. The term "$C_3$-$C_{10}$ cycloalkenylene group," as used herein, refers to a divalent group having substantially the same structure as the $C_3$-$C_{10}$ cycloalkenyl group.

The term "$C_1$-$C_{10}$ heterocycloalkenyl group," as used herein, refers to a monovalent monocyclic group including at least one heteroatom selected from N, O, Si, P, and S as a ring-forming atom, 1 to 10 carbon atoms, and at least one double bond in its ring. Examples of the $C_1$-$C_{10}$ heterocycloalkenyl group include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkylene group," as used herein, refers to a divalent group having substantially the same structure as the $C_1$-$C_{10}$ heterocycloalkyl group.

The term "$C_6$-$C_{60}$ aryl group," as used herein, refers to a monovalent group having a carbocyclic aromatic system having 6 to 6 carbon atoms. The term "$C_6$-$C_{60}$ arylene group," as used herein, refers to a divalent group having a carbocyclic aromatic system having 6 to 60 carbon atoms. Examples of the $C_6$-$C_{60}$ aryl group include a fluorenyl group, a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each independently include two or more rings, the respective rings may be fused (e.g., combined together).

The term "$C_1$-$C_{60}$ heteroaryl group," as used herein, refers to a monovalent group having a heterocyclic aromatic system having at least one heteroatom selected from N, O, Si, P, and S as a ring-forming atom and 1 to 60 carbon atoms. The term "$C_1$-$C_{60}$ heteroarylene group," as used herein, refers to a divalent group having a heterocyclic aromatic system having at least one heteroatom selected from N, O, Si, P, and S as a ring-forming atom and 1 to 60 carbon atoms. Examples of the $C_1$-$C_{60}$ heteroaryl group include a carbazolyl group, a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each independently include two or more rings, the respective rings may be fused (e.g., combined together).

The term "$C_6$-$C_{60}$ aryloxy group," as used herein, is represented by -$OA_{102}$ (wherein $A_{102}$ is the $C_6$-$C_{60}$ aryl group). The term "$C_6$-$C_{60}$ arylthio group," as used herein, is represented by -$SA_{103}$ (wherein $A_{103}$ is the $C_6$-$C_{60}$ aryl group).

The term "monovalent non-aromatic condensed polycyclic group," as used herein, refers to a monovalent group that has two or more rings condensed (e.g., combined together with each other) and only carbon atoms as ring forming atoms (e.g., 8 to 60 carbon atoms), wherein the entire molecular structure is non-aromatic. Examples of the monovalent non-aromatic condensed polycyclic group may include a fluorenyl group. The term "divalent non-aromatic condensed polycyclic group," as used herein, refers to a divalent group having substantially the same structure as the monovalent non-aromatic condensed polycyclic group.

The term "monovalent non-aromatic condensed heteropolycyclic group," as used herein, refers to a monovalent group that has two or more condensed rings and at least one heteroatom selected from N, O, Si, P, and S, in addition to carbon atoms (e.g., 1 to 60 carbon atoms), as a ring-forming atom, wherein the entire molecular structure is non-aromatic. Examples of the monovalent non-aromatic condensed heteropolycyclic group may include a carbazolyl group. The term "divalent non-aromatic condensed heteropolycyclic group," as used herein, refers to a divalent group having substantially the same structure as the monovalent non-aromatic condensed heteropolycyclic group.

The term "$C_5$-$C_{60}$ carbocyclic group," as used herein, refers to a monocyclic or polycyclic group having 5 to 60 carbon atoms only as ring-forming atoms. The $C_5$-$C_{60}$ carbocyclic group may be an aromatic carbocyclic group or a non-aromatic carbocyclic group. The term "$C_5$-$C_{60}$ carbocyclic group," as used herein, refers to a ring (e.g., a benzene group), a monovalent group (e.g., a phenyl group), or a divalent group (e.g., a phenylene group). Also, depending on the number of substituents connected to the $C_5$-$C_{60}$ carbocyclic group, the $C_5$-$C_{60}$ carbocyclic group may be a trivalent group or a quadrivalent group.

The term "$C_1$-$C_{60}$ heterocyclic group," as used herein, refers to a group having substantially the same structure as the $C_5$-$C_{60}$ carbocyclic group, except that at least one heteroatom selected from N, O, Si, P, and S is used as a ring-forming atom, in addition to carbon atoms (e.g., 1 to 60 carbon atoms).

In the present specification, at least one of substituents of the substituted $C_5$-$C_{60}$ carbocyclic group, the substituted $C_1$-$C_{60}$ heterocyclic group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium (-D), —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(═O)($Q_{11}$), —S(═O)$_2$($Q_{11}$), and —P(═O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(═O)($Q_{21}$), —S(═O)$_2$($Q_{21}$), and —P(═O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(═O)($Q_{31}$), —S(═O)$_2$($Q_{31}$), and —P(═O)($Q_{31}$)($Q_{32}$), wherein $Q_{11}$ to $Q_{13}$, $Q_{21}$ to $Q_{23}$, and $Q_{31}$ to $Q_{33}$ may each independently be selected from hydrogen; deuterium; —F; —Cl; —Br; —I; a hydroxyl group; a cyano group; a nitro group; an amidino group; a hydrazino group; a hydrazono group; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{10}$ cycloalkyl group; a $C_1$-$C_{10}$ heterocycloalkyl group; a $C_3$-$C_{10}$ cycloalkenyl group; a $C_1$-$C_{10}$ heterocycloalkenyl group; a $C_6$-$C_{60}$ aryl group; a $C_1$-$C_{60}$ heteroaryl group; a monovalent non-aromatic condensed polycyclic group; a monovalent non-aromatic condensed heteropolycyclic group; a $C_1$-$C_{60}$ alkyl group substituted with at least one selected from deuterium, —F, and a cyano group; a $C_6$-$C_{60}$ aryl group substituted with at least one selected from deuterium, —F, and a cyano group; a biphenyl group; and a terphenyl group.

The term "Ph," as used herein, represents a phenyl group, the term "Me," as used herein, represents a methyl group, the term "Et," as used herein, represents an ethyl group, the term "ter-Bu" or "Bu$^t$," as used herein, represents a tert-butyl group, and the term "OMe," as used herein, represents a methoxy group.

The term "biphenyl group," as used herein, refers to a phenyl group substituted with at least one phenyl group. The "biphenyl group" belongs to "a substituted phenyl group" having a "$C_6$-$C_{60}$ aryl group" as a substituent.

The term "terphenyl group," as used herein, refers to a phenyl group substituted with at least one phenyl group. The "terphenyl group" belongs to "a substituted phenyl group" having a "$C_6$-$C_{60}$ aryl group substituted with a $C_6$-$C_{60}$ aryl group" as a substituent.

The symbols * and *', as used herein, unless defined otherwise, refer to a binding site to an adjacent atom in a corresponding formula.

Hereinafter, compounds and an organic light-emitting device according to one or more embodiments will be described in more detail with reference to Synthesis Examples and Examples. The wording "B was used instead of A" used in describing Synthesis Examples means that an amount of B used was identical to an amount of A used in terms of molar equivalents.

EXAMPLES

Synthesis Example 1: Synthesis of Compound 1

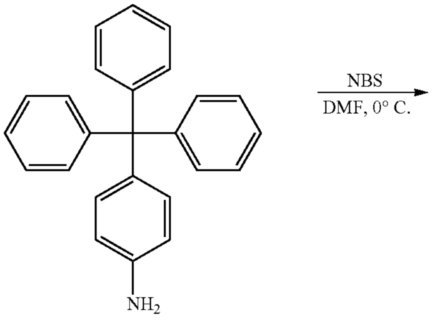

-continued

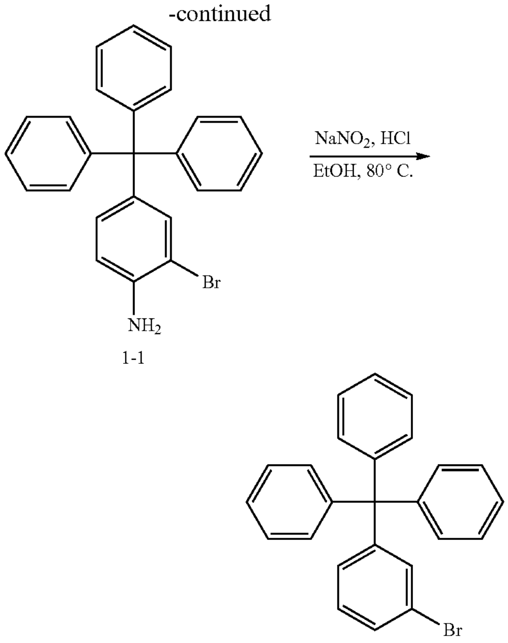

1-1

1-2

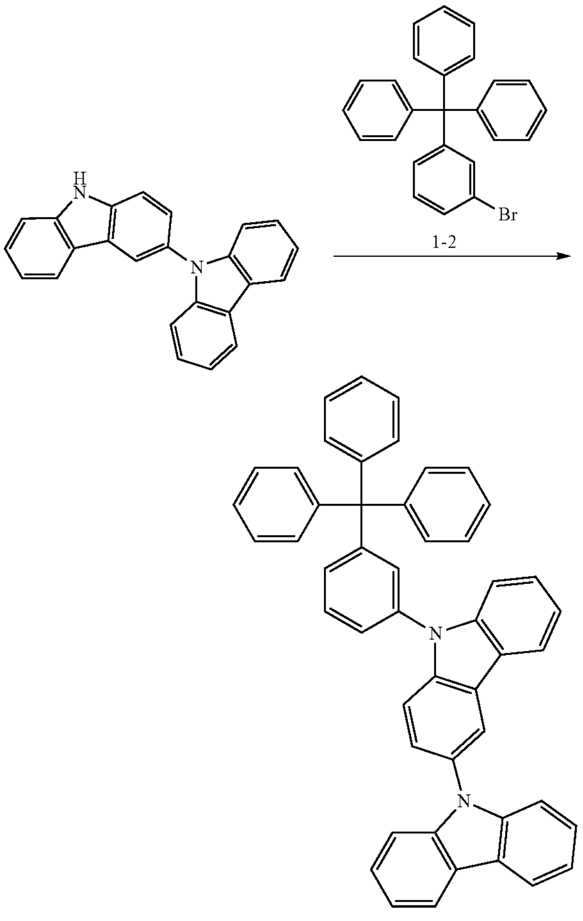

1-2

1

Synthesis of Intermediate 1-1

10 grams (g) of 4-tritylaniline was dissolved in 150 mL of a dimethyl formamide (DMF) solvent, and 5.3 g of N-bromosuccinimide(NBS) was slowly added thereto at a temperature of 0° C. Then, a reaction occurred at room temperature, followed by purification, thereby obtaining 11.7 g of Intermediate 1-1 (yield: 95%).

Synthesis of Intermediate 1-2

11.7 g of Intermediate 1-1 was dissolved in 200 mL of an ethanol solvent, and excess HCl (3 eq. or greater) was slowly added thereto at room temperature and stirred. After stirring, 3.9 g of sodium nitrite ($NaNO_2$) was added thereto, and a reaction occurred at a temperature of 80° C., followed by purification, thereby obtaining 7.89 g of Intermediate 1-2 (yield: 70%).

Synthesis of Compound 1

2 g of 3,9'-bicarbazole, 2.4 g of Intermediate 1-2, 0.87 g of sodium tert-butoxide, 0.22 g of tris(dibenzylideneacetone)dipalladium (0), and 0.13 milliliters (mL) of tri-tert-butylphosphine ($P(t\text{-}Bu)_3$) were dissolved in 30 mL of a toluene solvent and stirred for 12 hours. After stirring, an organic layer resulting from extraction of the reaction solution was dried. Subsequently, separation and purification using column chromatography was performed, and sublimation purification was followed, thereby obtaining 3.45 g of Compound 1 (yield: 88%).

Synthesis Example 2: Synthesis of Compound 5

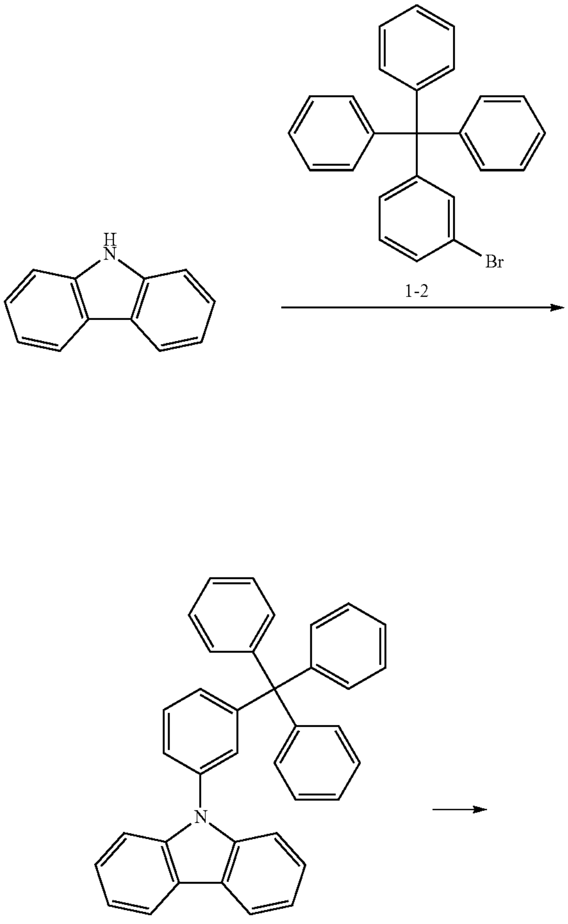

1-2

5-1

-continued

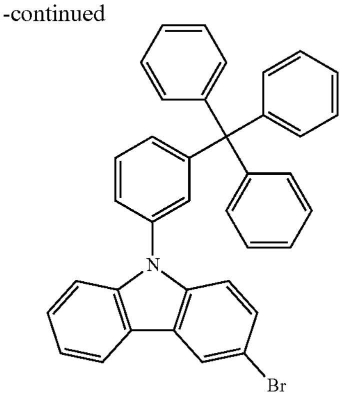

5-2

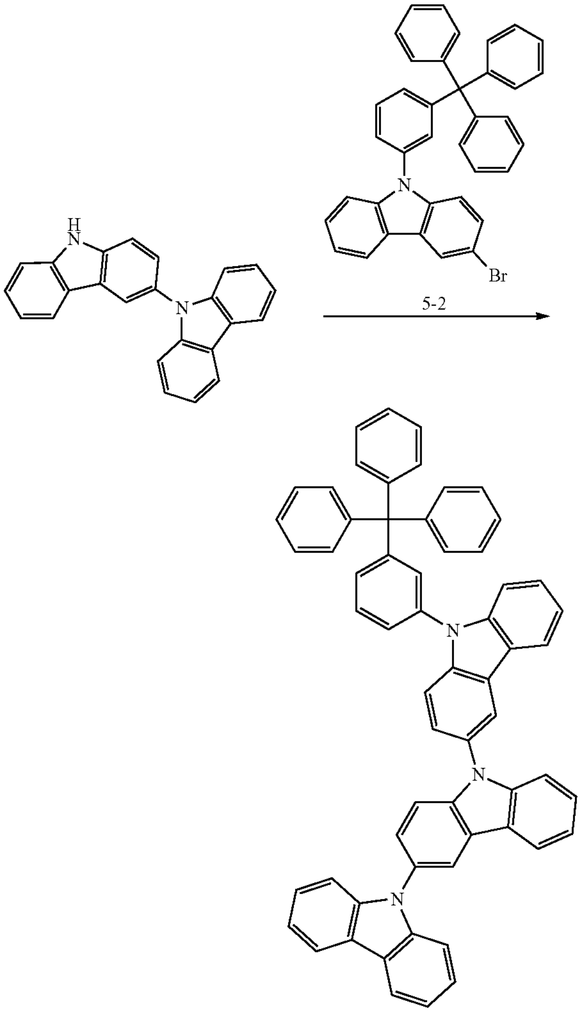

5

Synthesis of Intermediate 5-1

5 g of carbazole, 11.94 g of Intermediate 1-2, 4.3 g of sodium tert-butoxide, 1.09 g of tris(dibenzylidene acetone) dipalladium (0), and 0.5 mL of tris-t-butylphosphine were dissolved in 150 mL of a toluene solvent, followed by stirring for 12 hours. Once the reaction was believed to be complete, an organic layer resulting from extraction of the reaction solution was dried. Subsequently, the residue was separated and purified through column chromatography, thereby obtaining 10.89 g of Intermediate 5-1 (yield: 75%).

Synthesis of Intermediate 5-2

10.89 g of Intermediate 5-1 was dissolved in 120 mL of a DMF solvent, and 3.99 g of NBS was slowly added thereto at a temperature of 0° C. Then, a reaction occurred at room temperature, followed by purification, thereby obtaining 12.02 g of Intermediate 5-2 (yield: 95%).

Synthesis of Compound 5

2 g of 3,9'-bicarbazole, 3.4 g of Intermediate 5-2, 0.87 g of sodium tert-butoxide, 0.22 g of tris(dibenzylideneacetone)dipalladium (0), and 0.13 mL of tris-t-butylphosphine were dissolved in 30 mL of a toluene solvent and stirred for 12 hours. Once the reaction was believed to be complete, an organic layer resulting from extraction of the reaction solution was dried. Subsequently, separation and purification using column chromatography was performed, and sublimation purification was followed, thereby obtaining 4.07 g of Compound 5 (yield: 83%).

Synthesis Example 3: Synthesis of Compound 9

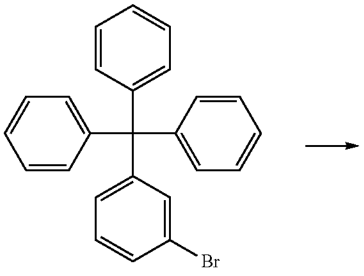

1-2

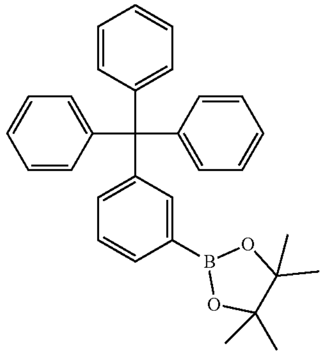

9-1

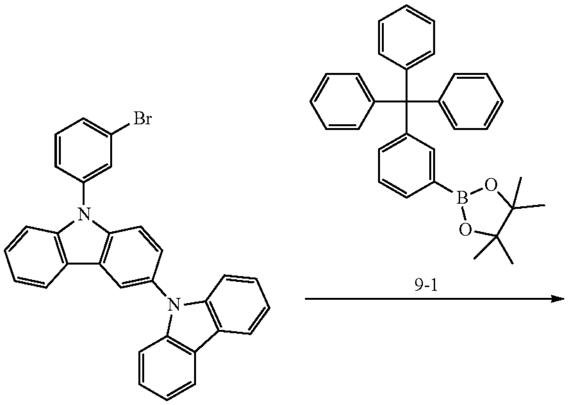

-continued

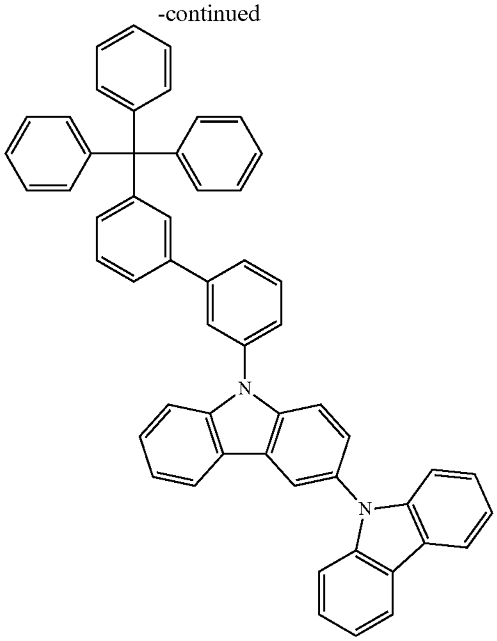

9

Synthesis of Intermediate 9-1

7.89 g of Intermediate 1-2, 3.8 g of potassium acetate, and 0.69 g of bis(triphenylphosphine)palladium(II) dichloride were added to 100 mL of a toluene solvent and stirred. Then, the mixture was reacted with 10 g of bis(pinacolato)diboron at a temperature of 10° C., thereby obtaining 5.28 g of Intermediate 9-1 (yield: 60%).

Synthesis of Compound 9

2 g of 9-(3-bromophenyl)-3,9'-bi-9H-carbazole, 1.83 g of Intermediate 9-1, and 0.24 g of tetrakis(triphenylphosphine) palladium (0) were added to 5 mL of a 2 molar (M) potassium carbonate aqueous solution and 20 mL of tetrahydrofuran (THF), followed by stirring at a temperature of 90° C. for 12 hours. Once the reaction was believed to be complete, an organic layer resulting from extraction of the reaction solution was dried. Subsequently, separation and purification using column chromatography was performed, and sublimation purification was followed, thereby obtaining 2.77 g of Compound 9 (yield: 93%).

Synthesis Example 4: Synthesis of Compound 13

-continued

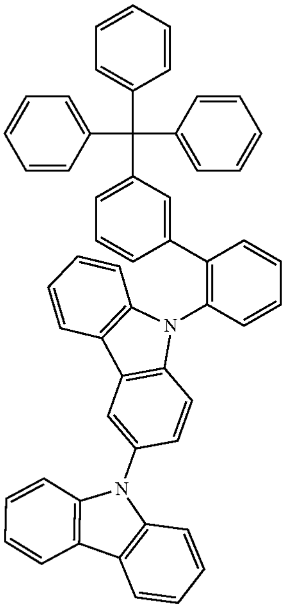

13

Synthesis of Compound 13

2 g of 9-(2-bromophenyl)-3,9'-bi-9H-carbazole, 1.83 g of Intermediate 9-1, and 0.24 g of tetrakis(triphenylphosphine) palladium (0) were added to 5 mL of a 2 M potassium carbonate aqueous solution and 20 mL of THF, followed by stirring at a temperature of 90° C. for 12 hours. Once the reaction was believed to be complete, an organic layer resulting from extraction of the reaction solution was dried. Subsequently, separation and purification using column chromatography was performed, and sublimation purification was followed, thereby obtaining 2.83 g of Compound 13 (yield: 95%).

Synthesis Example 5: Synthesis of Compound 17

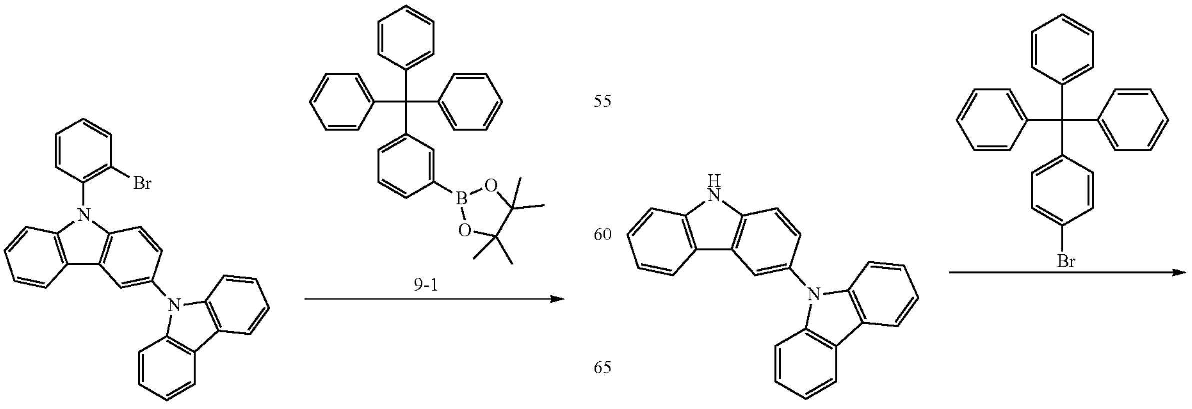

-continued

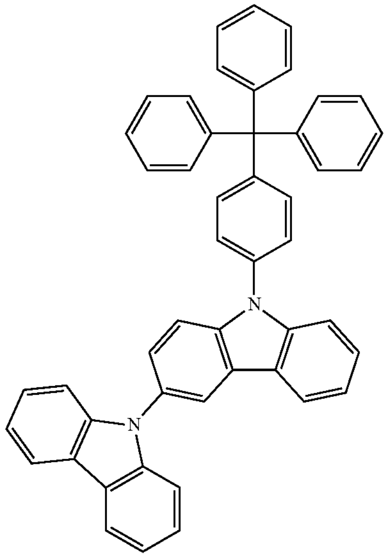

17

Synthesis of Compound 17

2 g of 3,9'-bicarbazole, 3.4 g of Intermediate 5-2, 0.87 g of sodium tert-butoxide, 0.22 g of tris(dibenzylideneacetone)dipalladium (0), and 0.13 mL of tri-tert-butylphosphine ($P(t\text{-}Bu)_3$) were dissolved in 30 mL of a toluene solvent and stirred for 12 hours. Once the reaction was believed to be complete, an organic layer resulting from extraction of the reaction solution was dried. Subsequently, separation and purification using column chromatography was performed, and sublimation purification was followed, thereby obtaining 3.8 g of Compound 17 (yield: 97%).

Synthesis Example 6: Synthesis of Compound 21

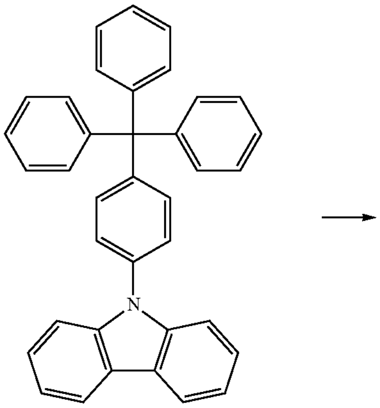

-continued

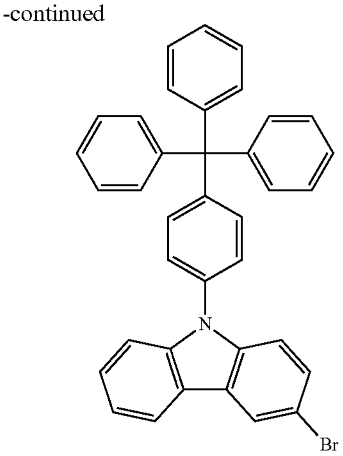

21-1

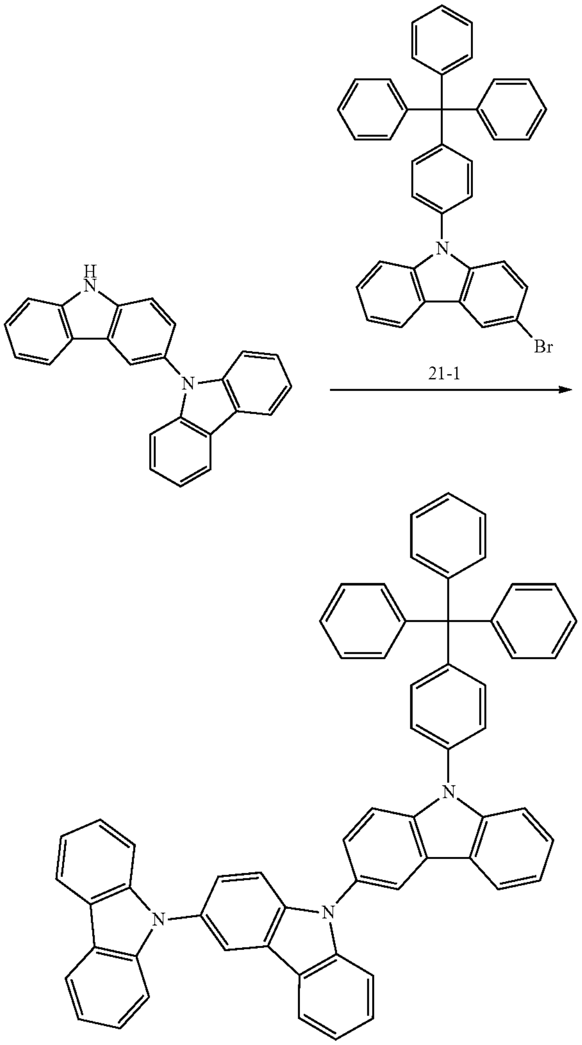

21-1

21

Synthesis of Intermediate 21-1

10 g of 9-(4-tritylphenyl)-9H-carbazole) was dissolved in 120 mL of a DMF solvent, and 3.52 g of NBS was slowly added thereto at a temperature of 0° C. Then, a reaction occurred at room temperature, followed by purification, thereby obtaining 11.39 g of Intermediate 21-1 (yield: 98%).

Synthesis of Compound 21

2 g of 3,9'-bicarbazole, 3.4 g of Intermediate 21-1, 0.87 g of sodium tert-butoxide, 0.22 g of tris(dibenzylideneacetone)dipalladium (0), and 0.13 mL of tris-t-butylphosphine were dissolved in 30 mL of a toluene solvent and stirred for 12 hours. Once the reaction was believed to be complete, an organic layer resulting from extraction of the reaction solution was dried. Subsequently, separation and purification using column chromatography was performed, and sublimation purification was followed, thereby obtaining 3.8 g of Compound 21 (yield: 97%).

The $^1$H NMR and MS/FAB results of the synthesized compounds are shown in Table 1. Methods of synthesizing compounds other than compounds shown in Table 1 may be easily understood to those skilled in the art by referring to the synthesis schemes and raw materials described above.

TABLE 1

| Compound | H NMR (δ) | Calc. | Found. |
|---|---|---|---|
| 1 | 8.55(d, 2H), 8.19(d, 1H), 7.94(d, 2H), 7.67(s, 1H), 7.58(d, 1H), 7.00-7.48(m, 26H) | 650.27 | 621.27 |
| 5 | 8.55(d, 3H), 8.19(d, 1H), 7.94(d, 3H), 7.78(s, 1H), 7.72(d, 2H), 7.67(s, 2H), 7.58(d, 1H), 7.10-7.50(m, 28H) | 815.33 | 816.02 |
| 9 | 8.55(d, 2H), 8.21-8.19(d, 2H), 7.94(d, 2H), 7.72-7.80(d, 2H), 7.58-7.60(d, 2H), 7.47-7.53(m, 3H), 7.38-7.41(m, 4H), 7.10-7.26(m, 21H) | 726.30 | 727.30 |
| 13 | 8.55(d, 2H), 8.19(d, 1H), 7.91-7.94(d, 5H), 7.67-7.80(m, 5H), 7.35-7.58(m, 5H), 7.10-7.26(m, 20H) | 726.30 | 726.92 |
| 17 | 8.55(d, 2H), 8.19(d, 1H), 7.94(d, 2H), 7.72(d, 1H), 7.67(s, 1H), 7.58(d, 1H), 7.50(t,1H), 7.35-7.38(m, 3H), 7.10-7.32 (m, 22H) | 650.27 | 651.27 |
| 21 | 8.55(d, 3H), 8.19(d, 1H), 7.94(d, 3H), 7.72(d, 2H), 7.67(s, 2H), 7.50-7.58(m, 2H), 7.32-7.38(m, 7H), 7.10-7.32(m, 21H) | 815.33 | 816.02 |

Example 1

A Corning 15 Ohms per square centimeter (Ω/cm$^2$) (1,200 Å) ITO glass substrate was cut to a size of 50 millimeters (mm)×50 mm×0.7 mm, sonicated in isopropyl alcohol and pure water for 5 minutes in each solvent, and cleaned by exposure to ultraviolet rays with ozone to use the glass substrate as an anode. Then, the glass substrate was mounted to a vacuum-deposition apparatus.

N,N'-di(1-naphthyl)-N,N'-diphenylbenzidine (NPD) was vacuum-deposited on the ITO anode formed on the glass substrate to form a hole injection layer having a thickness of 300 Å. TCTA was then vacuum-deposited on the hole injection layer to form a hole transport layer having a thickness of 200 Å.

Compound CzSi was vacuum-deposited on the hole transport layer to form an emission auxiliary layer having a thickness of 100 Å.

Compound 1 (host) and Ir(pnp) (dopant) were co-deposited to a weight ratio of 92:8 on the emission auxiliary layer to form an emission layer having a thickness of 250 Å.

TSPO1 was deposited on the emission layer to form a buffer layer having a thickness of 200 Å, and TPBI was deposited on the buffer layer to form an electron transport layer having a thickness of 300 Å.

LiF was deposited on the electron transport layer to form an electron injection layer having a thickness of 10 Å, and Al was vacuum-deposited on the electron injection layer to form an electrode having a thickness of 3,000 Å, thereby completing the manufacture of an organic light-emitting device.

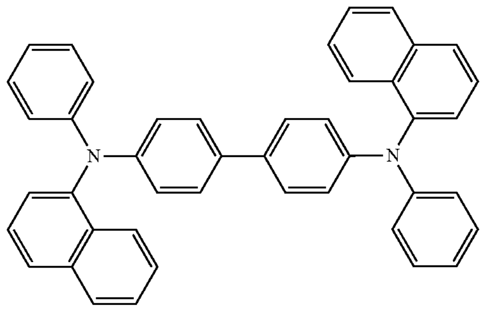

NPD

-continued

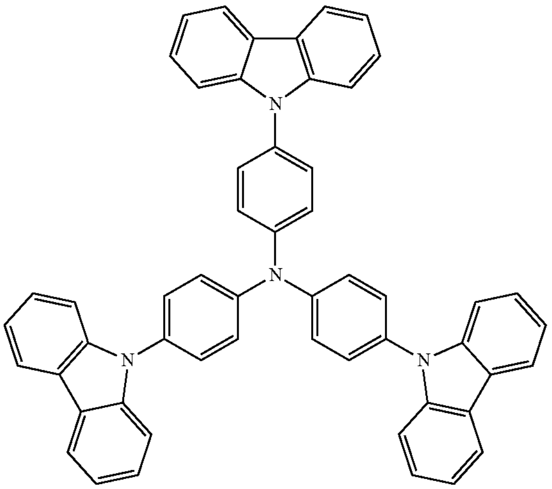

TCTA

-continued

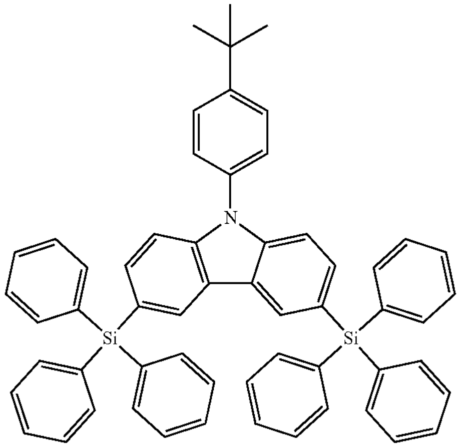

CzSi

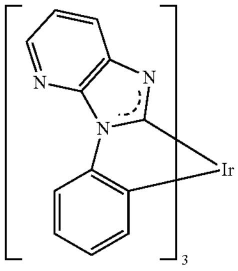

Ir(pmp)3

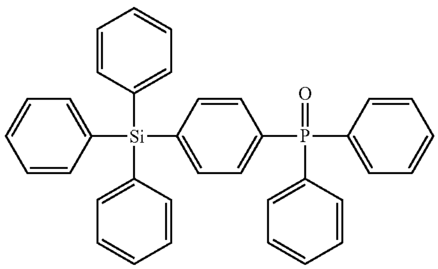

TSPO1

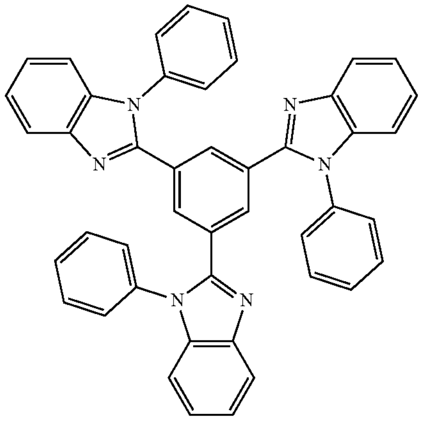

TPBI

Examples 2 to 6 and Comparative Examples 1 to 8

Organic light-emitting devices were manufactured in substantially the same manner as in Example 1, except that compounds shown in Table 2 were used instead of Compound 1.

Evaluation Example 1

To evaluate characteristics of the organic light-emitting devices manufactured in Examples 1 to 6 and Comparative Examples 1 to 8, the driving voltage, luminescence efficiency, and maximum external quantum efficiency (EQE) of the organic light-emitting devices at a current density of 10 milliamperes per square centimeter ($mA/cm^2$) were measured. The driving voltage of the organic light-emitting devices were measured using a source meter (Keithley Instrument, 2400 series). The maximum external quantum yield of the organic light-emitting devices were measured using a Hamamastu Absolute PL Quantum Yield Measurement System C9920-2-12. In evaluation of the maximum external quantum yield, luminance/current density was measured using a luminance meter with calibration of wavelength sensitivity, and the maximum external quantum yield was calculated on the assumption of the angular luminance distribution (Lambertian) assuming a complete diffusion reflecting surface. The evaluation results of the organic light-emitting devices are shown in Table 2.

TABLE 2

| | Host in emission layer | Driving voltage (V) | Luminescence efficiency (Cd/A) | Maximum external quantum efficiency (%) | Emission color |
|---|---|---|---|---|---|
| Example 1 | 1 | 4.5 | 21.6 | 22.0 | Blue |
| Example 2 | 5 | 4.3 | 22.4 | 21.5 | Blue |
| Example 3 | 9 | 4.9 | 20.5 | 20.7 | Blue |
| Example 4 | 13 | 4.8 | 19.3 | 20.1 | Blue |
| Example 5 | 17 | 4.4 | 22.0 | 21.2 | Blue |
| Example 6 | 21 | 4.3 | 20.1 | 19.8 | Blue |
| Comparative Example 1 | mCP | 5.3 | 10.2 | 11.2 | Blue |
| Comparative Example 2 | Compound A | 4.9 | 15.5 | 16.8 | Blue |
| Comparative Example 3 | Compound B | 5.2 | 10.7 | 12.5 | Blue |
| Comparative Example 4 | Compound C | 5.1 | 13.1 | 17.1 | Blue |
| Comparative Example 5 | Compound D | 5.8 | 12.2 | 10.7 | Blue |
| Comparative Example 6 | Compound E | 5.3 | 17.6 | 16.7 | Blue |
| Comparative Example 7 | Compound F | 6.2 | 11.4 | 8.9 | Blue |
| Comparative Example 8 | Compound G | 4.9 | 18.1 | 17.8 | Blue |

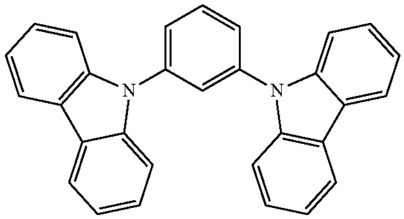
mCP
A
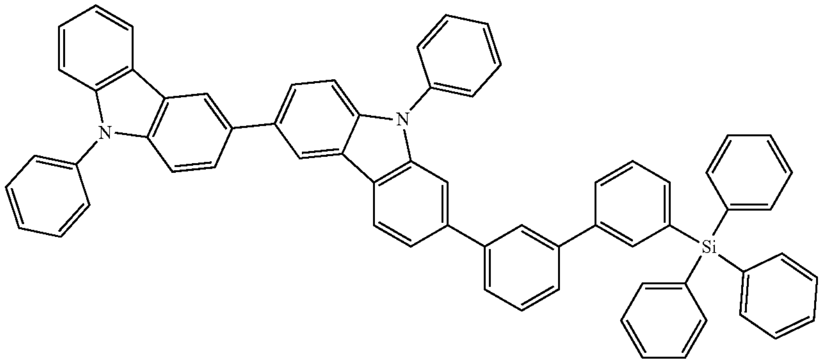
B
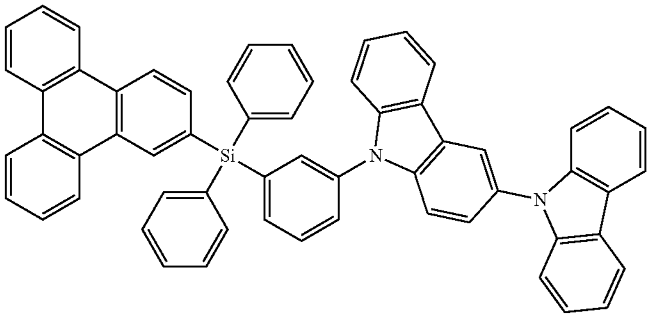
C
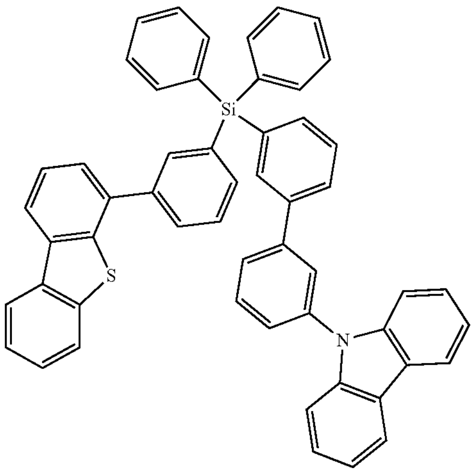

-continued
D
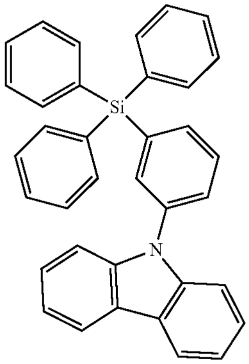
E
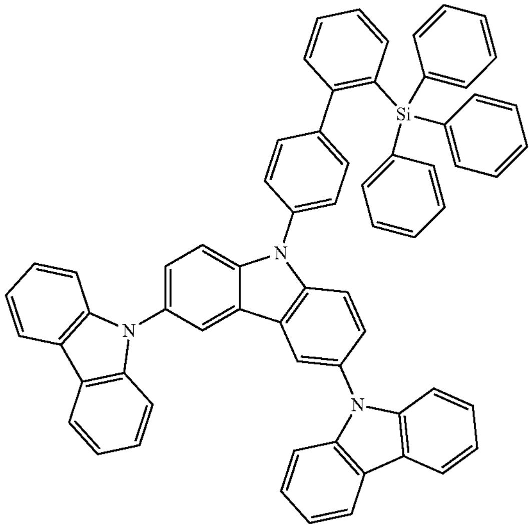
F
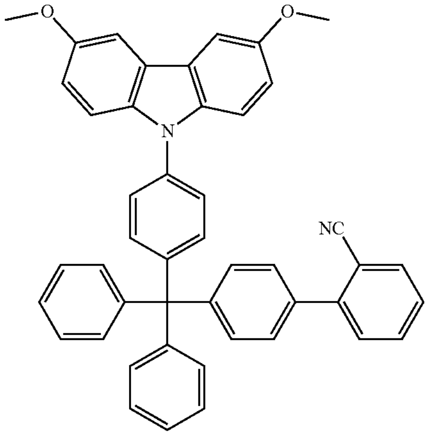
G
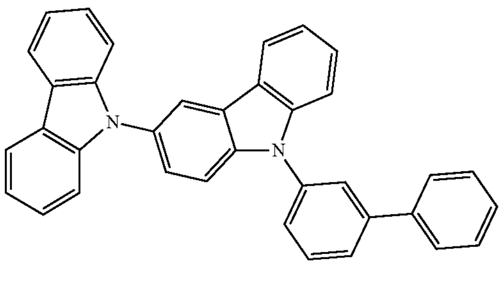

Referring to the results of Table 1, the organic light-emitting devices of Examples 1 to 6 were found to have excellent driving voltage, luminescence efficiency, and external quantum efficiency, as compared with the organic light-emitting devices of Comparative Examples 1 to 8.

As apparent from the foregoing description, the organic light-emitting device including the heterocyclic compound may have excellent driving voltage, luminescence efficiency, and external quantum efficiency.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the present disclosure as defined by the following claims, and equivalents thereof.

What is claimed is:

1. An organic light-emitting device comprising:

a first electrode;

a second electrode facing the first electrode;

an organic layer between the first electrode and the second electrode and comprising an emission layer; and at least one heterocyclic compound represented by Formula 1:

Formula 1

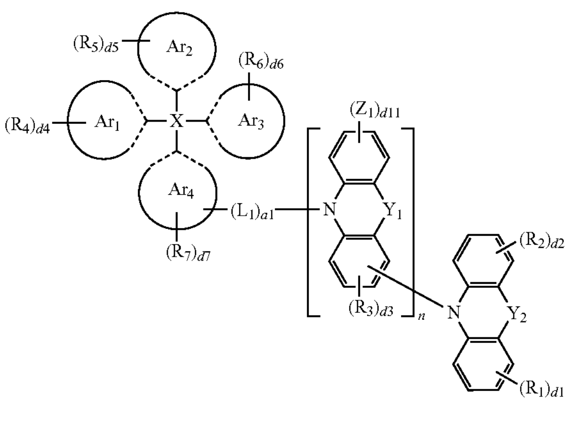

wherein, in Formula 1,

X is a carbon group element except silicon (Si) or germanium (Ge), rings $Ar_1$ to $Ar_4$, are each independently a $C_5$-$C_{30}$ carbocyclic group, $L_1$ is selected from:

a single bond; and a benzene group, a naphthalene group, an anthracene group, a pyrene group, a fluorene group, a dibenzofuran group, and a dibenzothiophene group, each unsubstituted or substituted with at least one $Z_{10a}$, a1 is an integer from 1 to 10, $Y_1$ and $Y_2$ are each independently a single bond or a non-bond, provided that at least one of Y and $Y_2$ is a single bond, n is an integer from 1 to 5, $R_1$, $R_2$, and $R_4$ to $R_7$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $—Si(Q_1)(Q_2)(Q_3)$, $—N(Q_1)(Q_2)$, $—B(Q_1)(Q_2)$, $—C(=O)(Q_1)$, $—S(=O)_2(Q_1)$, and $—P(=O)(Q_1)(Q_2)$, $R_3$ are selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted monovalent non-aromatic condensed polycyclic group, $—Si(Q_1)(Q_2)(Q_3)$, $—B(Q_1)(Q_2)$, $—C(=O)(Q_1)$, $—S(=O)_2(Q_1)$, and $—P(=O)(Q_1)(Q_2)$, $Z_1$ and $Z_{10a}$ are each selected from: hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, $—CD_3$, $—CD_2H$, $—CDH_2$, $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, and a naphthyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, and a cycloheptenyl group, unsubstituted or substituted with at least one selected from deuterium, —F, —Cl, —Br, —I, a hydroxyl group, a cyano group, a nitro group, an amidino group, a hydrazino group, a hydrazono group, $—CD_3$, $—CD_2H$, $—CDH_2$, $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, $-Si(Q_{41})(Q_{42})(Q_{43})$, $-N(Q_{41})(Q_{42})$, and $-B(Q_{41})(Q_{42})$; and $-Si(Q_{51})(Q_{52})(Q_{53})$, $-N(Q_{51})(Q_{52})$, and $-B(Q_{51})(Q_{52})$, wherein $Q_{41}$ to $Q_{43}$ and $Q_{51}$ to $Q_{53}$ are each independently selected from:

$-CH_3$, $-CD_3$, $-CD_2H$, $-CDH_2$, $-CH_2CH_3$, $-CH_2CD_3$, $-CH_2CD_2H$, $-CH_2CDH_2$, $-CHDCH_3$, $-CHDCD_2H$, $-CHDCDH_2$, $-CHDCD_3$, $-CD_2CD_3$, $-CD_2CD_2H$, and $-CD_2CDH_2$; and an n-propyl group, an iso-propyl group, an n-butyl group, an isobutyl group, a sec-butyl group, a tert-butyl group, an n-pentyl group, an isopentyl group, a sec-pentyl group, and a tert-pentyl group, each unsubstituted or substituted with at least one selected from deuterium and a $C_1$-$C_{10}$ alkyl group, d1 and d2 are each independently an integer from 1 to 4, d3 is an integer from 1 to 3, d4 to d7 are each independently an integer from 1 to 20, d11 are an integer from 1 to 4, a substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

deuterium (-D), —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, $-Si(Q_{11})(Q_{12})(Q_{13})$, $-N(Q_{11})(Q_{12})$, $-B(Q_{11})(Q_{12})$, $-C(=O)(Q_{11})$, $-S(=O)_2(Q_{11})$, and $-P(=O)(Q_{11})(Q_{12})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each unsubstituted or substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, $-Si(Q_{21})(Q_{22})(Q_{23})$, $-N(Q_{21})(Q_{22})$, $-B(Q_{21})(Q_{22})$, $-C(=O)(Q_{21})$, $-S(=O)_2(Q_{21})$, and $-P(=O)(Q_{21})(Q_{22})$; and $-Si(Q_{31})(Q_{32})(Q_{33})$, $-N(Q_{31})(Q_{32})$, $-B(Q_{31})(Q_{32})$, $-C(=O)(Q_{31})$, $-S(=O)_2(Q_{31})$, and $-P(=O)(Q_{31})(Q_{32})$, wherein $Q_1$ to $Q_3$, $Q_{11}$ to $Q_{13}$, $Q_{21}$ to $Q_{23}$, and $Q_{31}$ to $Q_{33}$ are each independently selected from: hydrogen; deuterium; —F; —Cl; —Br; —I; a hydroxyl group; a cyano group; a nitro group; an amidino group; a hydrazino group; a hydrazono group; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{10}$ cycloalkyl group; a $C_1$-$C_{10}$ heterocycloalkyl group; a $C_3$-$C_{10}$ cycloalkenyl group; a $C_1$-$C_{10}$ heterocycloalkenyl group; a $C_6$-$C_{60}$ aryl group; a $C_1$-$C_{60}$ heteroaryl group; a monovalent non-aromatic condensed polycyclic group; a monovalent nonaromatic condensed heteropolycyclic group; a $C_1$-$C_{60}$ alkyl group substituted with at least one selected from deuterium, —F, and a cyano group; a $C_6$-$C_{60}$ aryl group substituted with at least one selected from deuterium, —F, and a cyano group; a biphenyl group; and a terphenyl group.

2. The organic light-emitting device of claim 1, wherein:

the first electrode is an anode, the second electrode is a cathode, and the at least one heterocyclic compound is comprised in the organic layer, and the organic layer further comprises a hole transport region between the first electrode and the emission layer and an electron transport region between the emission layer and the second electrode.

3. The organic light-emitting device of claim 2, wherein the hole transport region comprises a hole injection layer, a hole transport layer, an emission auxiliary layer, an electron blocking layer, or any combination thereof, and the electron transport region comprises a hole blocking layer, an electron transport layer, an electron injection layer, or any combination thereof.

4. The organic light-emitting device of claim 1, wherein the emission layer comprises the at least one heterocyclic compound.

5. The organic light-emitting device of claim 1, wherein:

the emission layer comprises a host and a dopant, the host is different from the dopant, an amount of the host is greater than an amount of the dopant, and the host comprises the at least one heterocyclic compound.

6. The organic light-emitting device of claim 4, wherein the emission layer emits blue light or blue-green light.

7. The organic light-emitting device of claim 5, wherein the dopant emits blue light or blue-green light having a maximum emission wavelength in a range of about 400 nanometers (nm) to about 500 nm.

8. The organic light-emitting device of claim 5, wherein the dopant comprises a transition metal and does not comprise a transition metal-nitrogen bond and a transition metal-oxygen bond.

9. The organic light-emitting device of claim 5, wherein the dopant comprises a transition metal and a coordinate bond between the transition metal and a carbon atom.

10. An organic light-emitting device comprising:

a first electrode;

a second electrode facing the first electrode;

an organic layer between the first electrode and the second electrode and comprising an emission layer; and at least one heterocyclic compound represented by Formula 1:

Formula 1

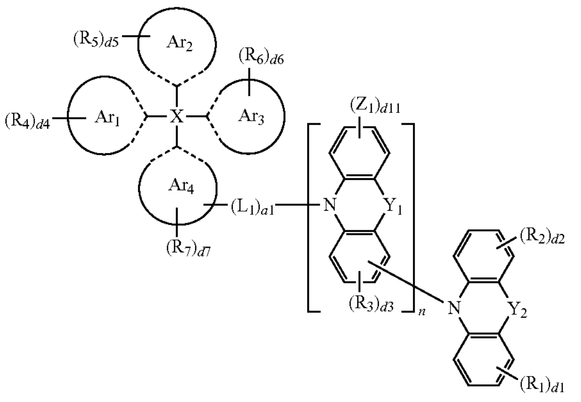

wherein, in Formula 1,

X is a carbon group element except silicon (Si) or germanium (Ge), rings $Ar_1$ to $Ar_4$, are each independently a $C_5$-$C_{30}$ carbocyclic group, $L_1$ is selected from:

a single bond; and a benzene group, a naphthalene group, an anthracene group, a pyrene group, a fluorene group, a dibenzofuran group, and a dibenzothiophene group, each unsubstituted or substituted with at least one $Z_{10a}$, a1 is an integer from 1 to 10, $Y_1$ and $Y_2$ are each independently a single bond or a non-bond, provided that at least one of Y and $Y_2$ is a single bond, n is an integer from 1 to 5, $R_1$ to $R_7$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted 02-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(═O)($Q_1$), —S(═O)$_2$($Q_1$), and —P(═O)($Q_1$)($Q_2$), $Z_1$ and $Z_{10a}$ are each selected from: hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, —$CD_3$, —$CD_2H$, —$CDH_2$, $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, and a naphthyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, and a cycloheptenyl group, unsubstituted or substituted with at least one selected from deuterium, —F, —Cl, —Br, —I, a hydroxyl group, a cyano group, a nitro group, an amidino group, a hydrazino group, a hydrazono group, —$CD_3$, —$CD_2H$, —$CDH_2$, $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, —Si($Q_{41}$)($Q_{42}$)($Q_{43}$), —N($Q_{41}$)($Q_{42}$), and —B($Q_{41}$)($Q_{42}$); and —Si($Q_{51}$)($Q_{52}$)($Q_{53}$), —N($Q_{51}$)($Q_{52}$), and —B($Q_{51}$)($Q_{52}$), wherein $Q_{41}$ to $Q_{43}$ and $Q_{51}$ to $Q_{53}$ are each independently selected from:

—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$; and an n-propyl group, an iso-propyl group, an n-butyl group, an isobutyl group, a sec-butyl group, a tert-butyl group, an n-pentyl group, an isopentyl group, a sec-pentyl group, and a tert-pentyl group, each unsubstituted or substituted with at least one selected from deuterium and a $C_1$-$C_{10}$ alkyl group, d1 and d2 are each independently an integer from 1 to 4, d3 is an integer from 1 to 3, d4 to d7 are each independently an integer from 1 to 20, d11 are an integer from 1 to 4, a substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

deuterium (-D), —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{00}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each unsubstituted or substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_1$ to $Q_3$, $Q_{11}$ to $Q_{13}$, $Q_{21}$ to $Q_{23}$, and $Q_{31}$ to $Q_{33}$ are each independently selected from: hydrogen; deuterium; —F; —Cl; —Br; —I; a hydroxyl group; a cyano group; a nitro group; an amidino group; a hydrazino group; a hydrazono group; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{10}$ cycloalkyl group; a $C_1$-$C_{10}$ heterocycloalkyl group; a $C_3$-$C_{10}$ cycloalkenyl group; a $C_1$-$C_{10}$ heterocycloalkenyl group; a $C_6$-$C_{60}$ aryl group; a $C_1$-$C_{60}$ heteroaryl group; a monovalent non-aromatic condensed polycyclic group; a monovalent non-aromatic condensed heteropolycyclic group; a $C_1$-$C_{60}$ alkyl group substituted with at least one selected from deuterium, —F, and a cyano group; a $C_6$-$C_{60}$ aryl group substituted with at least one selected from deuterium, —F, and a cyano group; a biphenyl group; and a terphenyl group, and wherein the at least one heterocyclic compound is used as a material for a capping layer outside a pair of electrodes of the organic light-emitting device.

11. A heterocyclic compound represented by Formula 1:

Formula 1

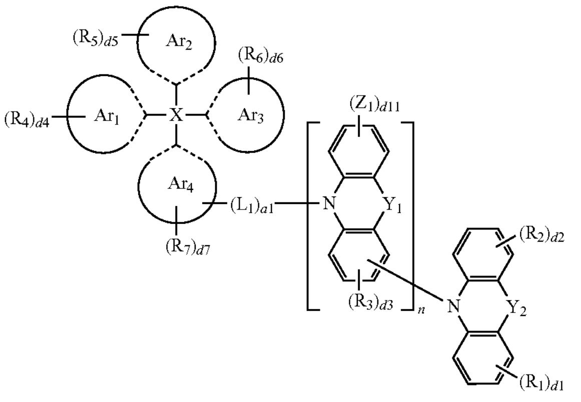

wherein, in Formula 1,

X is a carbon group element except silicon (Si) or germanium (Ge), rings $Ar_1$ to $Ar_4$ are each independently a $C_5$-$C_{30}$ carbocyclic group, $L_1$ is selected from:

a single bond; and a benzene group, a naphthalene group, an anthracene group, a pyrene group, a fluorene group, a dibenzofuran group, and a dibenzothiophene group, each unsubstituted or substituted with at least one $Z_{10a}$, a1 is an integer from 1 to 10, $Y_1$ and $Y_2$ are each independently a single bond or a non-bond, provided that at least one of Y and $Y_2$ is a single bond, n is an integer from 1 to 5, $R_1$, $R_2$, and $R_4$ to $R_7$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$), $R_3$ are selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted monovalent non-aromatic condensed polycyclic group, —Si($Q_1$)($Q_2$)($Q_3$), —B($Q_1$)($Q_2$), —C(=O)($Q_1$), —S(=O)$_2$($Q_1$), and —P(=O)($Q_1$)($Q_2$), $Z_1$ and $Z_{10a}$ are each selected from: hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group, a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, —$CD_3$, —$CD_2H$, —$CDH_2$, $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, and a naphthyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, and a cycloheptenyl group, unsubstituted or substituted with at least one selected from deuterium, —F, —Cl, —Br, —I, a hydroxyl group, a cyano group, a nitro group, an amidino group, a hydrazino group, a hydrazono group, —$CD_3$, —$CD_2H$, —$CDH_2$, $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, —Si($Q_{41}$)($Q_{42}$)($Q_{43}$), —N($Q_{41}$)($Q_{42}$), and —B($Q_{41}$)($Q_{42}$); and —Si($Q_{51}$)($Q_{52}$)($Q_{53}$), —N($Q_{51}$)($Q_{52}$), and —B($Q_{51}$)($Q_{52}$), wherein $Q_{41}$ to $Q_{43}$ and $Q_{51}$ to $Q_{53}$ are each independently selected from:

—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$; and an n-propyl group, an iso-propyl group, an n-butyl group, an isobutyl group, a sec-butyl group, a tert-butyl group, an n-pentyl group, an isopentyl group, a sec-pentyl group, and a tert-pentyl group, each unsubstituted or substituted with at least one selected from deuterium and a $C_1$-$C_{10}$ alkyl group, d1 and d2 are each independently an integer from 1 to 4, d3 is an integer from 1 to 3, d4 to d7 are each independently an integer from 1 to 20, d11 are each an integer from 1 to 4, a substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

deuterium (-D), —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each unsubstituted or substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_1$ to $Q_3$, $Q_{11}$ to $Q_{13}$, $Q_{21}$ to $Q_{23}$, and $Q_{31}$ to $Q_{33}$ are each independently selected from: hydrogen; deuterium; —F; —Cl; —Br; —I; a hydroxyl group; a cyano group; a nitro group; an amidino group; a hydrazino group; a hydrazono group; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{10}$ cycloalkyl group; a $C_1$-$C_{10}$ heterocycloalkyl group; a $C_3$-$C_{10}$ cycloalkenyl group; a $C_1$-$C_{10}$ heterocycloalkenyl group; a $C_6$-$C_{60}$ aryl group; a $C_1$-$C_{60}$ heteroaryl group; a monovalent non-aromatic condensed polycyclic group; a monovalent nonaromatic condensed heteropolycyclic group; a $C_1$-$C_{60}$ alkyl group substituted with at least one selected from deuterium, —F, and a cyano group; a $C_6$-$C_{60}$ aryl group substituted with at least one selected from deuterium, —F, and a cyano group; a biphenyl group; and a terphenyl group.

12. The heterocyclic compound of claim 11, wherein X is carbon (C), or tin (Sn).

13. The heterocyclic compound of claim 11, wherein rings $Ar_1$ to $Ar_4$ are each independently a benzene group, a naphthalene group, an anthracene group, a phenanthrene group, a triphenylene group, a pyrene group, a chrysene group, a cyclopentadiene group, or a 1,2,3,4-tetrahydronaphthalene group.

14. The heterocyclic compound of claim 11, wherein *-$L_1$-*' is: a single bond; or a group represented by one of Formulae 4-1 to 4-9:

4-1

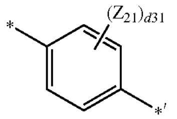

4-2

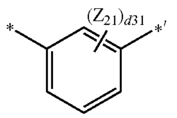

4-3

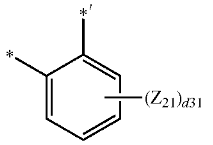

4-4

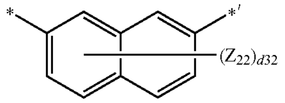

4-5

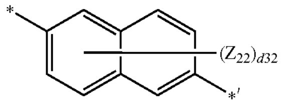

4-6

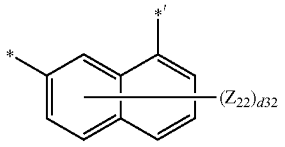

4-7

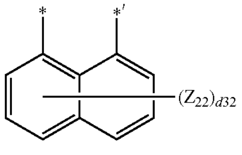

4-8

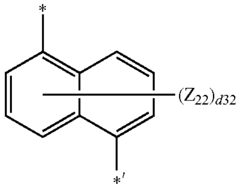

4-9

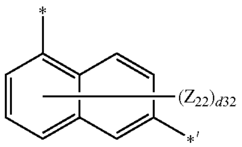

wherein, in Formulae 4-1 to 4-9, $Z_{21}$ and $Z_{22}$ are each the same as described with respect to $Z_{10a}$ in claim 11, d31 is an integer from 1 to 4, d32 is an integer from 1 to 6, and

* and *' each indicate a binding site to an adjacent atom.

15. The heterocyclic compound of claim 11, wherein:

$Y_1$ is a single bond, and $Y_2$ is a single bond;

$Y_1$ is a non-bond, and $Y_2$ is a single bond;

$Y_1$ is a single bond, and $Y_2$ is a non-bond; or $Y_1$ is a non-bond, and $Y_2$ is a non-bond.

16. The heterocyclic compound of claim 11, wherein $R_1$, $R_2$, and $R_4$ to $R_7$ are each independently selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, $—CD_3$, $—CD_2H$, $—CDH_2$, $—CF_3$, $—CF_2H$, $—CFH_2$, a hydroxyl group, a cyano group, a nitro group, an amidino group, a hydrazino group, a hydrazono group, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a naphthyl group, a pyridinyl group, and a pyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a $C_1$-$C_{10}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, an azacarbazolyl group, an azadibenzofuranyl group, an azadibenzothiophenyl group, an azafluorenyl group, and an azadibenzosilolyl group, each substituted with at least one selected from deuterium, —F, —Cl, —Br, —I, $—CD_3$, $—CD_2H$, $—CDH_2$, $—CF_3$, $—CF_2H$, $—CFH_2$, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a $C_1$-$C_{10}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, $—Si(Q_{31})(Q_{32})(Q_{33})$, $—N(Q_{31})(Q_{32})$, $—B(Q_{31})(Q_{32})$, $—P(Q_{31})(Q_{32})$, $—C(=O)(Q_{31})$, $—S(=O)_2(Q_{31})$, and $—P(=O)(Q_{31})(Q_{32})$;

$—Si(Q_1)(Q_2)(Q_3)$, $—N(Q_1)(Q_2)$, $—B(Q_1)(Q_2)$, $—C(=O)(Q_1)$, $—S(=O)_2(Q_1)$, and $—P(=O)(Q_1)(Q_2)$; and a group represented by Formula 2-1:

2-1

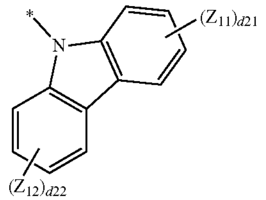

wherein, in Formula 2-1, $Z_{11}$ and $Z_{12}$ are each understood by referring to the description of $Z_1$ in claim 11, d21 and d22 are each independently an integer from 1 to 4, wherein $Q_1$ to $Q_3$ and $Q_{31}$ to $Q_{33}$ are each independently selected from:

$—CH_3$, $—CD_3$, $—CD_2H$, $—CDH_2$, $—CH_2CH_3$, $—CH_2CD_3$, $—CH_2CD_2H$, $—CH_2CDH_2$, $—CHDCH_3$, $—CHDCD_2H$, $—CHDCDH_2$, $—CHDCD_3$, $—CD_2CD_3$, $—CD_2CD_2H$, and $—CD_2CDH_2$; and an n-propyl group, an iso-propyl group, an n-butyl group, an isobutyl group, a sec-butyl group, a tert-butyl group, an n-pentyl group, an isopentyl group, a sec-pentyl group, a tert-pentyl group, a phenyl group, a naphthyl group, a pyridinyl group, a pyrimidinyl group, a pyridazinyl group, a pyrazinyl group, and a triazinyl group, each unsubstituted or substituted with at least one selected from deuterium, a $C_1$-$C_{10}$ alkyl group, a phenyl group, a biphenyl group, a pyridinyl group, a pyrimidinyl group, a pyridazinyl group, a pyrazinyl group, and a triazinyl group.

17. The heterocyclic compound of claim 11, wherein the heterocyclic compound is represented by Formula 1-1:

Formula 1-1

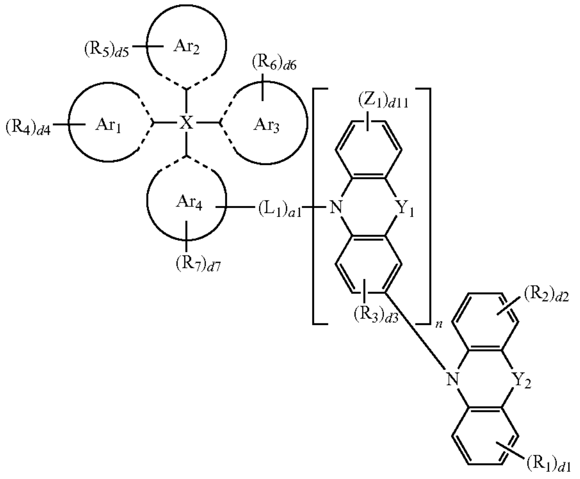

wherein, in Formula 1-1, X, ring $Ar_1$ to $Ar_4$, $L_1$, a1, $Y_1$, $Y_2$, n, $R_1$ to $R_7$, $Z_1$, d1 to d7, and d11 are respectively the same as described with respect to X, ring $Ar_1$ to $Ar_4$, $L_1$, a1, $Y_1$, $Y_2$, n, $R_1$ to $R_7$, $Z_1$, d1 to d7, and d11 in claim 11.

18. The heterocyclic compound of claim 11, wherein a portion represented by

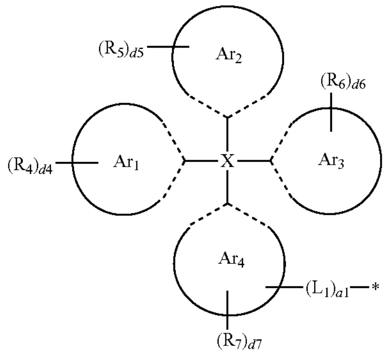

in Formula 1 is represented by one of Formulae 3-1 to 3-3:

3-1

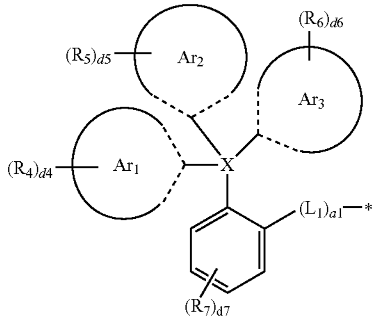

-continued 3-2

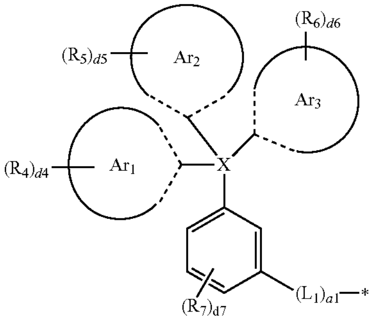

3-3

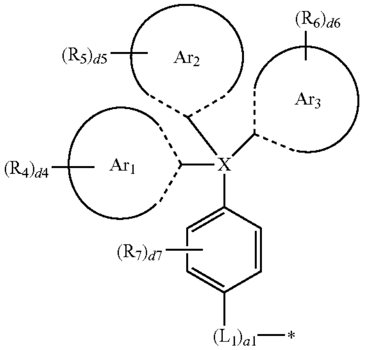

wherein, in Formulae 3-1 to 3-3, d7 is an integer from 1 to 4,

X, ring $Ar_1$ to $Ar_4$, $L_1$, a1, $R_4$ to $R_7$, $Z_1$, and d4 to d7 are the same as described with respect to X, ring $Ar_1$ to $Ar_4$, $L_1$, a1, $R_4$ to $R_7$, $Z_1$, and d4 to d7 in claim 11, and

* indicates a binding site to an adjacent atom.

19. The heterocyclic compound of claim 11, wherein a portion represented by

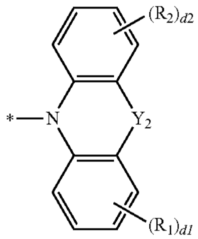

in Formula 1 is represented by one of Formulae 5-1to 5-36:

5-1

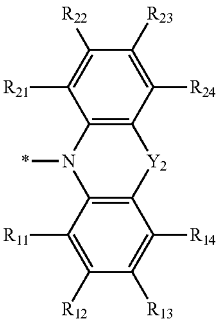

-continued 5-2

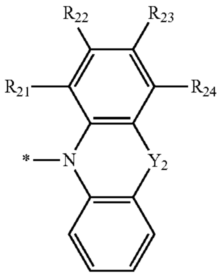

5-3

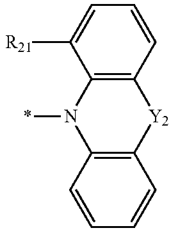

5-4

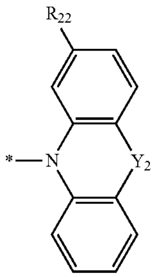

5-5

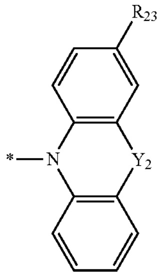

5-6

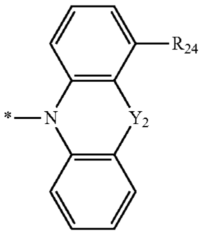

5-7

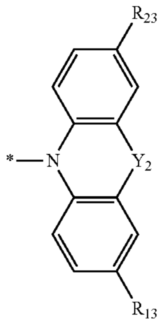

-continued
5-8
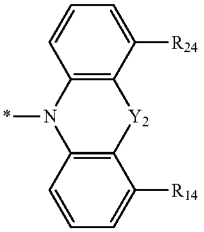
5-9
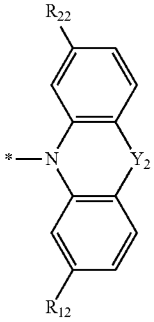
5-10
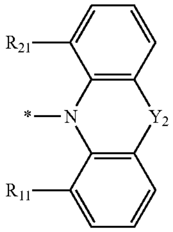
5-11
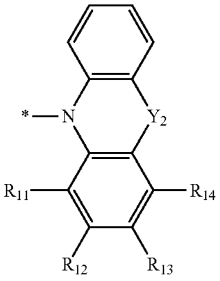
5-12
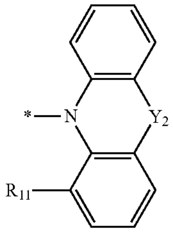
5-13
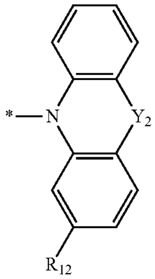
-continued
5-14
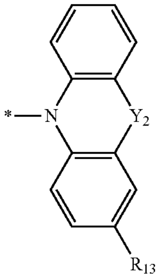
5-15
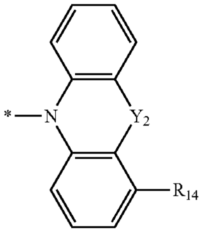
5-16
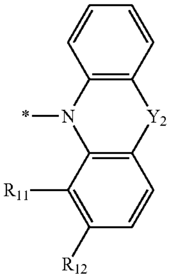
5-17
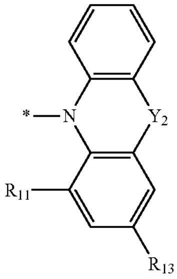
5-18
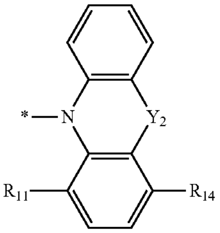
5-19
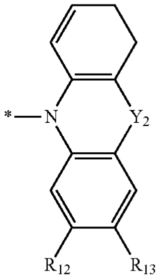

5-20
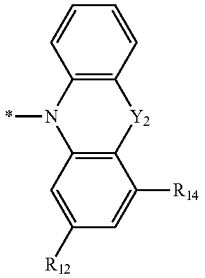
5-21
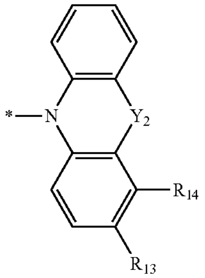
5-22
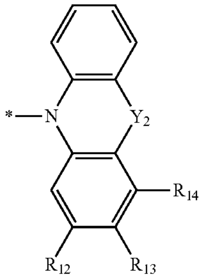
5-23
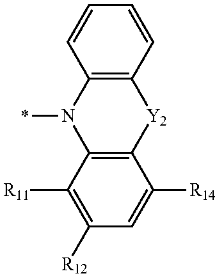
5-24
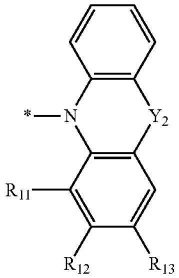
5-25
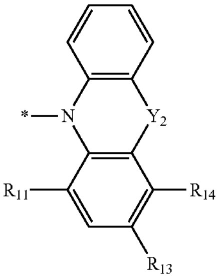
5-26
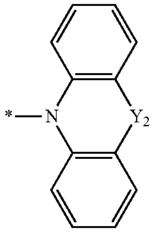
5-27
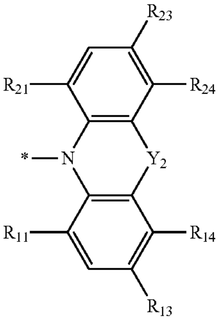
5-28
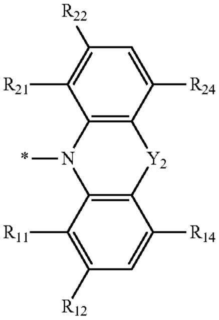
5-29
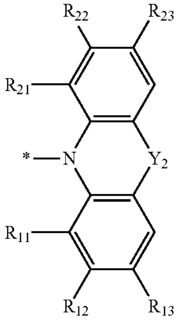

-continued 5-30

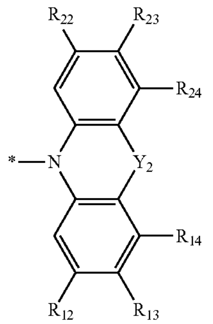

5-31

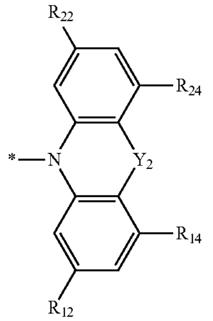

5-32

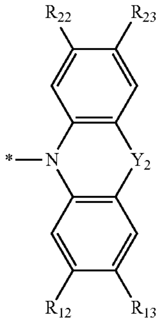

5-33

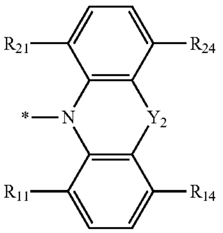

5-34

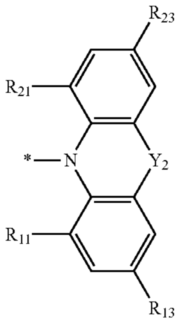

-continued 5-35

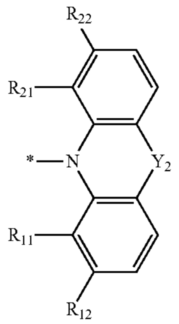

5-36

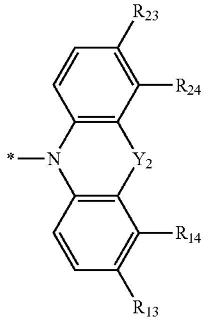

wherein, in Formulae 5-1 to 5-36, $Y_2$ is the same as described with respect to $Y_2$ in claim 11, and $R_{11}$ to $R_{14}$ are each the same as described with respect to $R_1$ in claim 11, and $R_{21}$ to $R_{24}$ are each the same as described with respect to $R_2$ in claim 11, provided that $R_{11}$ to $R_{14}$ and $R_{21}$ to $R_{24}$ are not hydrogen.

20. The heterocyclic compound of claim 11, wherein the heterocyclic compound is any one of Compounds 1, 2, 4 to 6, 8 to 10, 12 to 14, 16 to 18, 20 to 22, 24, 25, 27, 28, 30, 31, 33 to 36, 40 to 44, 47 to 50, 52 to 54, 56, 61, 62, 65, 66, 69, 70, and 73 to 80:

1

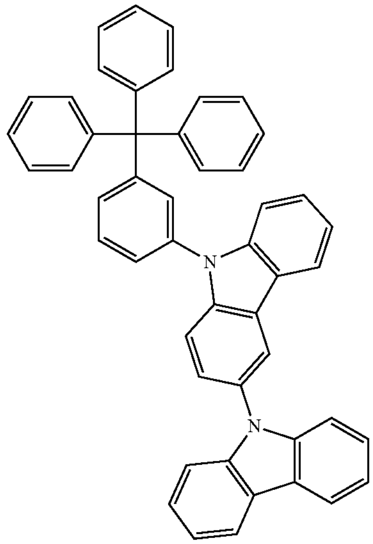

-continued
2
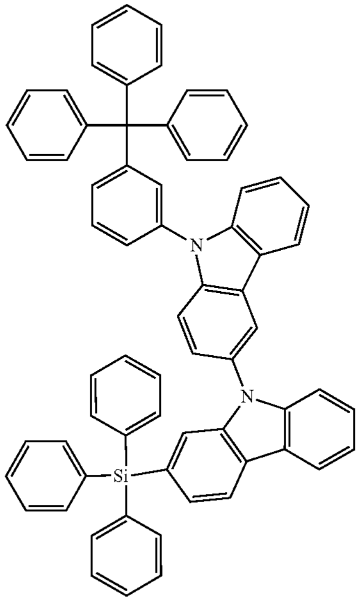
4
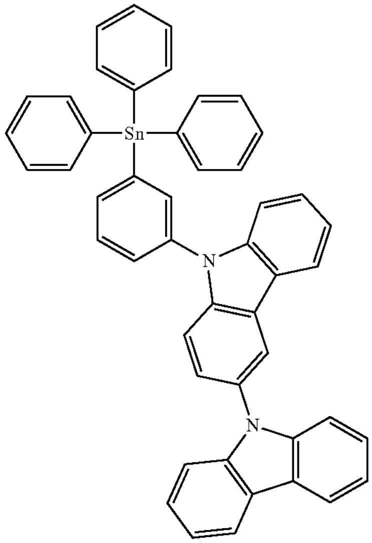
-continued
5
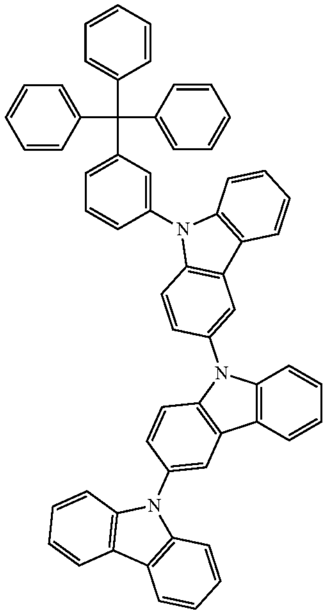
6
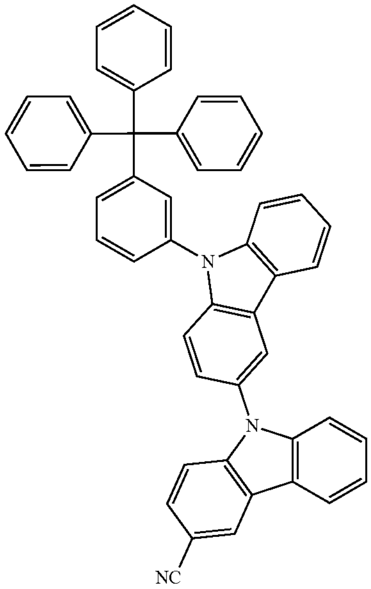

-continued
8
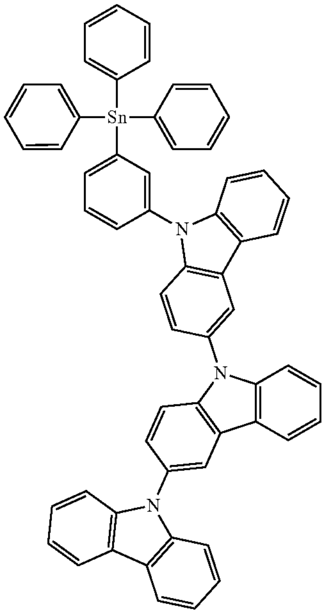
9
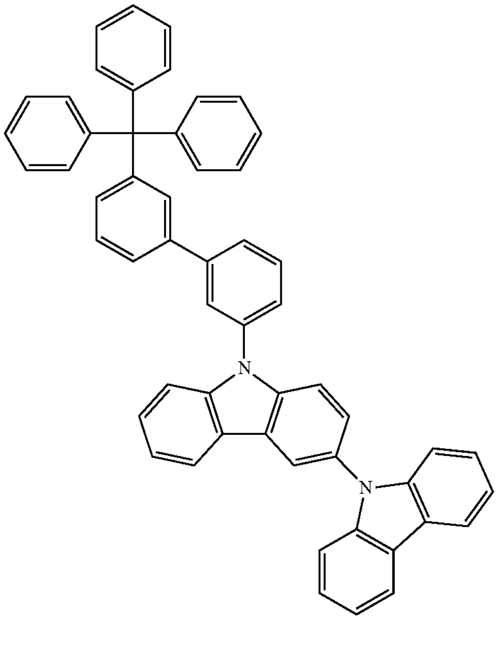
-continued
10
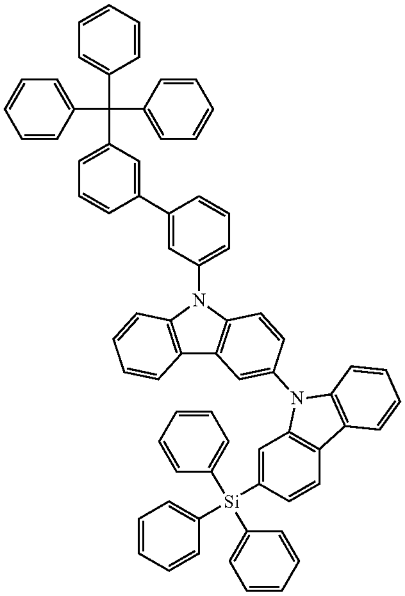
12
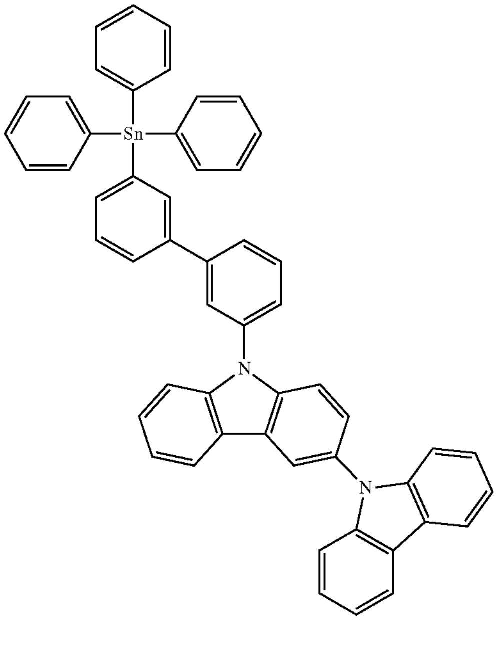

-continued
13
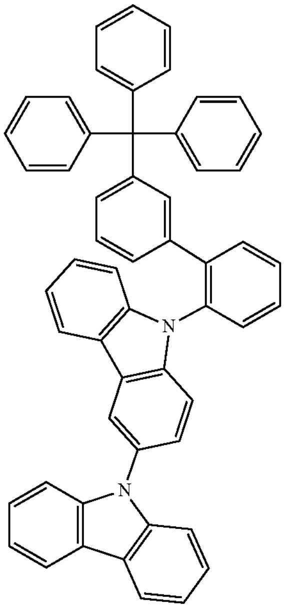
14
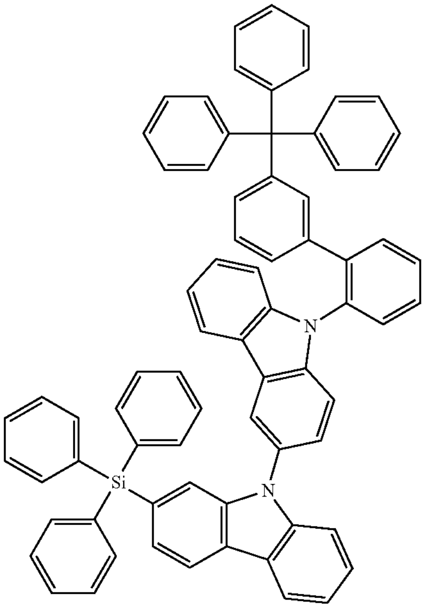
-continued
16
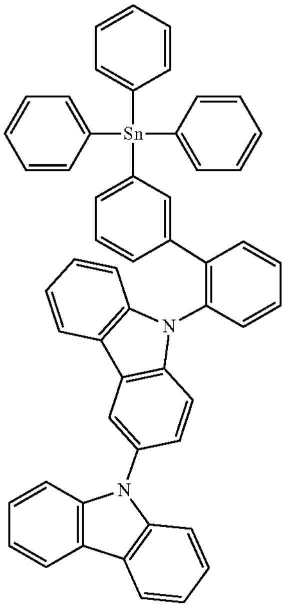
17
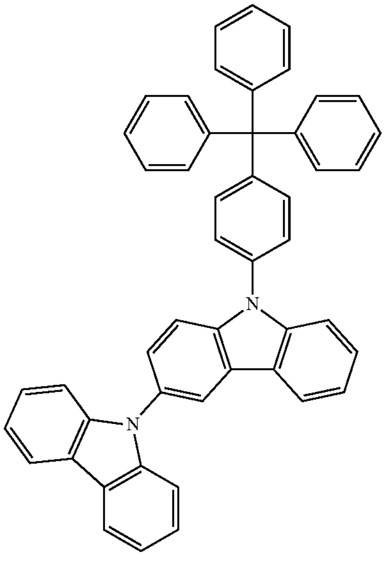

-continued
18
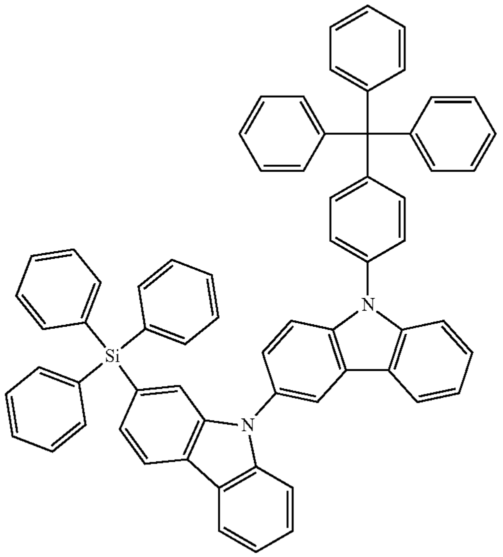
20
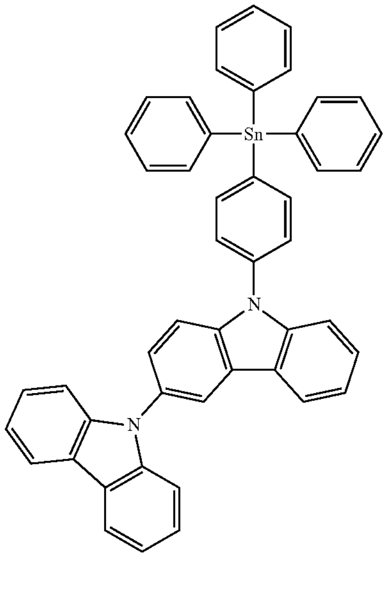
-continued
21
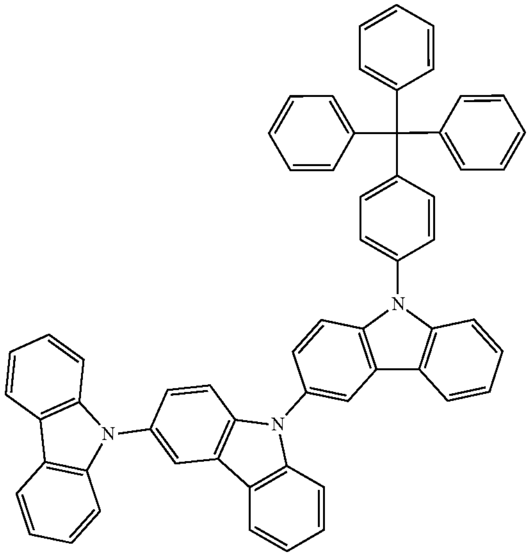
22
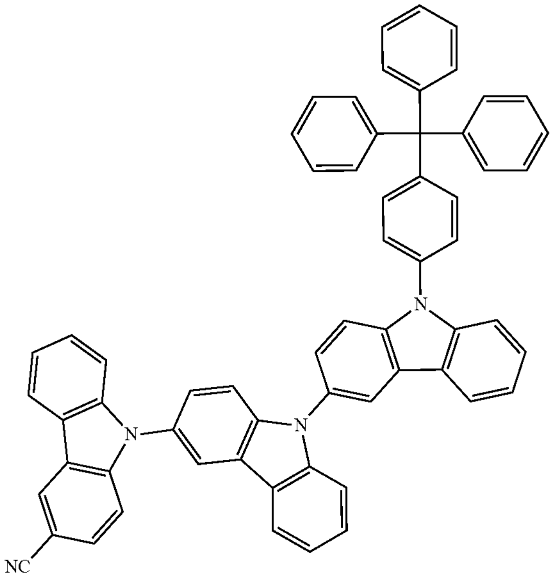

-continued
24
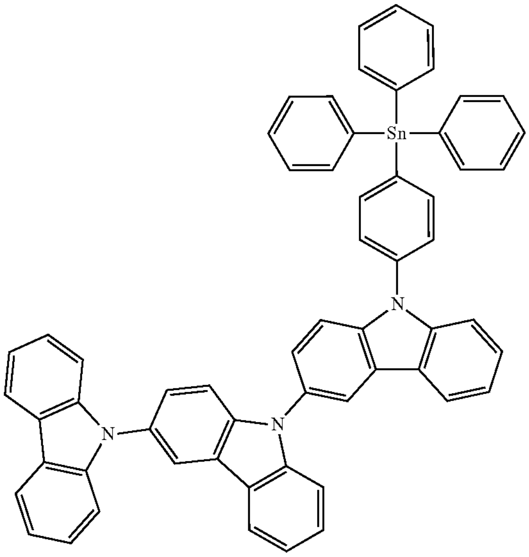
25
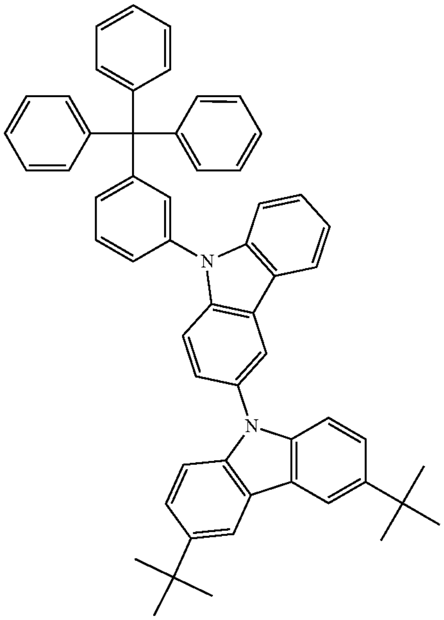
-continued
27
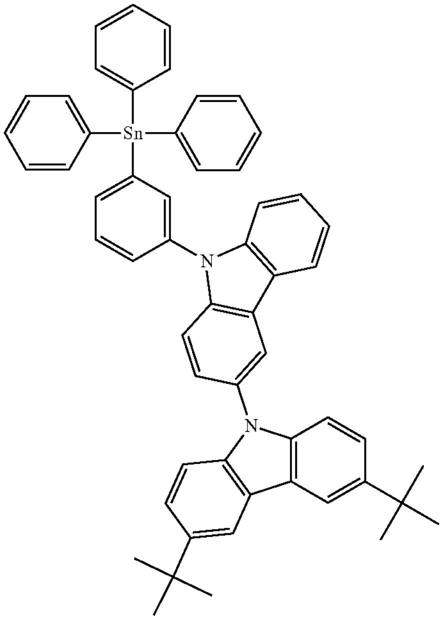
28
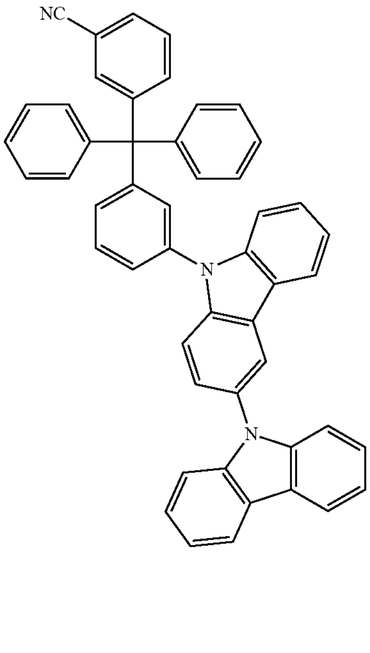

30
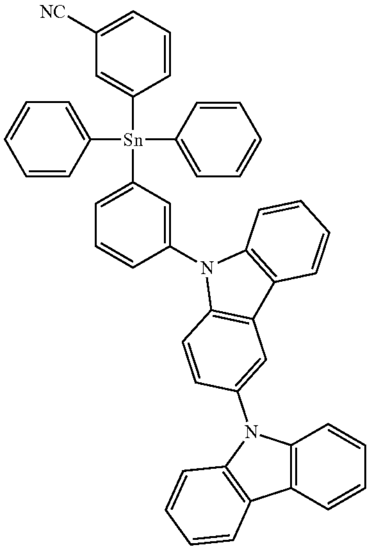
31
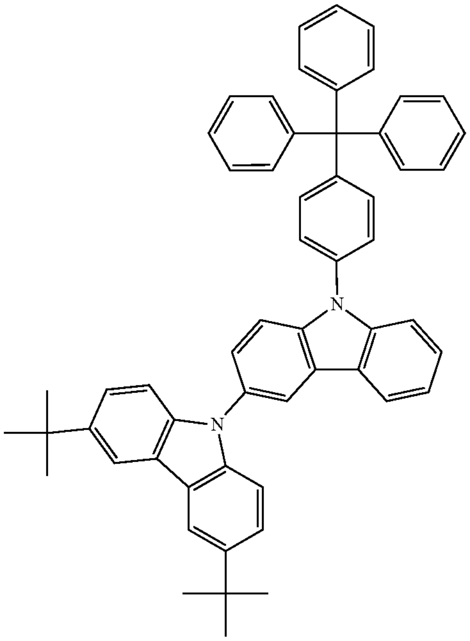
33
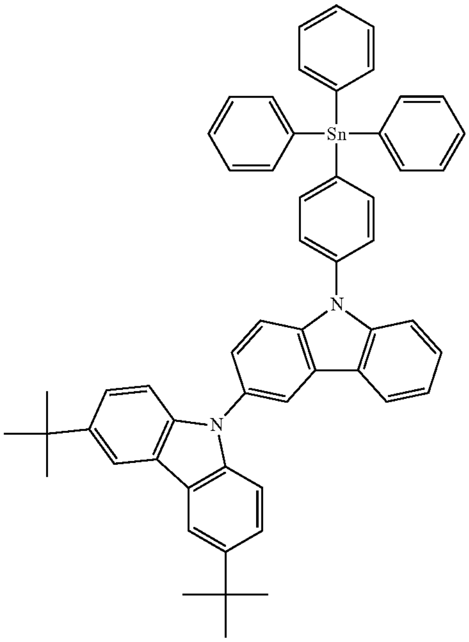
34
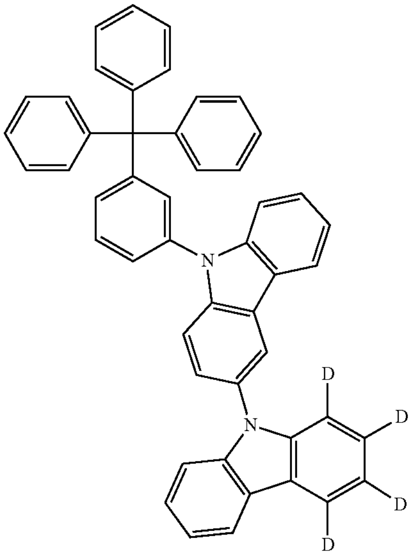

-continued
35
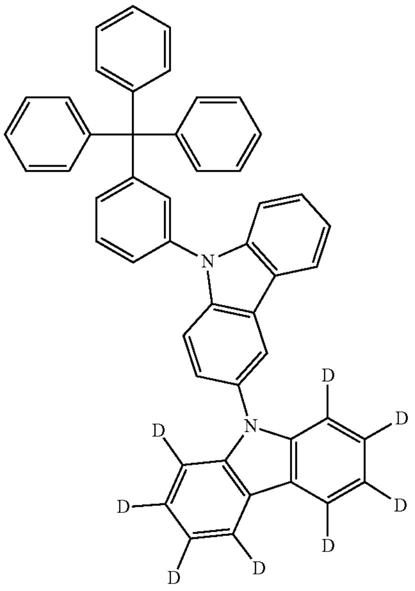
36
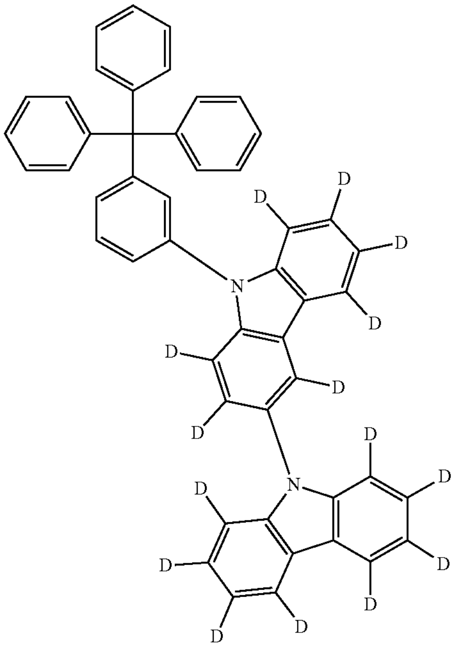
-continued
40
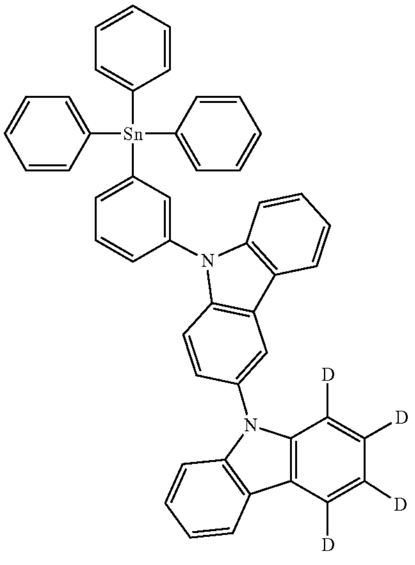
41
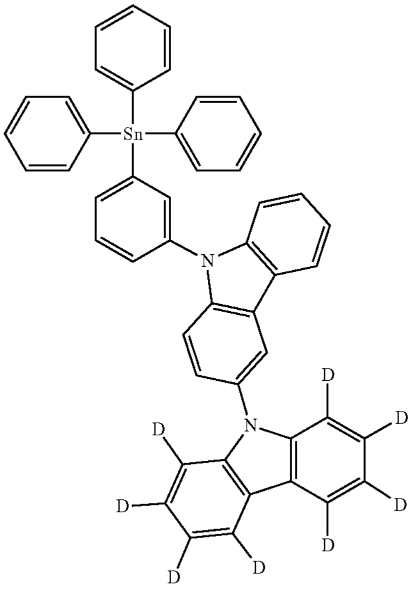

-continued
42
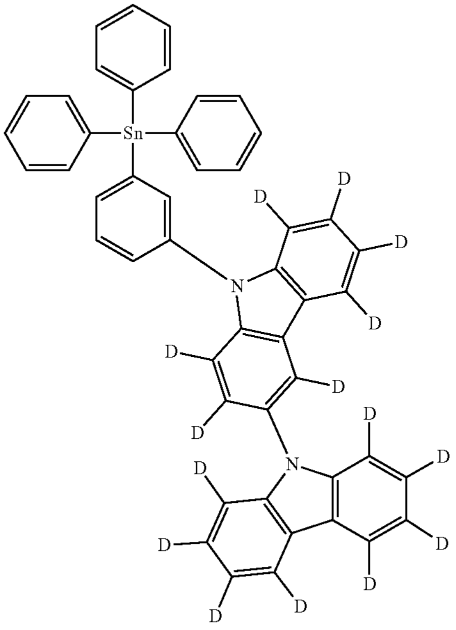
43
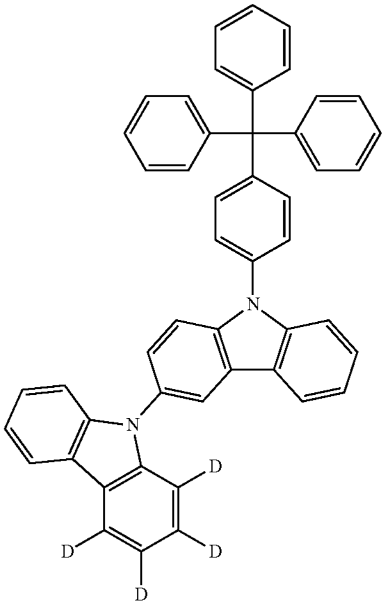
-continued
44
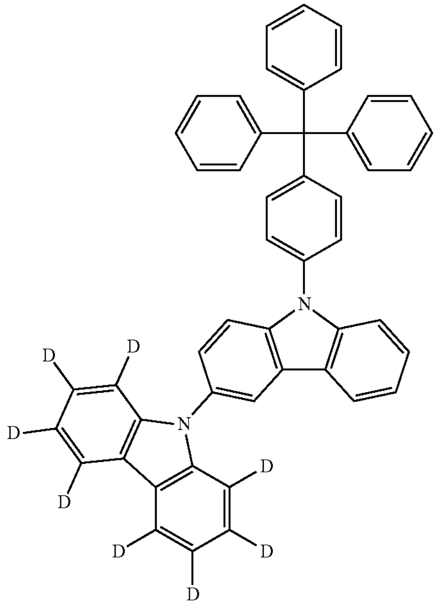
47
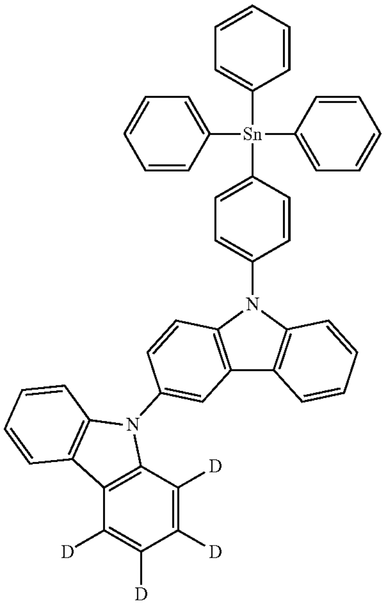

-continued
48
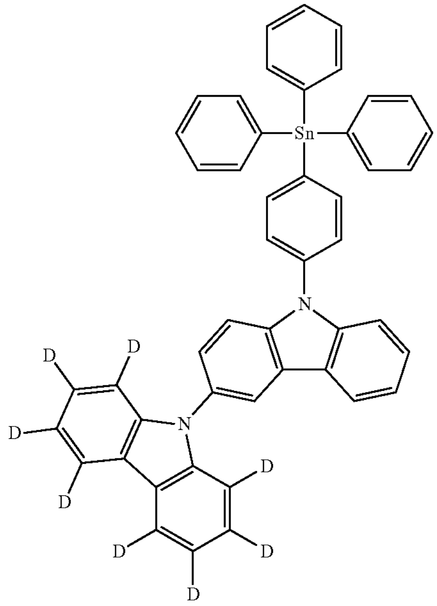
49
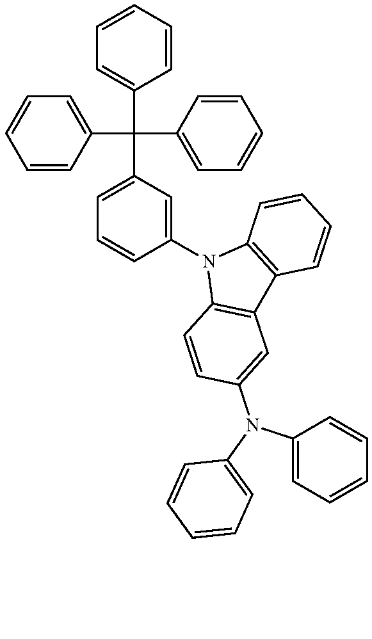
-continued
50
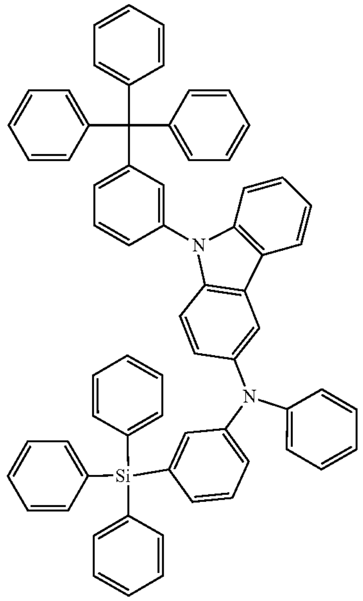
52
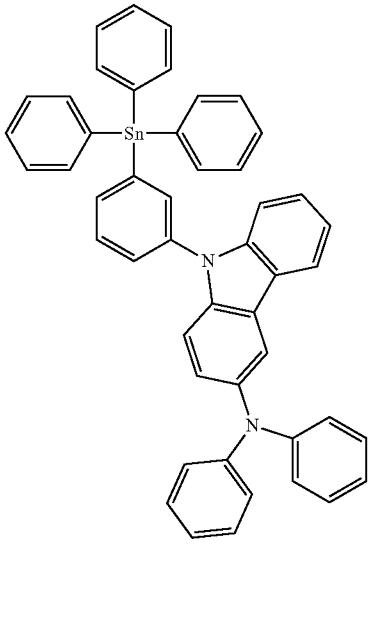

-continued
53
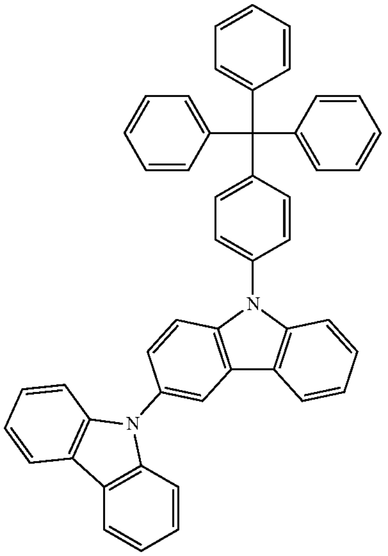
54
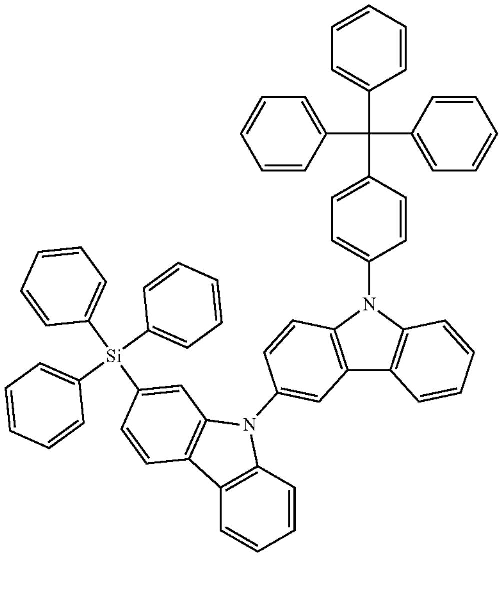
-continued
56
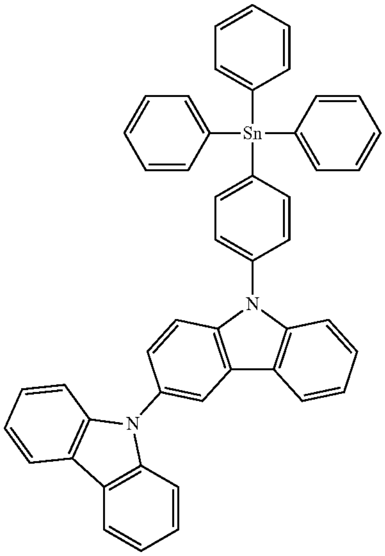
61
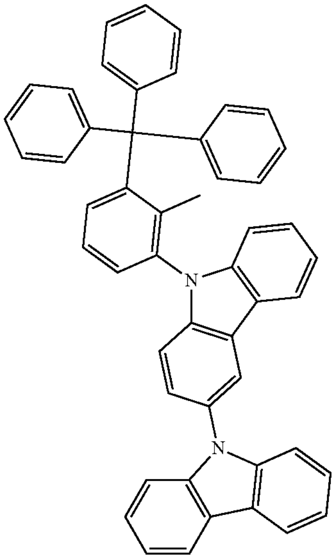

62
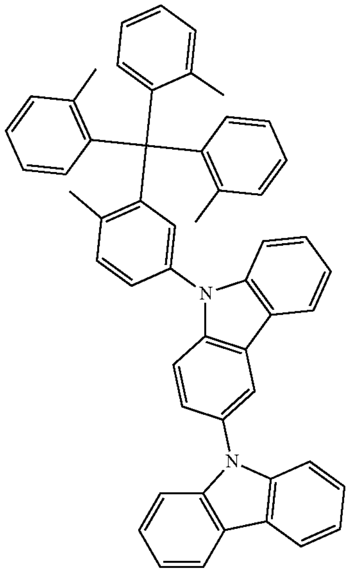
65
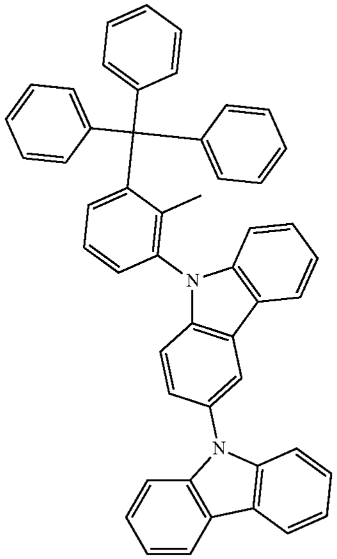
66
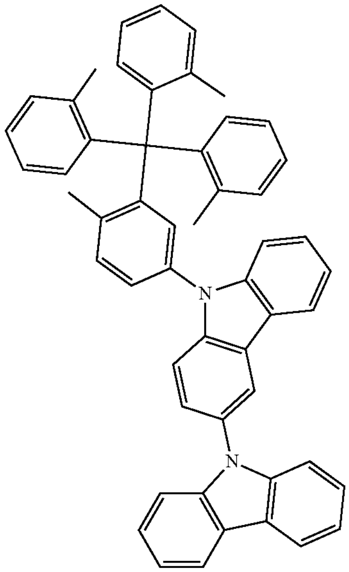
69
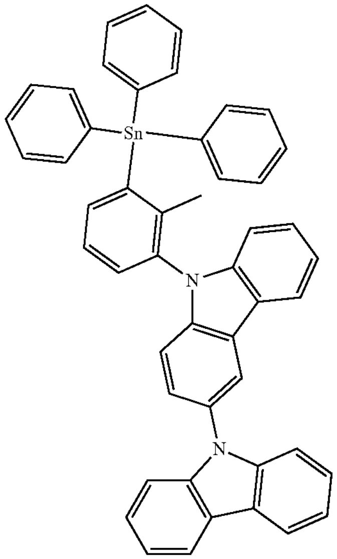

-continued
70
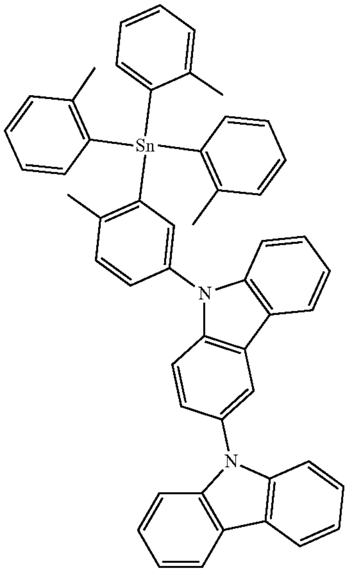
73
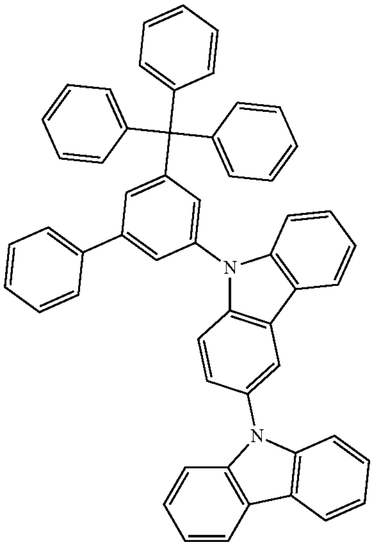
74
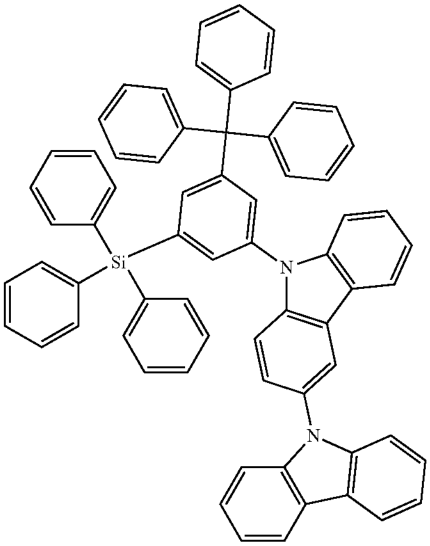
-continued
75
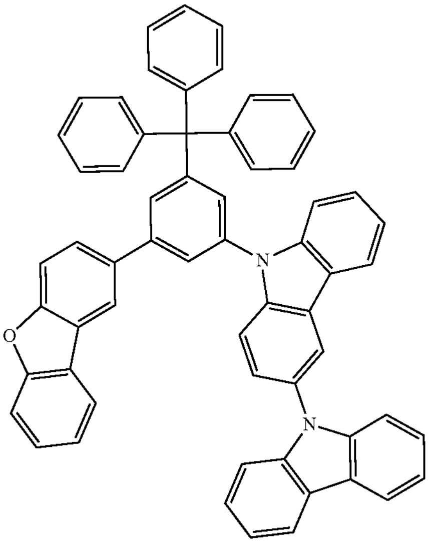
76
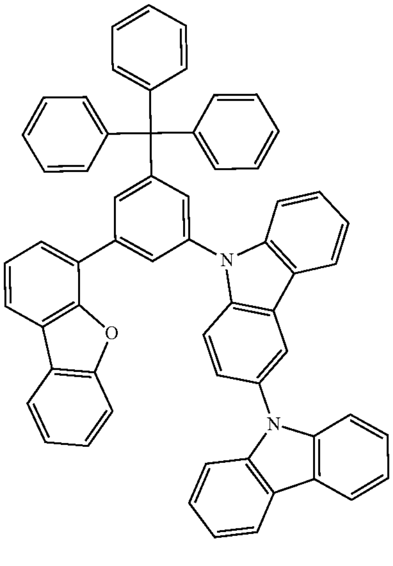

-continued
77
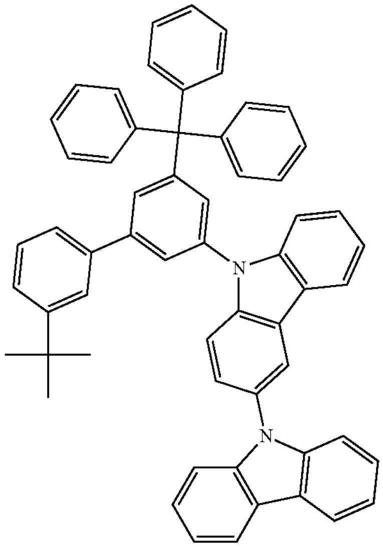
78
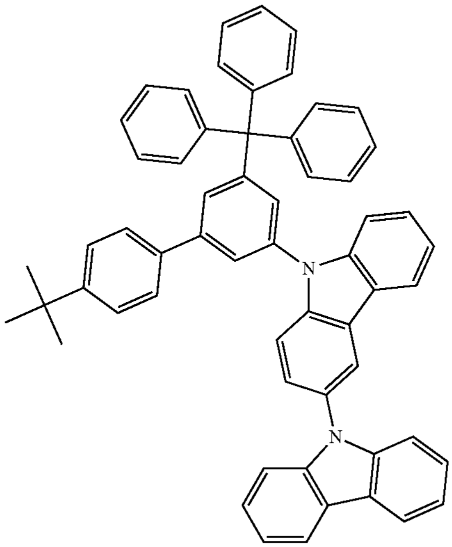
-continued
79
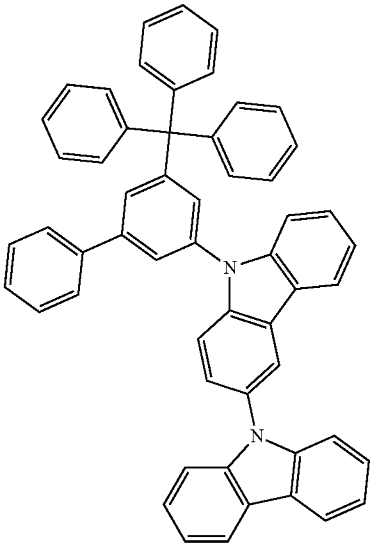
80
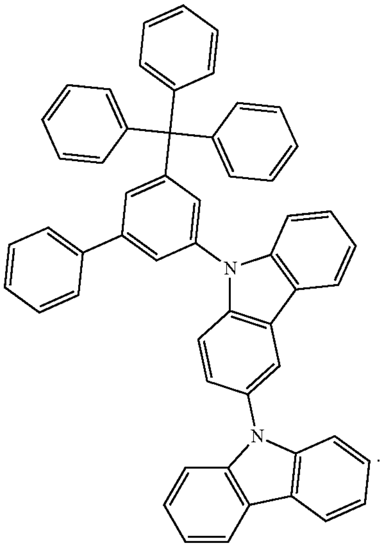
* * * * *